(12) United States Patent
Nelson et al.

(10) Patent No.: US 9,005,203 B2
(45) Date of Patent: Apr. 14, 2015

(54) RECIPROCATING SURGICAL INSTRUMENTS

(75) Inventors: Keith J. Nelson, Logan, UT (US); Andrew R. Fauth, River Heights, UT (US); Trevor K. Lewis, Lehi, UT (US); Daniel J. Triplett, Providence, UT (US)

(73) Assignees: IMDS, LLC, Providence, UT (US); Keith J. Nelson, Logan, UT (US)

( * ) Notice: Subject to any disclaimer, the term of this patent is extended or adjusted under 35 U.S.C. 154(b) by 165 days.

(21) Appl. No.: 13/231,138

(22) Filed: Sep. 13, 2011

(65) Prior Publication Data

US 2012/0046682 A1    Feb. 23, 2012

Related U.S. Application Data

(63) Continuation-in-part of application No. 13/102,351, filed on May 6, 2011, which is a continuation-in-part of application No. 12/765,451, filed on Apr. 22, 2010, now Pat. No. 8,617,164.

(Continued)

(51) Int. Cl.
*A61B 17/00* (2006.01)
*A61B 17/32* (2006.01)
(Continued)

(52) U.S. Cl.
CPC ............ *A61B 17/1624* (2013.01); *A61B 10/06* (2013.01); *A61B 17/1606* (2013.01); *A61B 17/162* (2013.01); *A61B 17/1628* (2013.01); *A61B 17/1644* (2013.01); *A61B 17/1659* (2013.01);
(Continued)

(58) Field of Classification Search
USPC .............. 606/79–85, 170, 171, 176, 177, 180
See application file for complete search history.

(56) References Cited

U.S. PATENT DOCUMENTS

| | | | |
|---|---|---|---|
| 3,596,525 A | 8/1971 | Niesz | |
| 3,884,238 A | 5/1975 | O'Malley | |

(Continued)

FOREIGN PATENT DOCUMENTS

| | | |
|---|---|---|
| WO | WO 93/11910 A1 | 6/1993 |
| WO | WO9913789 | 3/1999 |

(Continued)

OTHER PUBLICATIONS http://global.smith-nephew.com/us/DYINICS_ARTHOSCOPIC Smith & Nephew Dyonics & Powermax Elite.

(Continued)

*Primary Examiner* — Andrew Yang
*Assistant Examiner* — Diana S Jones
(74) *Attorney, Agent, or Firm* — Craig Buschmann; Ryan L. Marshall; Brinks Gilson & Lione

(57) ABSTRACT

A surgical instrument system functional in multiple orthopedic applications, including but not limited to shoulder, knee, hip, wrist, ankle, spinal, or other joint procedures. The system comprises a cutting head which includes jaw members which may be urged between open and closed positions to providing a biting or chewing action for removal of targeted tissues. The instrument system is configured to be driven by an attached hub that translates a rotational movement into a reciprocating motion to open and close the jaw members. Suction for removal of bone fragments or other tissues is provided through a suction opening.

33 Claims, 39 Drawing Sheets

Related U.S. Application Data

(60) Provisional application No. 61/245,487, filed on Sep. 24, 2009, provisional application No. 61/332,308, filed on May 7, 2010, provisional application No. 61/382,795, filed on Sep. 14, 2010, provisional application No. 61/382,790, filed on Sep. 14, 2010.

(51) Int. Cl.
| | |
|---|---|
| *A61B 17/16* | (2006.01) |
| *A61B 18/14* | (2006.01) |
| *A61B 10/06* | (2006.01) |
| *A61B 17/3201* | (2006.01) |
| *A61B 19/00* | (2006.01) |
| *A61B 17/29* | (2006.01) |
| *A61B 18/00* | (2006.01) |
| *A61B 18/18* | (2006.01) |

(52) U.S. Cl.
CPC ....... *A61B 17/32002* (2013.01); *A61B 17/3201* (2013.01); *A61B 18/148* (2013.01); *A61B 19/5212* (2013.01); *A61B 2017/2934* (2013.01); *A61B 2017/2936* (2013.01); *A61B 2017/320008* (2013.01); *A61B 2017/320028* (2013.01); *A61B 2017/320032* (2013.01); *A61B 2018/00196* (2013.01); *A61B 2018/1861* (2013.01); *A61B 2217/005* (2013.01); *A61B 2218/007* (2013.01)

(56) References Cited

U.S. PATENT DOCUMENTS

| | | | |
|---|---|---|---|
| 4,108,182 A | 8/1978 | Hartman | |
| 4,210,146 A | 7/1980 | Banko | |
| 4,246,902 A | 1/1981 | Martinez | |
| 4,314,560 A | 2/1982 | Helfgott | |
| 4,530,357 A | 7/1985 | Pawloski | |
| 4,589,414 A | 5/1986 | Yoshida | |
| 4,625,725 A | 12/1986 | Davison et al. | |
| 4,662,371 A * | 5/1987 | Whipple et al. | 606/170 |
| 4,700,702 A | 10/1987 | Nilsson | |
| 4,727,941 A | 3/1988 | Fulton | |
| 4,728,319 A | 3/1988 | Masch | |
| 4,936,845 A | 6/1990 | Stevens | |
| 5,152,744 A | 10/1992 | Krause | |
| 5,185,934 A | 2/1993 | Tillman | |
| 5,282,816 A | 2/1994 | Miller et al. | |
| 5,364,395 A | 11/1994 | West, Jr. | |
| 5,387,215 A | 2/1995 | Fisher | |
| 5,403,276 A | 4/1995 | Schechter | |
| 5,411,513 A | 5/1995 | Ireland | |
| 5,437,630 A | 8/1995 | Daniel | |
| 5,490,860 A | 2/1996 | Middle | |
| 5,527,331 A | 6/1996 | Kresch et al. | |
| 5,540,693 A | 7/1996 | Fisher | |
| 5,593,415 A | 1/1997 | Sorin | |
| 5,632,759 A | 5/1997 | Rexroth | |
| 5,643,304 A | 7/1997 | Schechter | |
| 5,669,876 A | 9/1997 | Schechter | |
| 5,685,840 A | 11/1997 | Schechter | |
| 5,707,374 A | 1/1998 | Schmidt | |
| 5,810,860 A | 9/1998 | Sorin | |
| 5,814,049 A | 9/1998 | Pratt et al. | |
| 5,817,050 A | 10/1998 | Klein | |
| 5,833,643 A | 11/1998 | Ross | |
| 5,904,681 A | 5/1999 | West, Jr. | |
| 5,925,055 A | 7/1999 | Adrian | |
| 5,957,881 A | 9/1999 | Peters | |
| 6,042,593 A | 3/2000 | Storz | |
| 6,048,345 A | 4/2000 | Berke | |
| 6,083,228 A | 7/2000 | Michelson | |
| 6,193,715 B1 | 2/2001 | Wrublewski et al. | |
| 6,368,324 B1 | 4/2002 | Dinger | |
| 6,451,017 B1 | 9/2002 | Moutafis et al. | |
| 6,451,022 B2 | 9/2002 | Dinger | |
| 6,537,280 B2 | 3/2003 | Dinger | |
| 6,595,996 B2 | 7/2003 | Dinger | |
| 6,610,066 B2 | 8/2003 | Dinger | |
| 6,635,060 B2 | 10/2003 | Hanson | |
| 6,751,875 B2 | 6/2004 | Jones | |
| 6,827,725 B2 | 12/2004 | Batchelor et al. | |
| 7,070,604 B1 | 7/2006 | Garito | |
| 7,226,459 B2 | 6/2007 | Cesarini | |
| 7,390,330 B2 | 6/2008 | Harp | |
| 7,510,563 B2 | 3/2009 | Cesarini | |
| 7,569,057 B2 | 8/2009 | Liu | |
| 7,666,186 B2 | 2/2010 | Harp | |
| 7,837,700 B2 | 11/2010 | Harp | |
| 7,883,476 B2 | 2/2011 | Miller | |
| 7,922,737 B1 | 4/2011 | Cesarini | |
| 2001/0037114 A1 | 11/2001 | Dinger | |
| 2001/0039427 A1 | 11/2001 | Dinger et al. | |
| 2004/0049217 A1 | 3/2004 | Ross | |
| 2005/0065529 A1 * | 3/2005 | Liu et al. | 606/79 |
| 2006/0026117 A1 | 2/2006 | Raman et al. | |
| 2006/0058732 A1 | 3/2006 | Harp | |
| 2006/0079919 A1 | 4/2006 | Harp | |
| 2006/0089633 A1 | 4/2006 | Bleich et al. | |
| 2006/0108342 A1 | 5/2006 | Samodell et al. | |
| 2006/0129159 A1 | 6/2006 | Lee | |
| 2006/0129160 A1 | 6/2006 | Liu et al. | |
| 2006/0161189 A1 | 7/2006 | Harp | |
| 2006/0200153 A1 | 9/2006 | Harp | |
| 2006/0200154 A1 | 9/2006 | Harp | |
| 2006/0200155 A1 | 9/2006 | Harp | |
| 2006/0224160 A1 * | 10/2006 | Trieu et al. | 606/83 |
| 2006/0259055 A1 | 11/2006 | Thorne | |
| 2007/0016238 A1 | 1/2007 | Marietta | |
| 2007/0021766 A1 | 1/2007 | Belagali | |
| 2007/0208353 A1 | 9/2007 | Shadduck | |
| 2008/0021487 A1 | 1/2008 | Heisler | |
| 2008/0047143 A1 | 2/2008 | Quan | |
| 2008/0058820 A1 | 3/2008 | Harp | |
| 2008/0103446 A1 | 5/2008 | Salstrom | |
| 2009/0177202 A1 | 7/2009 | May | |

FOREIGN PATENT DOCUMENTS

| | | |
|---|---|---|
| WO | WO03037194 | 5/2003 |
| WO | WO03053278 | 7/2003 |
| WO | WO2004002331 | 1/2004 |
| WO | WO2004028351 | 4/2004 |
| WO | WO2005009213 | 2/2005 |
| WO | WO2005020826 | 3/2005 |
| WO | WO2006047598 | 5/2006 |
| WO | WO2009005458 | 1/2009 |

OTHER PUBLICATIONS http://www.depuymitekfms.com/products/shavers FMS (DePuy MItek, Inc) Shavers and Burrs.
https://www.arthrex.com/innovations/top-left.cfm?adid=27 Arthrex CoolCut, Sabertooth and Excaliber, Clearcut (Burrs).
http://www.conmed.com/products_power_react.php Conmed React, Great White, Gator, Full Radius Resector, Cuda, Tiger (Burrs).
http://www.mdmmedical.com/shaver_blades_burs.tml MDM Medical; Shavers and Burrs (UK).
http://www.stryker.com/en-s/products/Endoscopy/ Arthroscopy?AccessoriesDisposables/CuttersandBurs/index.htm Stryker; Cutters and Burrs.
http://www.comeg.de/eng/pages/produkte/med_arthrokopie.htm Comeg: Shavers.
http://syedsurgical.com/rhinologyl.htm SYED Surgical: Rasps
http://www.microaire.com/kommerce_productdata. aspx?class=117 MicroAire; Rasps
Arthrex; Product Brochure, 2008 pp. 1-2.
Arthronet; Product Brochure, Cat_D_R00 / Seite 1-15.
ConMed; Product Brochure, CBR 0030 Rev.4 Jun. 2008 pp. 1.
ConMed; Product Brochure, CCA 9030 Dec. 2006 pp. 1-102.
Fiegert Endotech; Product Catalog, E11/07 pp. ACC 31.
Gimmi Endoscopic Technology; Product Catalog pp. 1-64 170/01 MKMC.

(56) References Cited

OTHER PUBLICATIONS

ConMed Linvatec; ReAct Shaver, Product Brochure, Sep. 2008 CBR 0038 pp. 1-2.
Arthroskopie Arthrocopy; REMA shaver Blades, Product Brochure.
http:www.therhinoplastycenter.com/poweredrasp.html, May 20, 2009 pp. 1-4, The Rhinoplasty Center.
Vokurka, J.; Shaver (Micro Debridor) in Otorhinolarynoglogy, International Congress Series 1240 (2003) 1411-1415.
ConMed Linvetec Product Catalog 6 2007 Rasp.
Eberle Shaver Operating instructions.
Tekno Catalog.
Arthrex com myarthrex brochures 2008.

PCT International Search Report and Written Opinion for related Application No. PCT/US2010/032081, mailed Feb. 1, 2011.
PCT International Preliminary Report on Patentability for related Application No. PCT/US2010/032081, mailed Apr. 5, 2012.
PCT International Search Report and Written Opinion for related Application No. PCT/US2011/035537, mailed Jul. 12, 2011.
PCT International Preliminary Report on Patentability for related Application No. PCT/US2011/035537, mailed Nov. 22, 2012.
PCT International Search Report and Written Opinion for related Application No. PCT/US2011/051415, mailed Mar. 13, 2012.
PCT International Preliminary Report on Patentability for related Application No. PCT/US2011/051415, mailed Mar. 28, 2013.

* cited by examiner

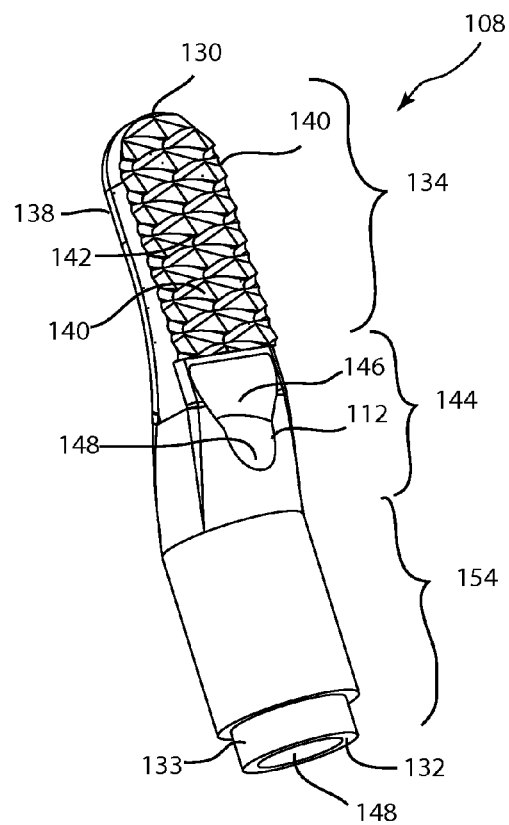
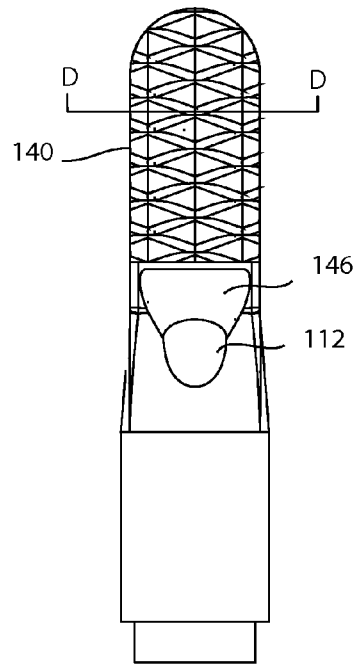
Fig. 3A  Fig. 3B
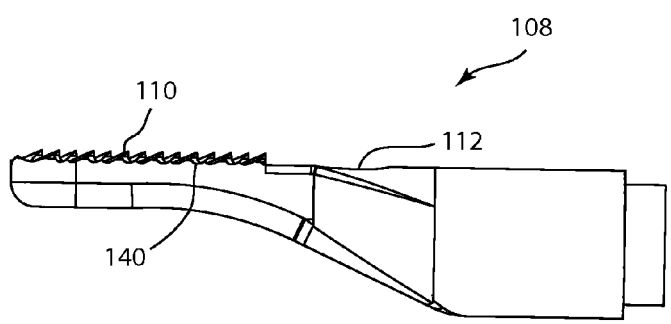
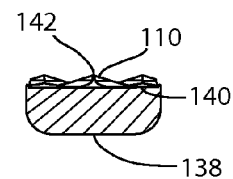
Fig. 3C  Fig. 3D

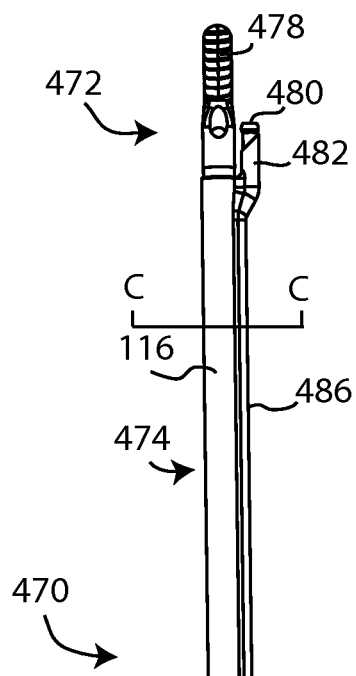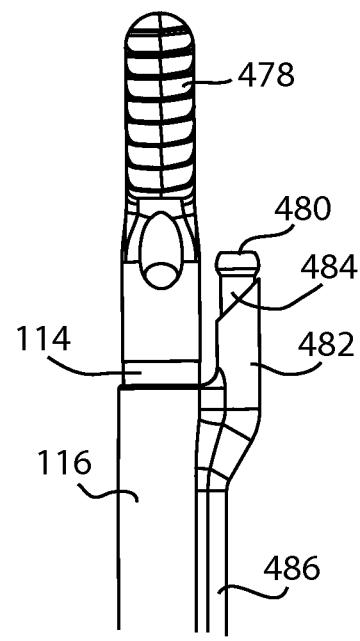
Fig. 25B
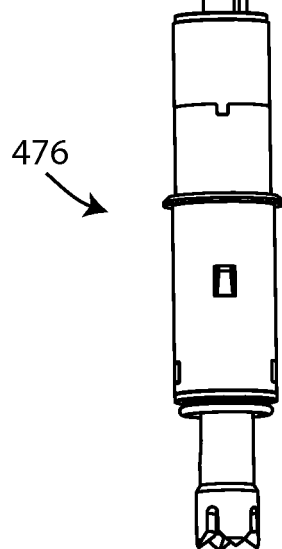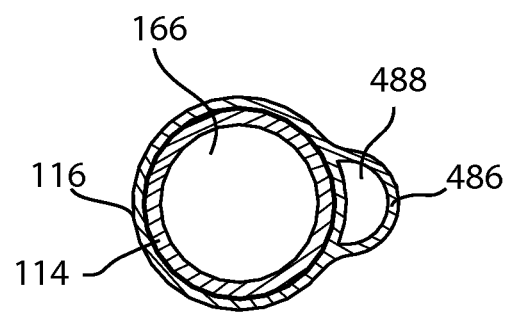
Fig. 25C
Fig. 25A

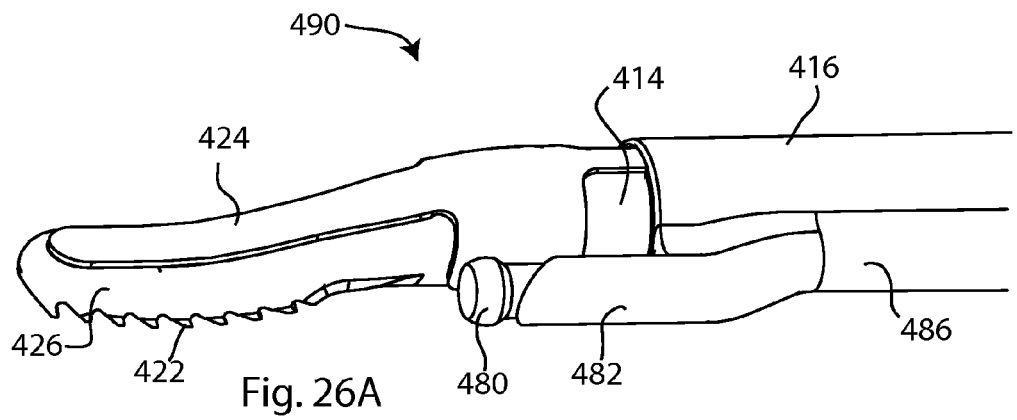
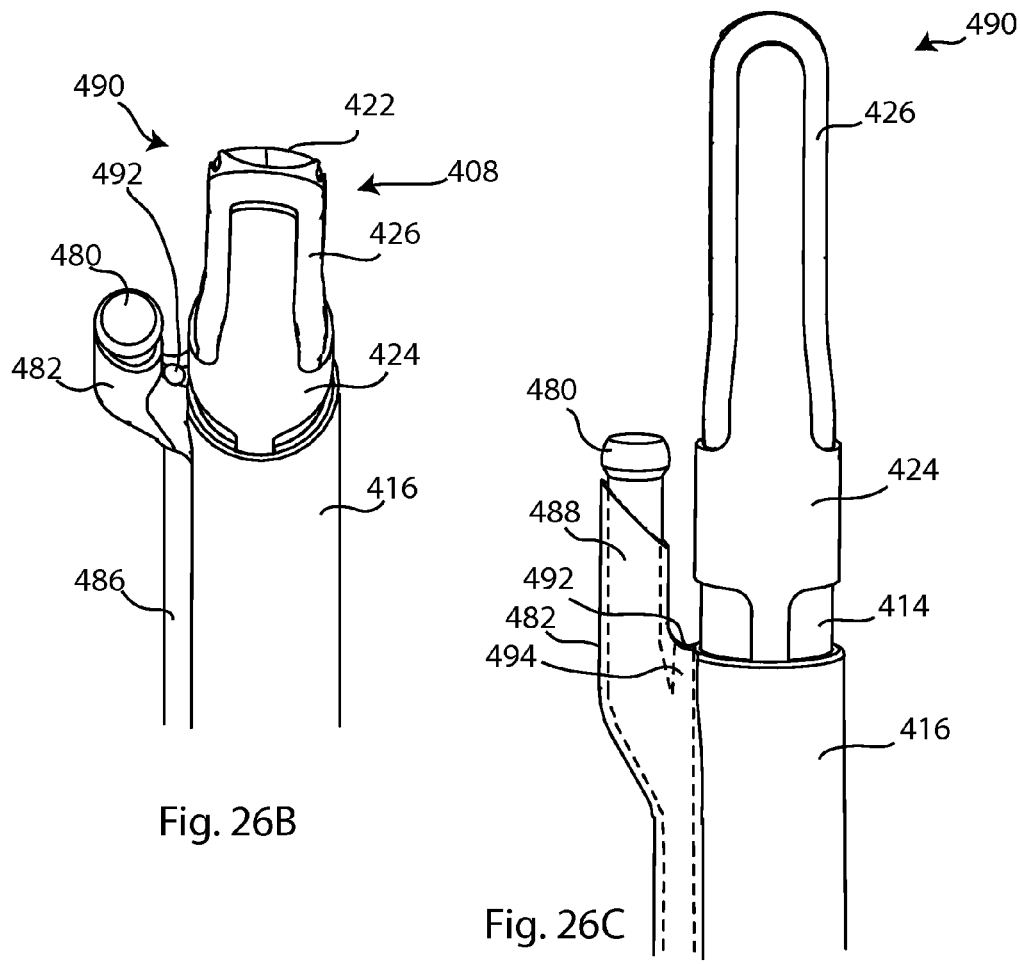

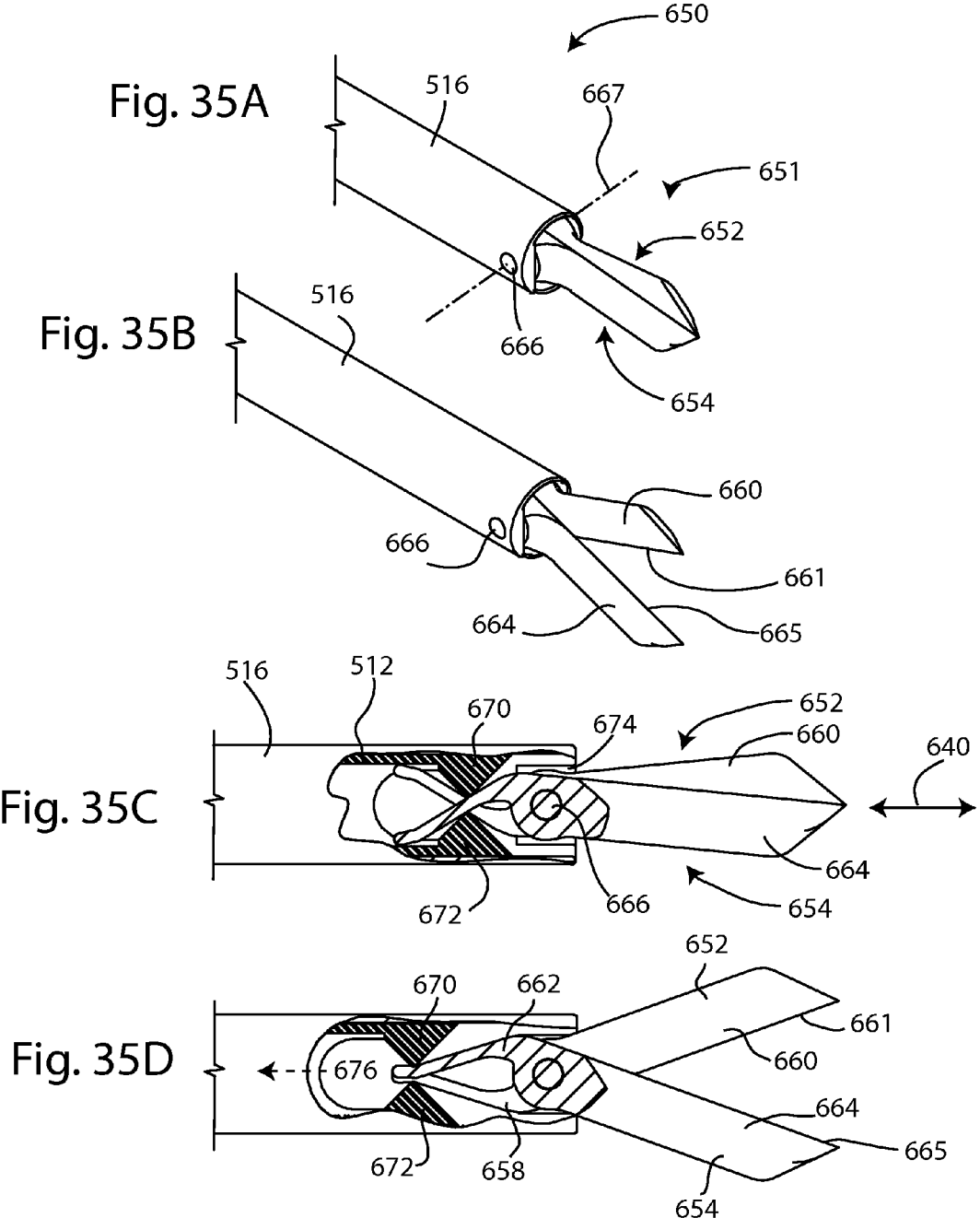

RECIPROCATING SURGICAL INSTRUMENTS

CROSS-REFERENCE TO RELATED APPLICATIONS

This application is a continuation-in-part of:

pending U.S. Application No. 13/102,351, filed May 6, 2011, entitled SURGICAL RASP WITH RADIOFREQUENCY ABLATION, which is a continuation-in-part of:

pending U.S. application Ser. No. 12/765,451, filed Apr. 22, 2010, entitled SURGICAL RASPING SYSTEMS AND METHODS, which is a non-provisional of:

U.S. Provisional Patent Application No. 61/245,487, filed Sep. 24, 2009, entitled SURGICAL RASPING SYSTEM.

U.S. Application No. 13/102,351 is also a non-provisional of:

U.S. Provisional Patent Application No. 61/332,308, filed May 7, 2010, entitled RECIPROCATING RASP WITH RF ABLATION PROBE; and pending U.S. Provisional Patent Application No. 61/382,795, filed Sep. 14, 2010, entitled RECIPROCATING SURGICAL INSTRUMENTS WITH ADDED FUNCTIONALITY.

This application is also a non-provisional of:

pending U.S. Provisional Patent Application No. 61/382,790, filed Sep. 14, 2010, entitled RECIPROCATING SURGICAL INSTRUMENTS WITH OPPOSING JAWS.

The above-identified documents are hereby incorporated by reference in their entirety.

FIELD OF THE INVENTION

This invention relates to surgical tissue removal devices by which anatomical tissues may be cut and removed from a joint or other operative site. Specifically, this disclosure relates to instruments having reciprocating motion and suction.

BACKGROUND OF THE INVENTION

Surgical procedures including subacromial decompression, arthroscopic resection of the acromioclavicular joint (also known as the Mumford procedure), and anterior cruciate ligament reconstruction involving notchplasty, may all necessitate removal of osteophytes. Other conditions such as chondromalacia and osteochondritis dissecans may call for removal of osteophytes or chondrocytes. It is known to use shavers and burrs having rotational cutting surfaces to remove these hard tissues. However, the round cutting surface of a shaver or bun system is not advantageous to creating or preparing a flat surface. The forces applied while using a rotational round cutting surface tend to pull the cutting end to either side by a moment force pivoting on the hand making precise control difficult. Working in confined spaces may exacerbate these issues, as adjacent soft tissues may easily be grabbed by a rotating cutting surface.

An instrument with a reciprocating, instead of rotary, cutting end may provide a surgeon with greater control over the instrument and enhanced ability selectively remove targeted tissues, especially in confined areas and/or during arthroscopic procedures. One type of reciprocating instrument may include cutting ends with rasping surfaces for preparation of flat joint surfaces. Another type of reciprocating instrument may include cutting ends with opposing jaws which provide biting action for trimming of unwanted tissue.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 3A in an enlarged isometric view of a rasp head of the rasping system of FIG. 1A; FIG. 3B is a front view of the rasp head of FIG. 3A; FIG. 3C is a side view of the rasp head of FIG. 3C; FIG. 3D is a cross-sectional view of the rasp head of FIG. 3A taken along section line D-D;

FIG. 5C is a bottom end view of the outer housing of FIG. 5A;

FIG. 25A is a bottom view of a reciprocating rasp device including an auxiliary device; FIG. 25B is an enlarged view of a head portion of the device of FIG. 25A; FIG. 25C is a cross-sectional view of a shaft portion of the device of FIG. 25A taken along line C-C;

FIG. 26A is a top isometric view of a reciprocating rasp device including an auxiliary device, RF ablation system, and an infusion system; FIG. 26B is a top view of the device of FIG. 26A, FIG. 26C is a side isometric view of the device of FIG. 26A;

FIG. 35A is an isometric view of a distal portion of a tissue removal member with a cutting head having opposing jaws, the jaws in a closed position; FIG. 35B is an isometric view of the tissue removal member of FIG. 35A with the jaws in an open position; FIG. 35C is a partial side cross-sectional view of the cutting head of FIG. 35A; FIG. 35D is a partial cross-sectional view of the cutting head of FIG. 35B;

DETAILED DESCRIPTION OF THE PREFERRED EMBODIMENTS

The present disclosure relates to tissue removal devices and methods by which body tissues may be cut and removed during surgery. Those of skill in the art will recognize that the following description is merely illustrative of the principles of the disclosure, which may be applied in various ways to provide many different alternative embodiments. This description is made for the purpose of illustrating the general principles of this invention and is not meant to limit the inventive concepts in the appended claims.

The present disclosure provides rasping systems that are shaped to be functional in multiple orthopedic surgery applications, including but not limited to shoulder, knee, hip, wrist, ankle, spinal, or other joint procedures. The system comprises a rasping head which may be low profile and offer a flat cutting/rasping surface, and is configured to be driven by an attached hub that will translate a rotational movement into a reciprocating motion. Suction for removal of bone fragments or other tissues may be provided through an opening in or adjacent the rasping head. In other embodiments, the system comprises a cutting head with opposing jaw members, including at least one movable jaw. The reciprocating motion urges the jaw members to move between open and closed positions to provide biting, nipping or scissoring action.

This device provides an alternative method of removing hard tissue to the currently used shavers and burrs that offer a rotational cutting surface. By applying a reciprocating flat cutting surface the surgeon has greater control over the instrument and is better able to create/prepare a flat surface. The reciprocating force of the rasp applies resisting pressure to the surgeons hand in the axial direction with the hand, making control much easier. Increased control will result in a decrease in injury to the surrounding soft tissue. The rasp also has a lower profile than many of the existing shaver systems allowing access to tight joints without damaging surrounding tissues. The teeth of the rasp may be positioned such that the cut material will be pulled towards the suction pathway to more efficiently remove debris from the surgical site, thus decreasing the duration of a procedure.

Figure 1A:
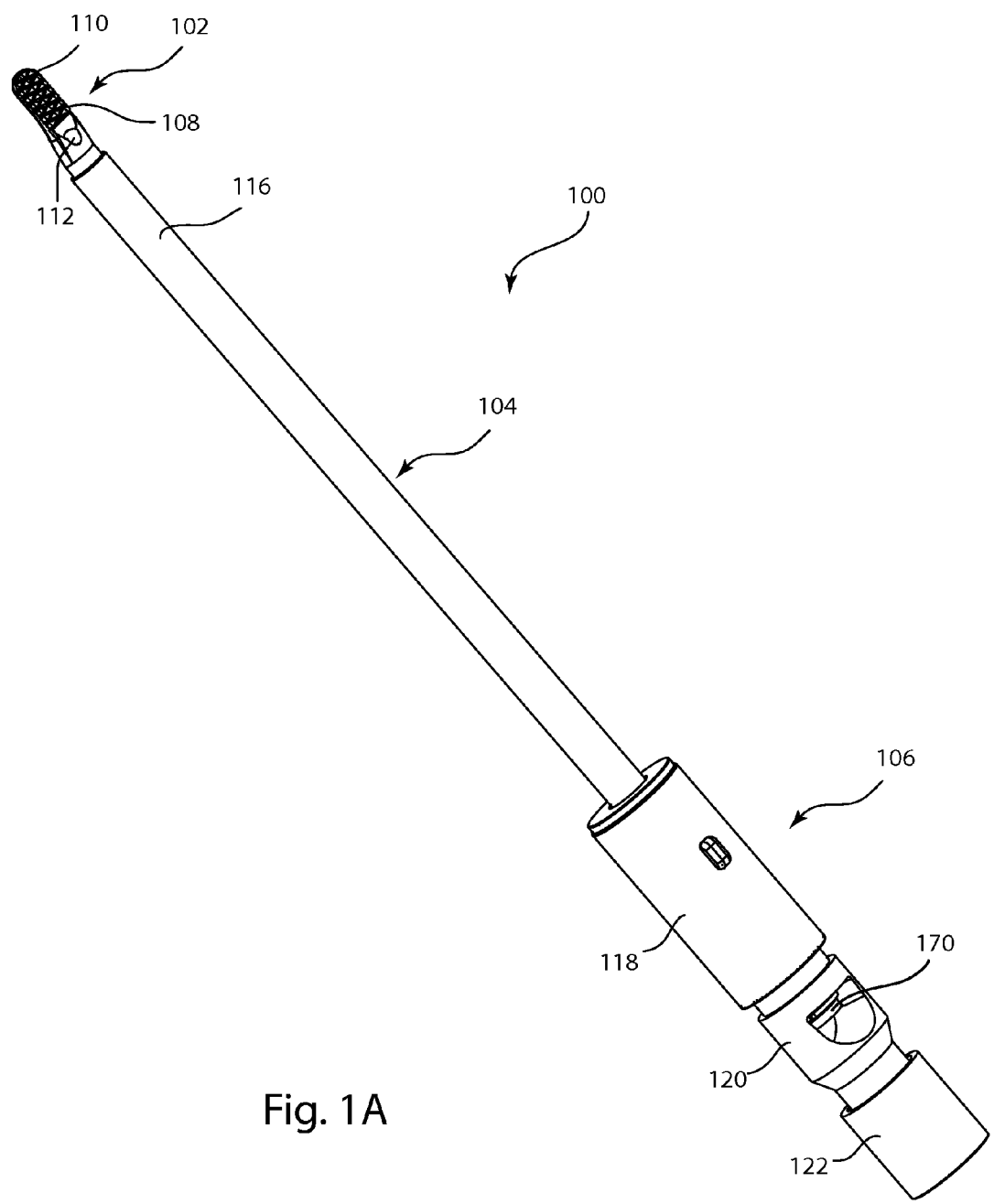
FIG. 1A is an isometric view of a reciprocating rasping system.

Referring to FIG. 1A, rasp system 100 is shown in an isometric view. Rasp system 100 comprises head portion 102, shaft portion 104, and handle portion 106. Head portion 102 comprises rasp head 108, which includes a plurality of teeth 110 or cutting edges which may cut anatomical tissues when drawn along the tissue surface. The teeth may be particularly suited for cutting or removing hard tissues such as bone or cartilage. A suction opening 112 is located on the head portion 102, and may be disposed between the teeth and the shaft portion. The shaft portion 104 comprises inner shaft 114 (not visible in FIG. 1A) which extends proximally from the rasp head 108 and is received in the handle portion 106. The inner shaft 114 extends through an optional outer sleeve 116 which is joined to the handle portion 106. At its proximal end, inner shaft 114 is received within a shaft key 170 (not visible in FIG. 1A).

Handle portion 106 includes an outer housing 118, a driving hub 120, and a spring collet 122 which houses a spring 250 (not visible in FIG. 1). Outer housing 118 comprises a cam surface (not visible in FIG. 1) which is complementarily shaped to a cam follower surface on driving hub 120. When handle portion 106 is engaged in a powered rotary handpiece and power is supplied, hub 120 rotates, and the cam and cam follower surfaces provide a motion conversion mechanism which converts the rotary motion of the hub to axial reciprocal motion of the inner shaft 114 and attached head 108. Rasp system 100 is connectable via spring collet 122 to a powered handpiece, to provide rotary power to the rasp system, and to provide suction. Suitable handpieces include the Linvatec Advantage Shaver (Ref D9824) or another similar system known in the art.

Figure 1B:
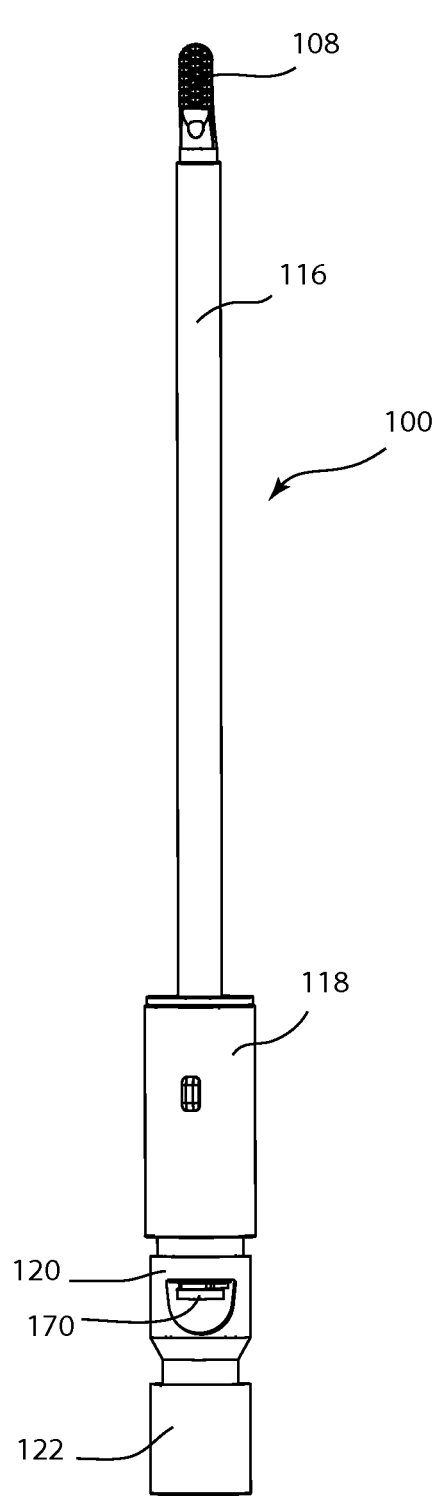
FIG. 1B is a front view of the rasping system of FIG. 1A in a retracted configuration.
Figure 1C:
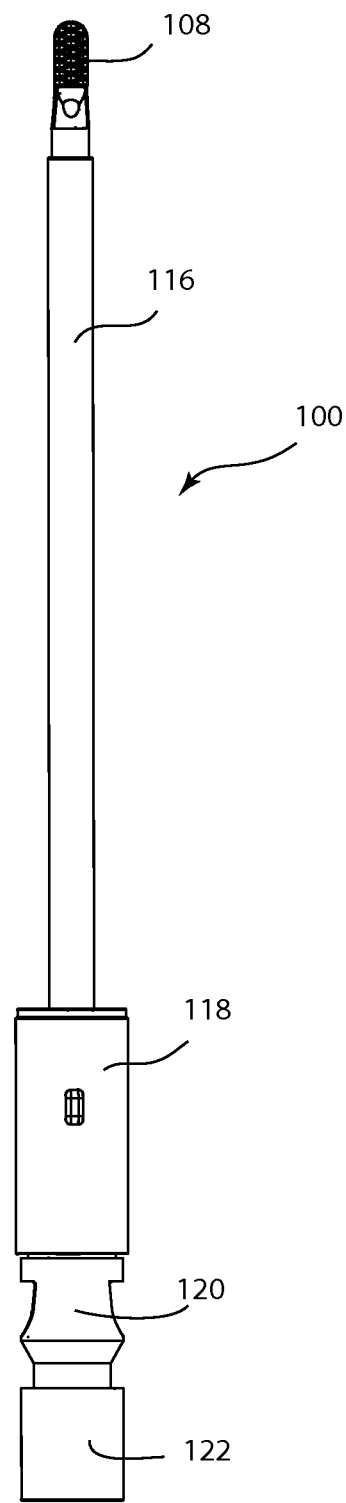
FIG. 1C is a front view of the rasping system of FIG. 1A in an extended configuration.

FIG. 1B illustrates rasp system 100 in a retracted configuration. In this configuration, the shaft key 170, inner shaft 114 (not visible; within outer sleeve 116) and rasp head 108 have been pulled by interaction of the cam and cam follower surfaces to a proximal position. FIG. 1C illustrates rasp system 100 in an extended configuration. In this configuration, driving hub 120 has rotated relative to the outer housing 120; and the shaft key, inner shaft 114 and rasp head 108 have been reciprocally translated to a distal position by the spring bias of spring 250. It is appreciated that an alternate embodiment of the invention may include a curved inner shaft and, optionally, a curved outer sleeve. In the curved embodiment the rasp head may be angled relative to the inner shaft, and the outer sleeve may be sized to allow free reciprocation of the inner shaft.

Figure 2:
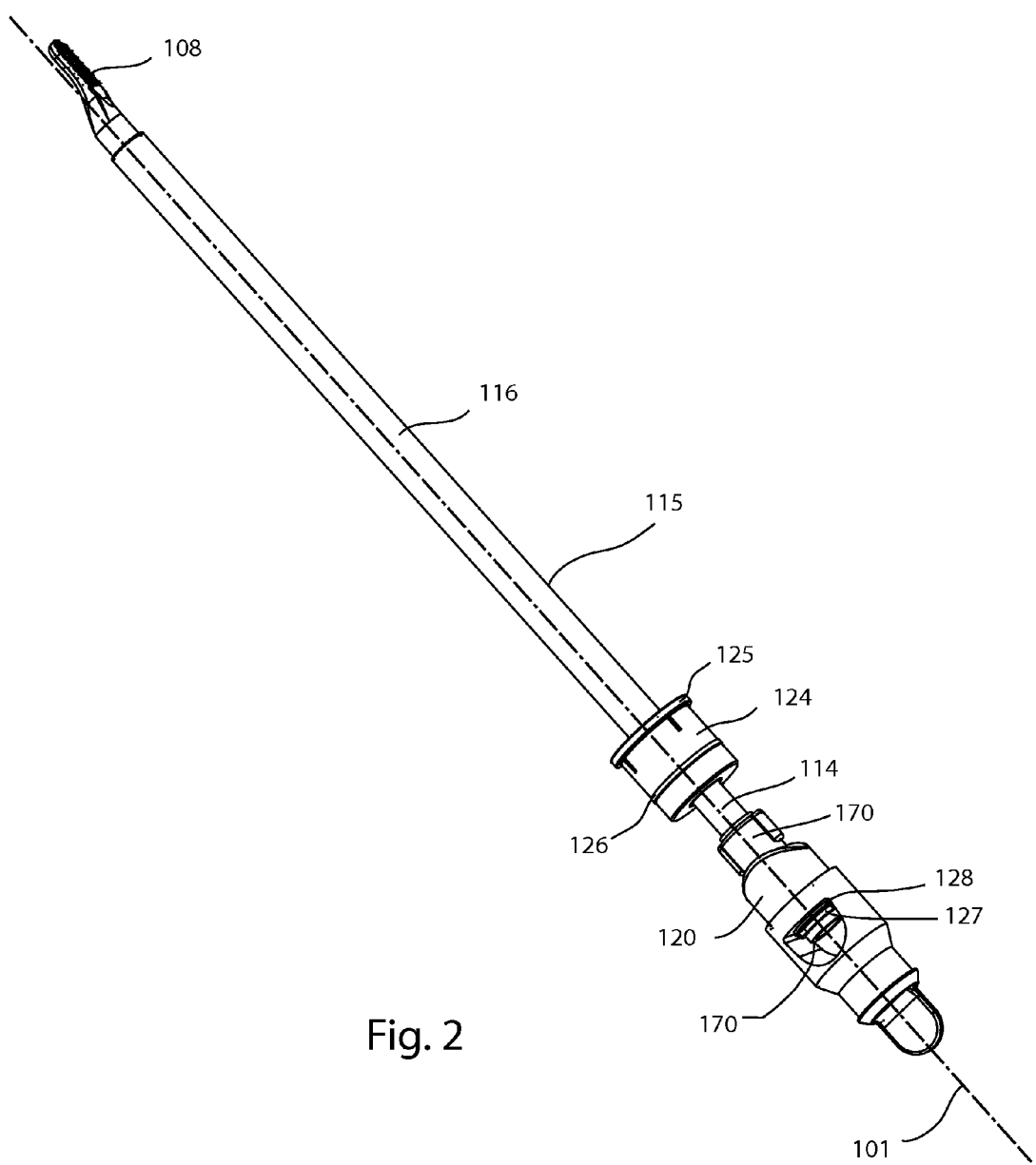
FIG. 2 is an isometric view of the rasping system of FIG. 1A with an outer housing and collet removed, and a longitudinal axis of the rasping system.

FIG. 2 illustrates rasp system 100 minus the outer housing 118 and spring collet 122. Outer sleeve 116 is joined to plug 124. Plug 124 comprises a rim 125 and a protruding ring 126. When received within the outer housing 118 as in FIG. 1, ring 126 may provide a snap connection with a groove feature within outer housing 118, and rim 125 may seat against a distal end of the outer housing. Once joined with the outer housing 118, plug 124 and outer sleeve do not translate or rotate relative to the outer housing. The outer sleeve 116 provides protection to surrounding tissues when rasp system 100 is used; outer sleeve 116 does not rotate or reciprocate, yet allows reciprocal movement of inner shaft 114 within. Space between the inner shaft 114 and the outer sleeve 116 may optionally be lubricated. Together, the rasp head 108, inner shaft 114 and shaft key 170 comprise a tissue removal member 115.

Proximal to the plug 124, the inner shaft 114 is received in the shaft key 170 and is non-movable relative to the shaft key. A portion of shaft key 170 is received within a portion of hub 120, which is rotatable about the shaft key. A snap ring 127 is received in a groove formed at the proximal end of the shaft key, and retains the shaft key 170 within the hub 120 while still allowing the hub 120 to rotate about the shaft key. A washer 128 is positioned around the shaft key 170 between the snap ring 127 and the hub 120. The system 100 comprises a longitudinal axis 101 about which the hub 120 rotates, and along which the tissue removal member 115 is reciprocally translated.

Referring to FIGS. 3A through 3D, several views of rasp head 108 are shown. Rasp head 108 comprises a distal end 130, and a proximal end 132, and further comprises a working portion 134, a head transition portion 144 and a head shaft portion 154. The working portion 134 comprises a first side 136 which may be also be known as a front side, and a second, or back side 138 opposite the first side. A tissue removal surface 140 is disposed on the first side 136, although it is appreciated that in alternate embodiments, the tissue removal surface may be disposed on the back side, or on both the front and back sides. The tissue removal surface 140, may be flat as in FIGS. 3A-3D, or in other embodiments may be concave or convex. The plurality of teeth 110 populates the tissue removal surface, each tooth having a cutting portion 142. The cutting portion 142 may be a point as seen in the teeth depicted in FIGS. 2A-2D, but in other embodiments the cutting portion may be an edge, or a combination of one or more edges and a point. The teeth may be distributed individually; in even ranks or rows; or in alternate ranks or rows. In alternative embodiments of the cutting head, the number, size, and distribution of the teeth may vary to provide a variety of tissue cutting surfaces suitable for different tissue removal procedures. The cutting portions 142 may be uni-directionally oriented as in FIGS. 3A-3D, meaning that all of the teeth point the same direction. Advantageously, the teeth may be pointed toward the suction opening 112, thus facilitating efficient movement of cut debris into the suction opening. Another feature of uni-directional teeth is that the teeth may only cut into tissue when the rasp head is moved in one direction; for example if the teeth are pointed proximally, cutting will occur when the rasp head is translated proximally.

The transition portion 144 extends between the working portion and the head shaft portion, and may be angled relative to the working and/or head shaft portions. Proximal to and spaced apart from the tissue removal surface, the suction opening 112 provides a distal opening to a suction pathway. A fan-like scoop portion 146 adjacent the suction opening 112 may funnel excised tissue toward the suction opening. A head suction bore 148 extends proximally from the suction opening 112, forming a portion of the suction pathway.

The head shaft portion 154 extends from the transition portion 144 to the proximal end 132 of the rasp head 108. At the proximal end 132, a fitting or connection feature 133 allows for joining of the rasp head 108 to the inner shaft 114. The head suction bore 148 terminates at the proximal end 132, but the suction pathway continues through the hollow inner shaft 114. The rasp head 108 may be removably joined to the inner shaft via a press fit or mechanical fit, or may be permanently joined via a weld or other permanent connection.

Figures 4A, 4B:
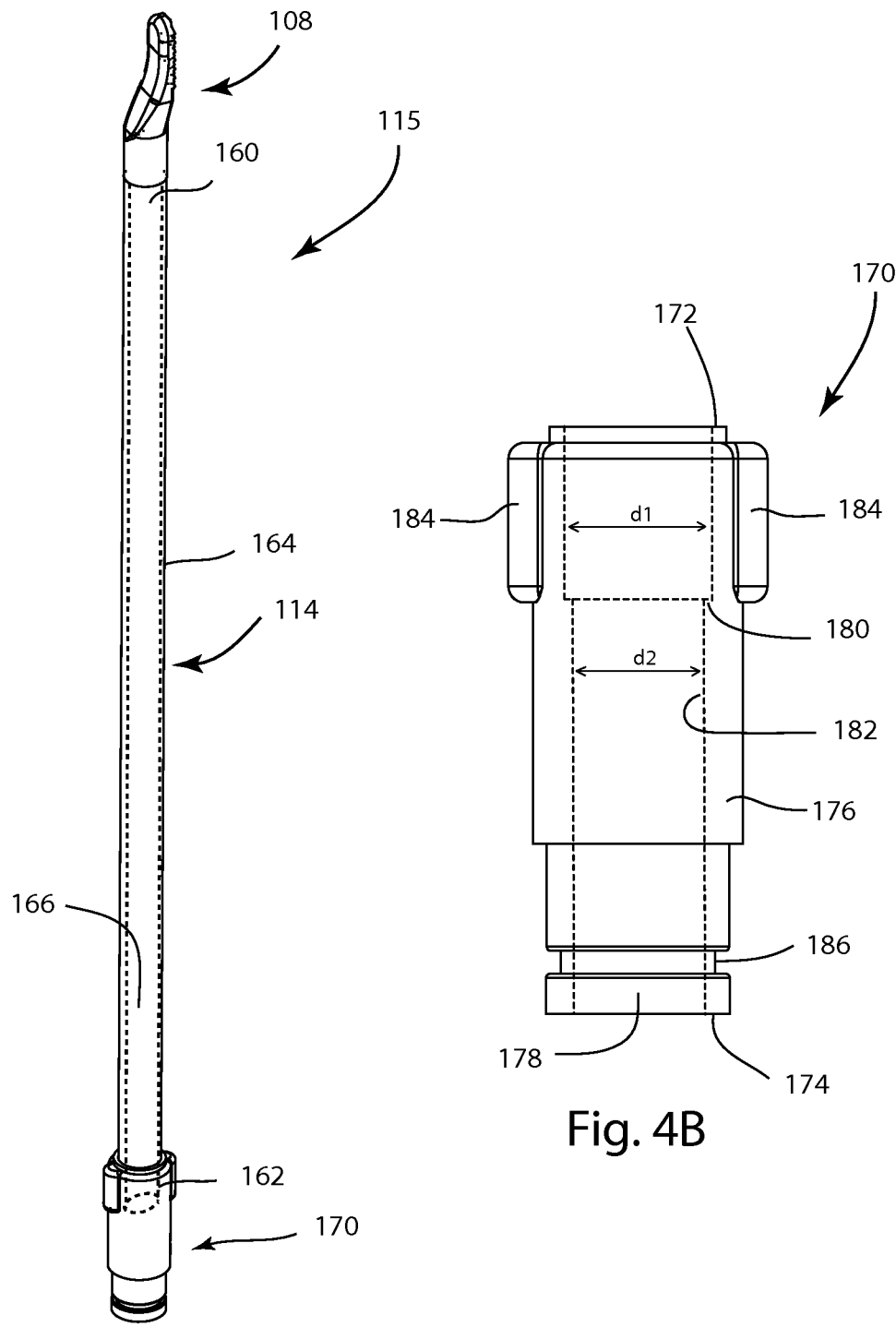
FIG. 4A is a iso-side view of a tissue removal member of the rasping system of FIG. 1A.
FIG. 4B is an enlarged side view of a shaft key of the tissue removal member of FIG. 4A.

FIG. 4A illustrates the rasp head 108, inner shaft 114, and a shaft key 170, which together comprise the tissue removal member 115. The inner shaft 114 comprises a tubular member having a distal end 160, a proximal end 162 and an inner shaft body 164 extending therebetween. The inner shaft body defines an inner shaft bore 166, indicated by dashed lines, extending from the distal end to the proximal end, forming a portion of the suction pathway. The proximal end 162 of the inner shaft is received in the shaft key 170. Inner shaft 114 may be glued, welded, bonded, press fit or otherwise permanently joined to shaft key 170, so that no movement including translation or rotation between inner shaft 114 and shaft key 170 is allowed. Inner shaft 114 may be monolithically formed with shaft key 170.

Referring to FIG. 4B, shaft key 170 comprises a distal end 172, a proximal end 174, and generally cylindrical key body 176 extending therebetween. A key bore 178 (indicated by dashed lines) extends the length of the shaft key, and forms a portion of the suction pathway. At its distal end, the key bore has a first diameter d1 dimensioned to receive the proximal end of the inner shaft 114. Proximal to a shoulder 180 formed in an inner wall 182 of the key body 176, the key bore has a second diameter d2. Two individual wings 184 protrude from the key body 176, opposite from one another near the distal end 172. The wings 184 are shaped to be received in recesses formed within the outer housing, preventing rotation of the tissue removal member when the hub is rotated. It is appreciated that in other embodiments of the invention, the number and placement of the wings 184 may vary, or the wings may be formed on the outer housing, to be received in recesses formed on the shaft key 170. Toward the proximal end 174 of the shaft key 170, an annular groove 186 is formed on the outside of the key body 176. The groove 186 is shaped to receive snap ring 127. The suction pathway comprises the continuous pathway formed by head suction bore 148, inner shaft bore 166 and key bore 178.

Outer housing 118 is illustrated in FIGS. 5A through 5D. The tissue removal member 115 is receivable in the outer housing, while the outer housing is shaped to be received in a powered handpiece. Outer housing 118 is generally cylindrical and comprises a distal end 190, a proximal end 192 and an outer housing body 194 extending therebetween. A tab 196 protrudes exteriorly from the outer housing body, and is shaped to be received in a groove formed in a powered handpiece, to both properly align the rasp system 100 within the handpiece and prohibit rotation of the outer housing 118 relative to the handpiece.

Figure 5A:
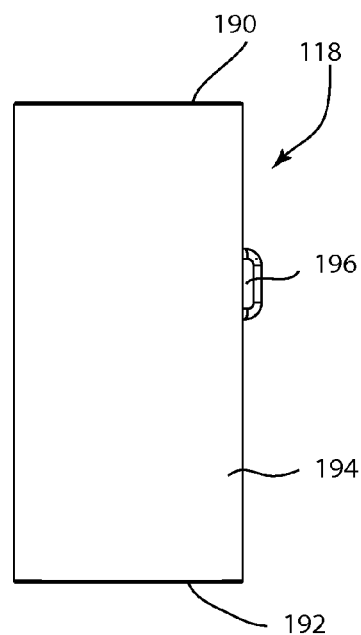
FIG. 5A is a side view of an outer housing of the rasping system of FIG. 1A.
Figure 5B:
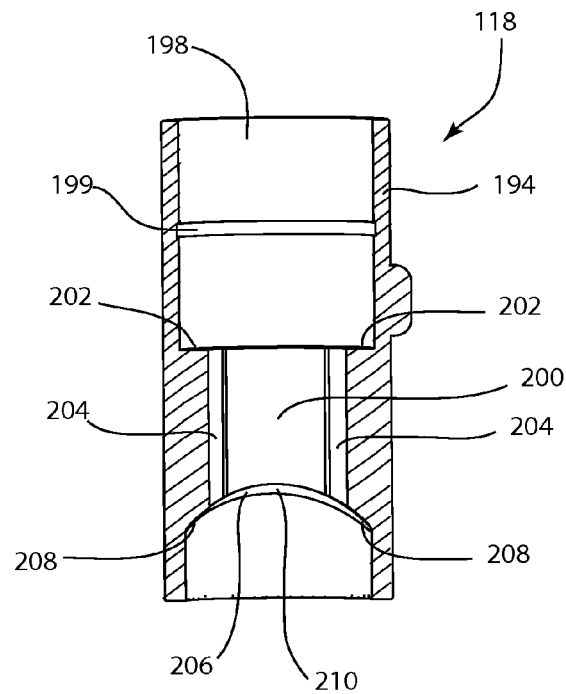
FIG. 5B is cross-sectional view of the outer housing of FIG. 5A, taken along line B-B of FIG. 5C.
Figure 5C:
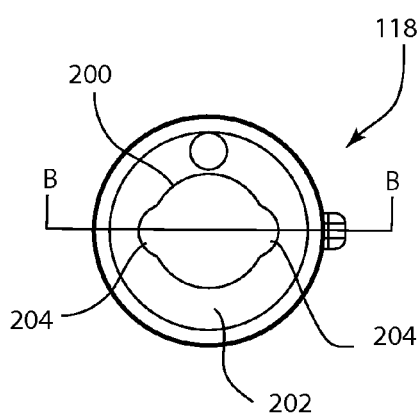
FIG. 5C is a top end view of the outer housing of FIG. 5A.

FIG. 5B is a longitudinal cross-sectional view of the housing, taken along line B in FIG. 5C. Extending longitudinally through the housing is housing bore 198. Toward the distal end of the housing, bore 198 is shaped to receive the generally cylindrical plug 124 (not shown) which in turn receives the outer sleeve 116. An annular inner groove 199 is shaped to fit around the ring 126 on the outer surface of the plug. An annular shoulder 202 is formed in the inner wall of the housing body 194. A keyway, or key portion 200 of the housing bore 198 is constricted, and shaped to receive a portion of the shaft key 170. Two recesses 204 in the key portion 200 are shaped to complementarily fit the wings 184 of the shaft key 170. When the shaft key 170 is received in the key portion 200 of the housing 118, the complementary fit of the wings 184 in the recesses 204 prohibits rotation of the shaft key 170, and thus tissue removal member 115, relative to the outer housing 118, but allows proximal-distal/distal-proximal translation of the shaft key 170 relative to the outer housing.

Figure 5D:
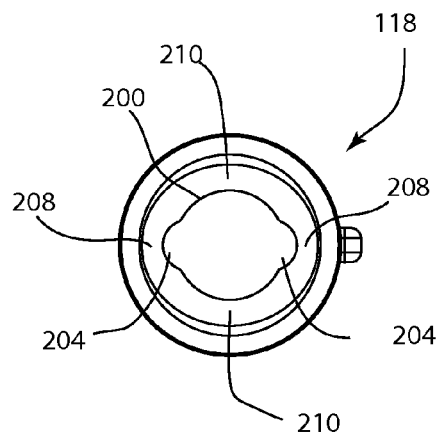

Referring to FIG. 5D, a bottom end view shows an undulating, annular cam surface 206 formed in the inner wall of the housing body 194. The annular cam surface 206 comprises two lobes 208, formed as two portions which protrude proximally, parallel to the longitudinal axis, on opposite sides of the bore 198 from one another. At the lobes 208, cam surface 206 slopes proximally from its outer diameter to its inner diameter. The lobes 208 are evenly interspersed with two hollows 210, such that, when viewed from the side, the annular cam surface 206 undulates evenly between two low points at the lobes 208, and two high points at the hollows 210.

Figure 6A:
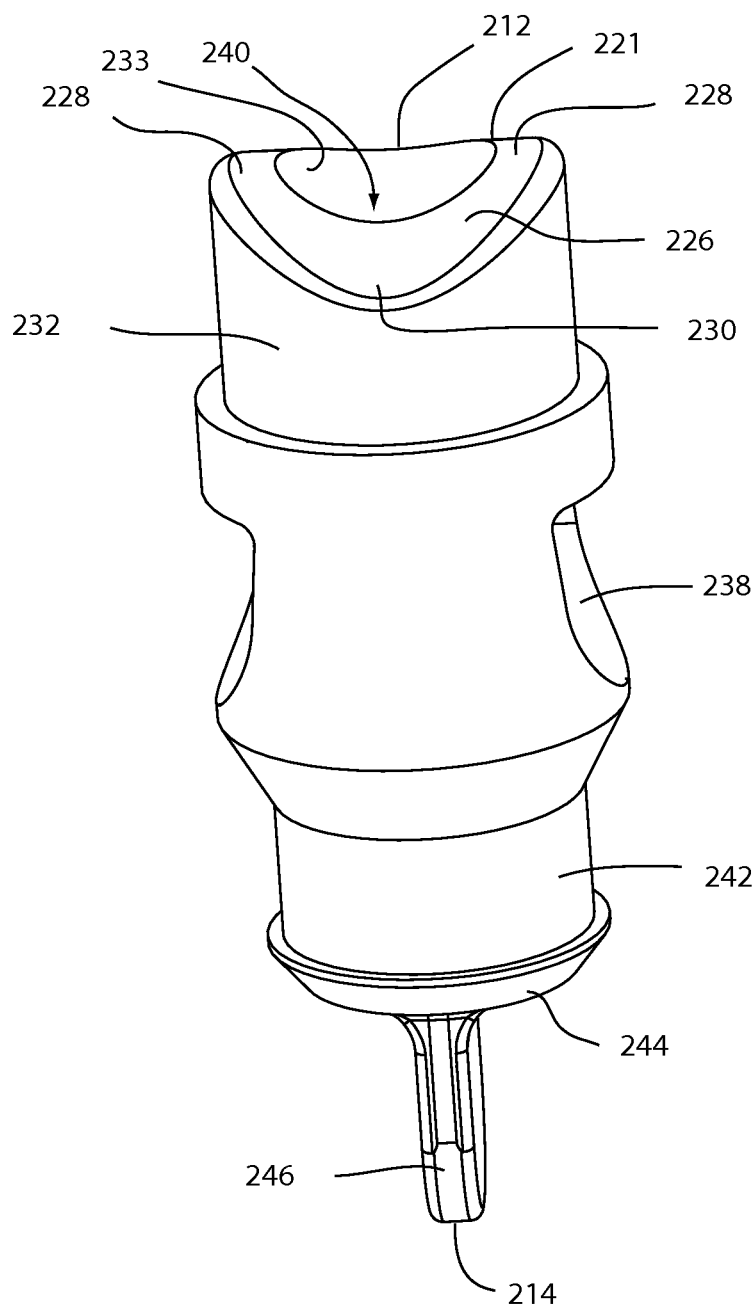
FIG. 6A is an isometric view of a first side of a driving hub of the rasping system of FIG. 1A.
Figure 6B:
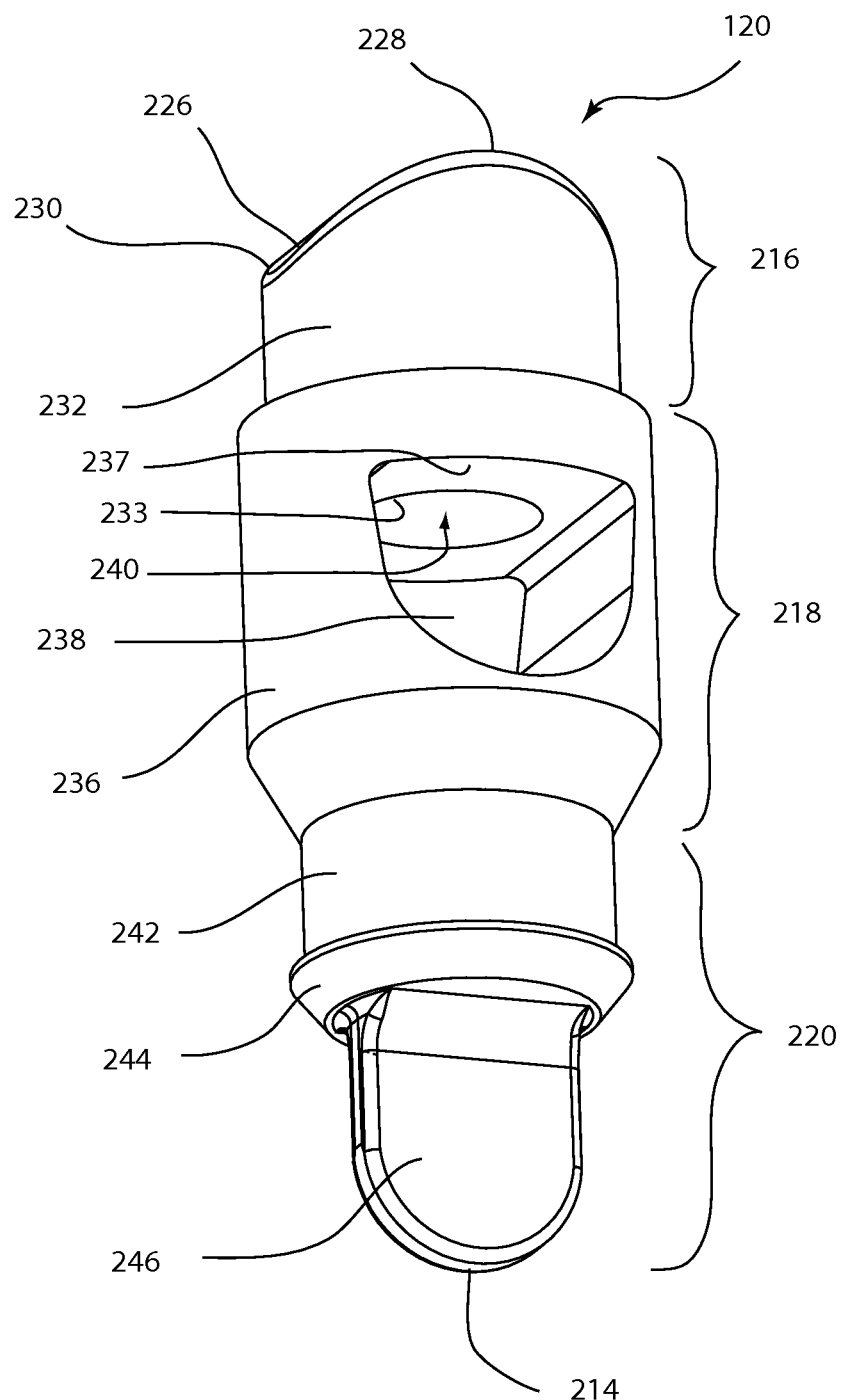
FIG. 6B is an isometric view of a second side of a driving hub of the rasping system of FIG. 1A.

The driving hub 120 is illustrated in FIGS. 6A and 6B. The hub 120 extends longitudinally between a distal end 212 and a proximal end 214. The hub 120 comprises three portions: a distal cam portion 216, an intermediate portion 218, and a proximal driving portion 220. At the distal end 212, the hub terminates in a distal end face 221 having a cam follower surface 226 which is shaped complementarily to the cam surface 206. The cam follower surface comprises two follower lobes 228 interspersed with two follower hollows 230. At the follower hollows 230, cam follower surface 226 slopes proximally from its outer diameter to its inner diameter. The follower lobes 228 are evenly interspersed with the follower hollows 230, such that, when viewed from the side, the cam follower surface 226 undulates evenly between two low points at the hollows 230, and two high points at the lobes 228. The distal cam portion 216 is circumscribed by an annular outer wall 232. A driving hub bore 240, lined by an annular inner wall 233, extends longitudinally through the distal cam portion 216.

The intermediate portion 218 of the hub 120 comprises an intermediate body 236, through which an aperture 238 extends transversely. The driving hub bore 240 continues longitudinally from the distal cam portion 216 and terminates at a proximal hub face 237, in communication with the aperture 238. The driving hub bore 240 forms the proximal portion of the suction pathway, which terminates as it opens into the aperture.

The driving portion 220 of the driving hub 120 provides a connection feature for connection to a powered handpiece. The driving portion 220 comprises a smooth, cylindrical hub body 242 which terminates at an annular flange 244. The flange 244 forms a lip extending exteriorly from the hub body. Proximal to the hub body and flange, a plate-like driving tab 246 projects longitudinally, and transversely across the diameter of the hub body. The driving tab 246 is shaped to be coupled with a driver in the powered handpiece, to provide rotational motion to the driving hub. It is appreciated that in other embodiments of the invention, the connection to the powered handpiece may take other forms, including but not limited to a square, star, cross, X-shape, H-shape, or other form compatible with the handpiece.

Figure 7A:
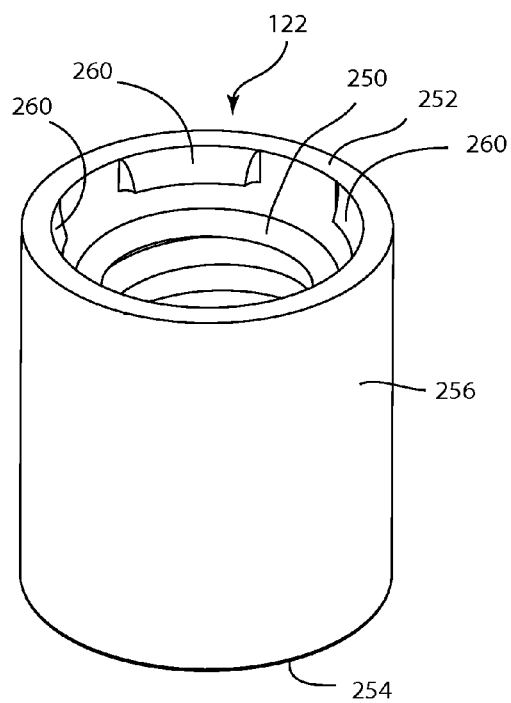
FIG. 7A is an isometric view of a spring collet and spring of the rasping system of FIG. 1A.
Figure 7B:
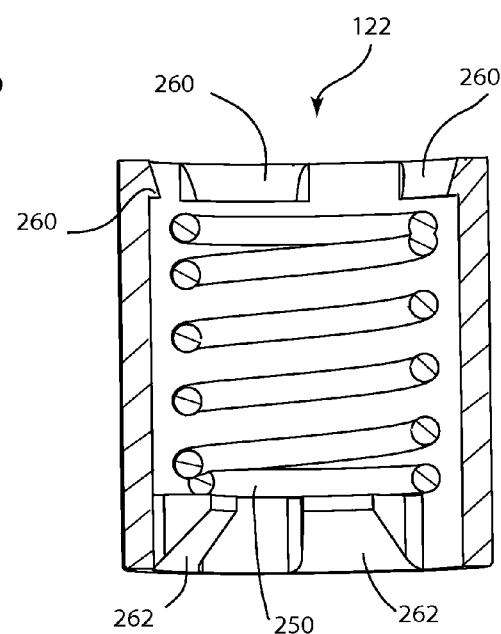
FIG. 7B is cross-sectional view of the spring collet and spring along section line B-B of FIG. 7C.
Figure 7C:
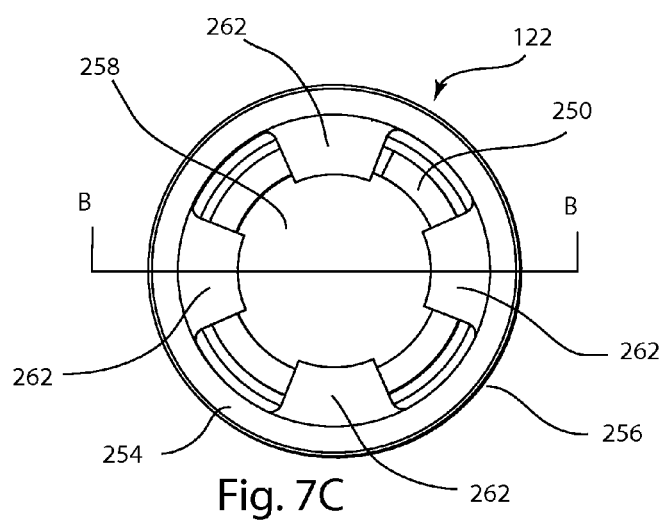
FIG. 7C is a bottom end view of the spring collet and spring of FIG. 7A.

Referring to FIGS. 7A through 7C, the spring collet 122 and a spring 250 are illustrated. Spring collet 122 is generally cylindrical and tubular in form, comprising a distal end 252, a proximal end 254, and a tubular collet body 256 extending therebetween. A collet bore 258 is defined and surrounded by the collet body 256. Adjacent the distal end 252, a plurality of distal stops 260 formed on the collet body 256 protrude inward into the collet bore 258. When the collet 122 is coupled with the driving hub 120, distal stops 260 cooperate with flange 244 to prevent the collet from becoming uncoupled yet allow rotation of the hub relative to the collet. Adjacent the proximal end 254, a plurality of proximal stops 262 formed on the collet body 256 protrude inward into the collet bore 258. As seen in FIG. 7B, the proximal stops may be larger than the distal stops, projecting farther into the collet bore. The proximal stops 262 prevent the spring 250 from escaping proximally out of the spring collet 122 and provide a platform against which the spring may be compressed. When coupled in collet 122 with driving hub 120, spring 250 is biased to push the driving hub 120 distally unless otherwise acted upon.

Figure 8:
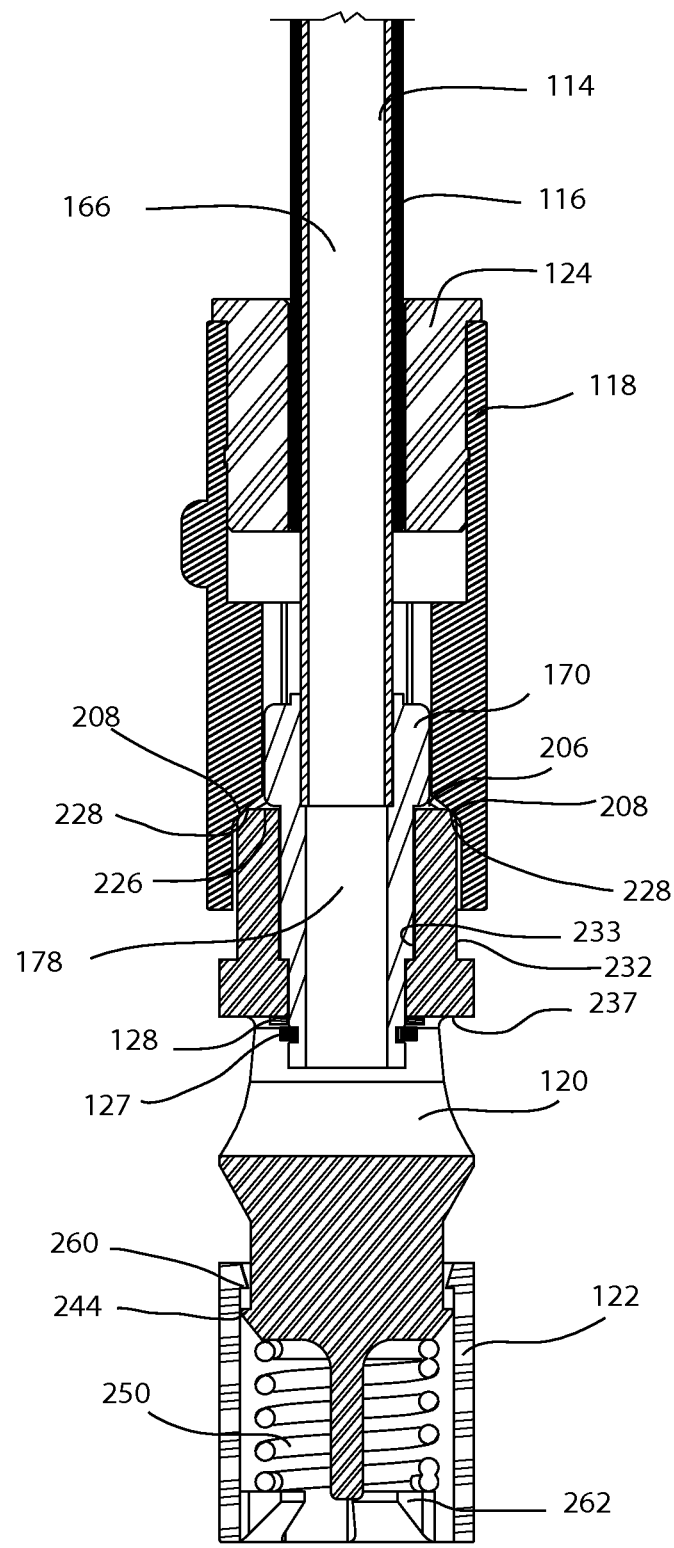
FIG. 8 is a longitudinal cross-sectional view of a handle portion and a segment of a shaft portion of the rasping system of FIG. 1A in the retracted position.
Figure 9:
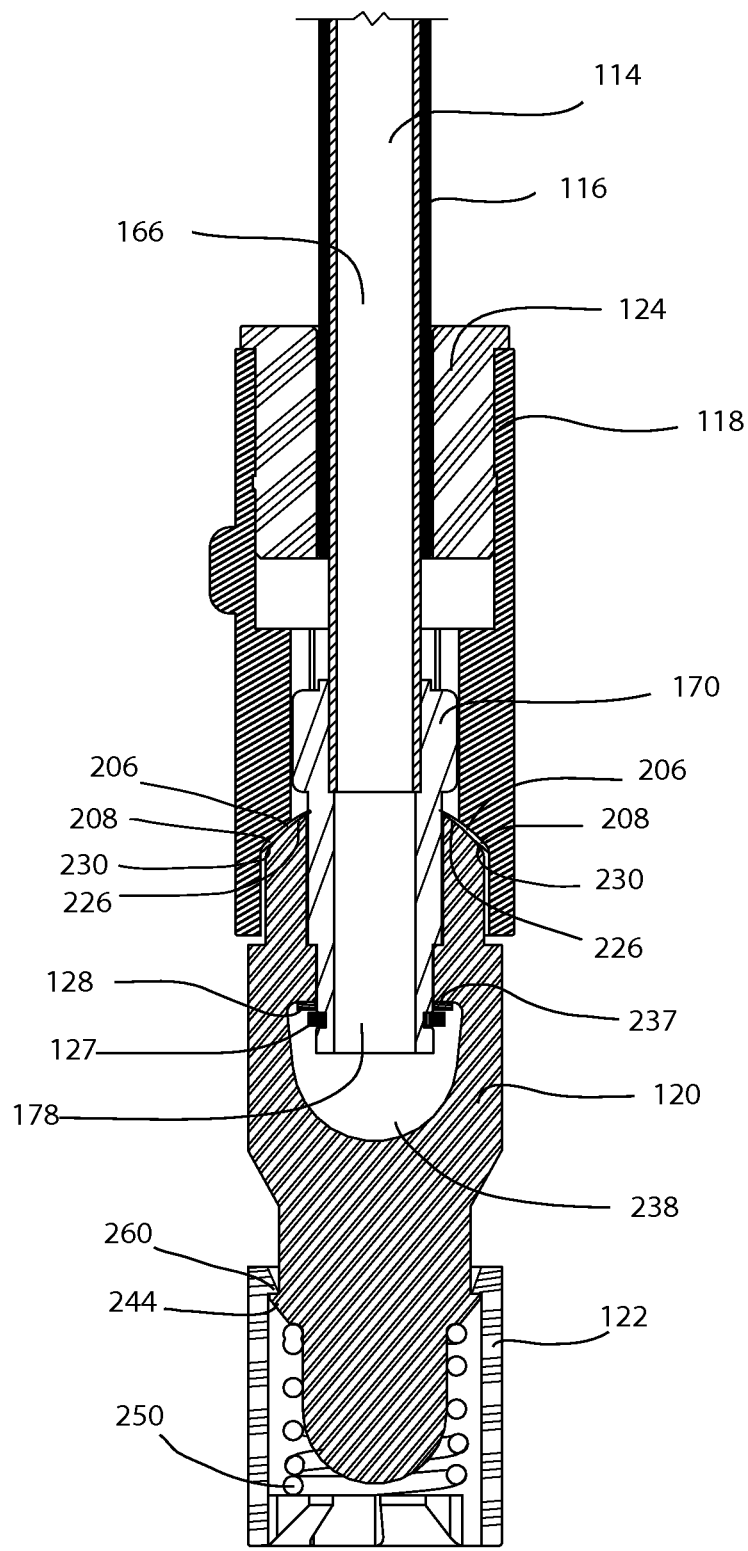
FIG. 9 is a longitudinal cross-sectional view of a handle portion and a segment of a shaft portion of the rasping system of FIG. 1A in the extended position.

FIGS. 8 and 9 provide cross-sectional views of the handle portion and a segment of the shaft portion of rasp system 100. FIG. 8 shows the rasp system 100 in a retracted configuration, in which the tissue removal member 115 comprising shaft key 170, inner shaft 114 and rasp head 108 is in a first position relative to the outer housing 118. FIG. 9 shows the rasp system 100 in an extended configuration, in which the tissue removal member 115 is in a second position relative to the outer housing 118, the second position distal to the first position. When the rasp system 100 is connected to the powered handpiece and power is supplied, hub 120 is rotated, and the interaction of the cam and cam follower surfaces and the bias of the spring convert the rotary motion of the hub to reciprocal motion of the tissue removal member between the extended and retracted configurations.

As set forth previously, inner shaft 114 is joined with shaft key 170; and shaft key 170 is received within housing 118 such that the wings 184 fit in recesses 204, allowing axial translation of shaft key 170 relative to the outer housing 118 but prohibiting rotation of shaft key 170. A proximal portion of shaft key 170 is received within the driving hub bore 240, which is rotatable relative to the shaft key 170 and the outer housing 118. More specifically, the inner wall 233 slidably rotates about the shaft key 170 while the outer wall 232 slidably rotates relative to the housing 118. The cam surface 206 of the outer housing 118 is positioned immediately adjacent the complementary cam follower surface 226 of the driving hub 120. The cam surface 206 of the outer housing 118 is distal to the proximal end of the tissue removal member 115.

A motion conversion mechanism, which may also be called a motion mechanism, is provided by the outer housing including its cam surface and the hub including its cam follower surface. In extended configuration, hub 120 is positioned such that cam follower surface 226 is flush against cam surface 206, with hollows 230 on follower cam surface 226 complementarily fitting against the lobes 208 of cam surface 206. In the retracted configuration, the driving hub 120 is rotated relative to the outer housing 118 such that the lobes 228 on follower cam surface push against the lobes 208 of cam surface 206, thus forcing driving hub 120 proximally, or downward, relative to the outer housing 118. As hub 120 moves proximally, shaft key 170, inner shaft 114 and rasp head 108 are pulled proximally with the hub, but they do not rotate. Proximal hub face 237 rotatably bears against washer 128, which in turn bears against split ring 127, to pull the tissue removal member 115 proximally. As hub 120 continues to rotate, spring 250 pushes distally to axially translate hub 120 back to the extended position, carrying with it shaft key 170, inner shaft 114 and rasp head 108. In the embodiment depicted in FIGS. 8 and 9, cam surface 206 and cam follower surface 226 each have two lobes and two hollows, so that with one full rotation of hub 120, tissue removal member 115 is twice axially reciprocated. In an alternate embodiment, the cam and cam follower surfaces may have more than two lobes and hollows, so that one rotation of the hub may result in multiple reciprocations. In another alternate embodiment, the cam and cam follower surfaces may each have only one lobe and one hollow, resulting in a single reciprocation per revolution. It is appreciated that while the lobes and hollows depicted herein are rounded, however in other embodiments the lobes and/or hollows may be pointed or sharply angular.

As set forth previously, rasp head 108 comprises uni-directionally oriented teeth, which are oriented proximally toward the suction opening 112. Thus, as tissue removal member 115 reciprocates distally and proximally, the teeth cut into any adjacent tissue as the tissue removal member moves proximally. This proximal cutting action may aid in moving cut tissue debris toward the suction opening. Reciprocation of the flat tissue removal surface 115 against the tissue allows for creation or preparation of a flat surface on the tissue.

Figure 10:
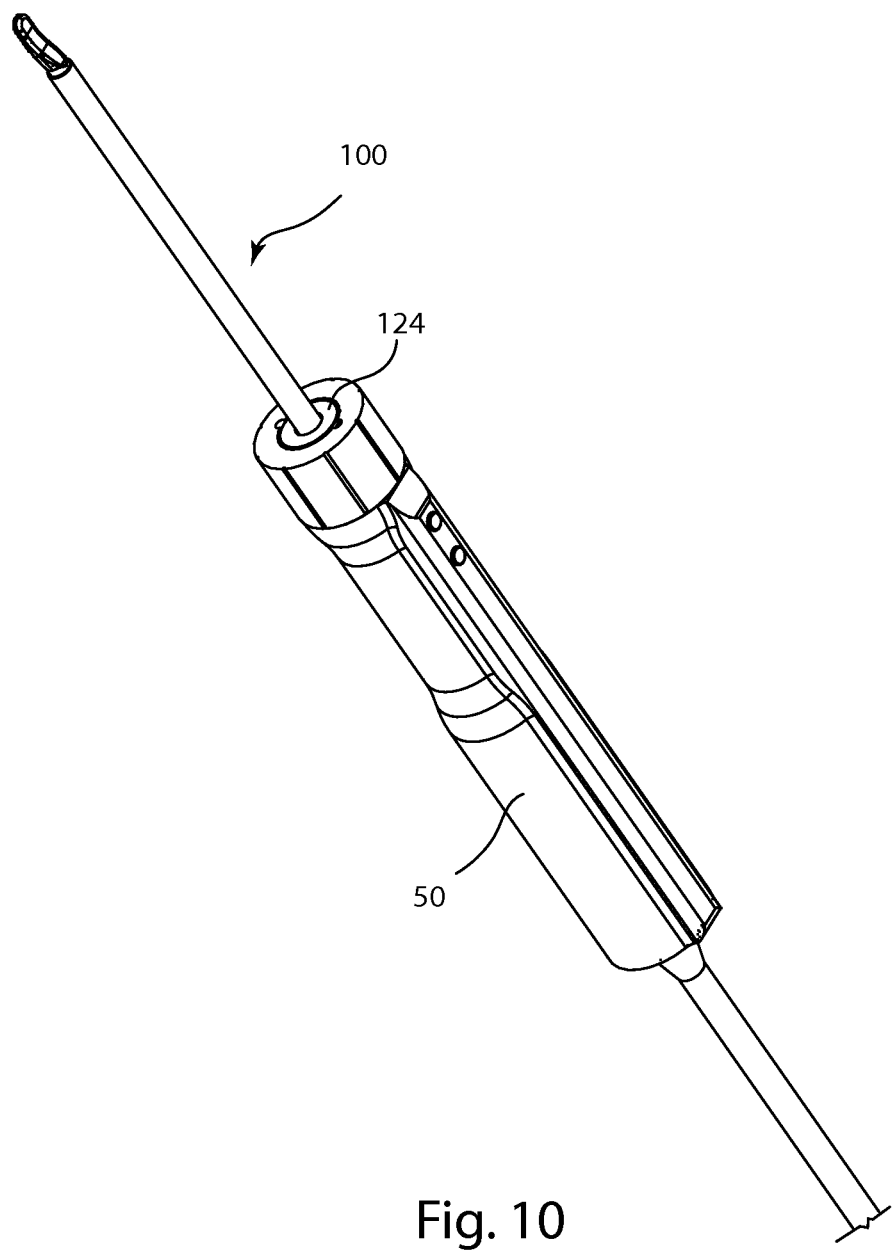
FIG. 10 is an isometric view of the rasping system of FIG. 1A coupled in an exemplary powered handpiece.

FIG. 10 illustrates rasp system 100 engaged in an exemplary powered rotary handpiece 50. Powered rotary handpiece 50 may be a handpiece known in the art, and provides rotary power and suction to rasp system 100. When the rasp system 100 is engaged in the handpiece, the handle portion 106 is surrounded by the handpiece as in FIG. 10, so that no rotating parts are exposed and so that debris pulled through the suction pathway is captured in the handpiece.

FIGS. 11A through 18B set forth alternate embodiments of the rasp head. It is appreciated that alternate embodiments of the rasp system may include any one of the rasp heads disclosed herein, and may include mixed and matched features of the various rasp heads.

Figure 11A:
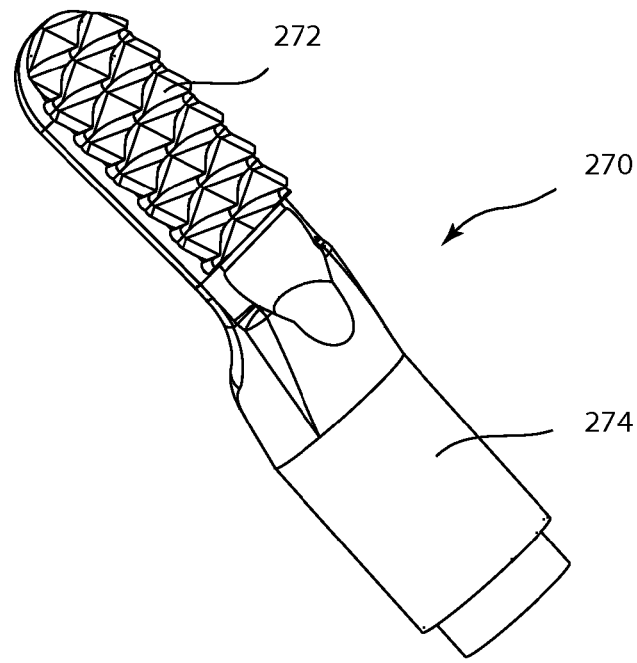
FIG. 11A is an isometric view of an alternate embodiment of a rasp head, a tissue removal portion angled relative to the remainder of the rasp head.
Figure 11B:
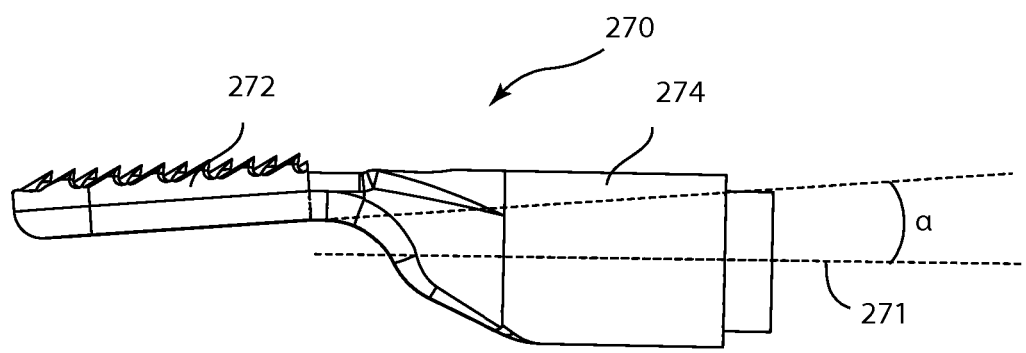
FIG. 11B is a side view of the rasp head of FIG. 11A.

FIGS. 11A and 11B depict a rasp head 270 comprising an angled working portion 272. The working portion 272 is tilted at angle α relative to a longitudinal axis 271 of a head shaft portion 274. Angle α may range from 1 to 10 degrees. More specifically, angle α may range from 3 to 7 degrees. Yet more specifically, angle α may be 5 degrees.

Figure 12A:
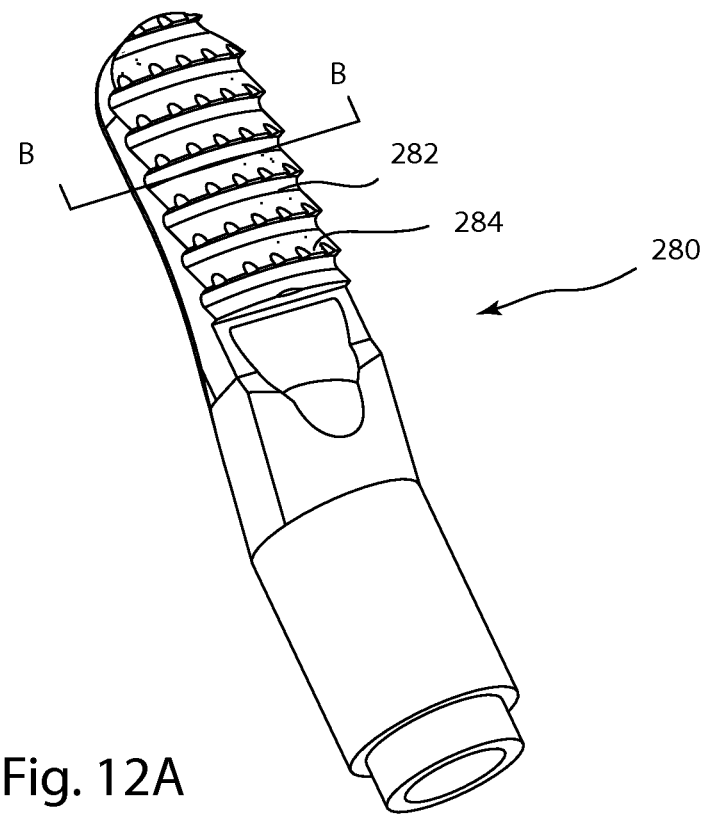
FIG. 12A is an isometric view of an alternate embodiment of a rasp head comprising a convex tissue removal surface.
Figure 12B:
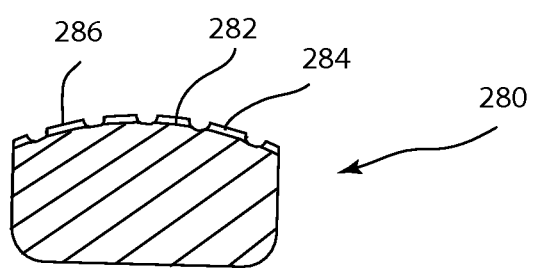
FIG. 12B is a cross-sectional view of the rasp head of FIG. 12A taken along line B-B.

FIGS. 12A and 12B depict a rasp head 280 comprising a convex tissue removal surface 282 from which teeth 284 project. The teeth may comprise straight or curved cutting edges 286; that is the cutting edges 286 may also be convexly curved.

Figure 13A:
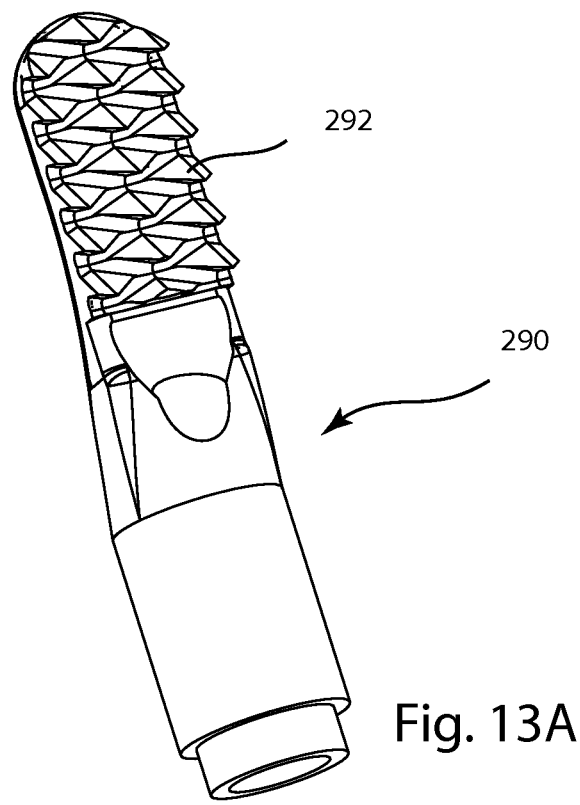
FIG. 13A is an isometric view of an alternate embodiment of a rasp head comprising elongated rasping teeth.
Figure 13B:
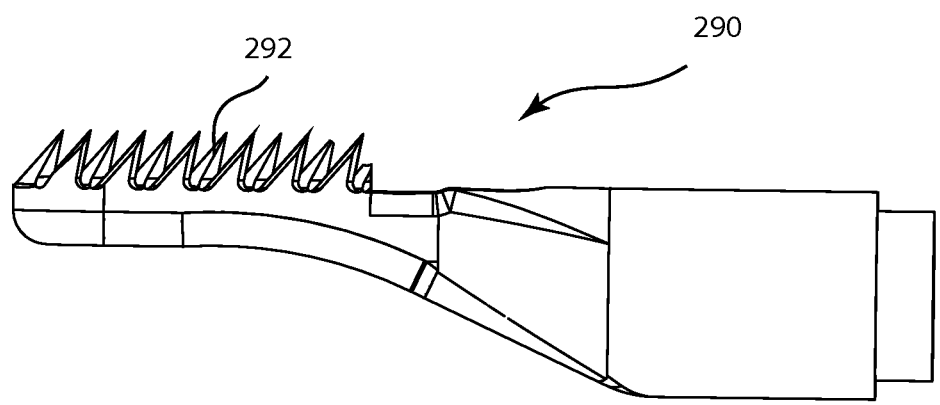
FIG. 13B is a side view of the rasp head of FIG. 13A.

FIGS. 13A and 13B depict a rasp head 290 comprising long teeth 292. The teeth 292 may be longer than teeth in other embodiments and may be advantageous for cutting through relatively softer materials.

Figure 14A:
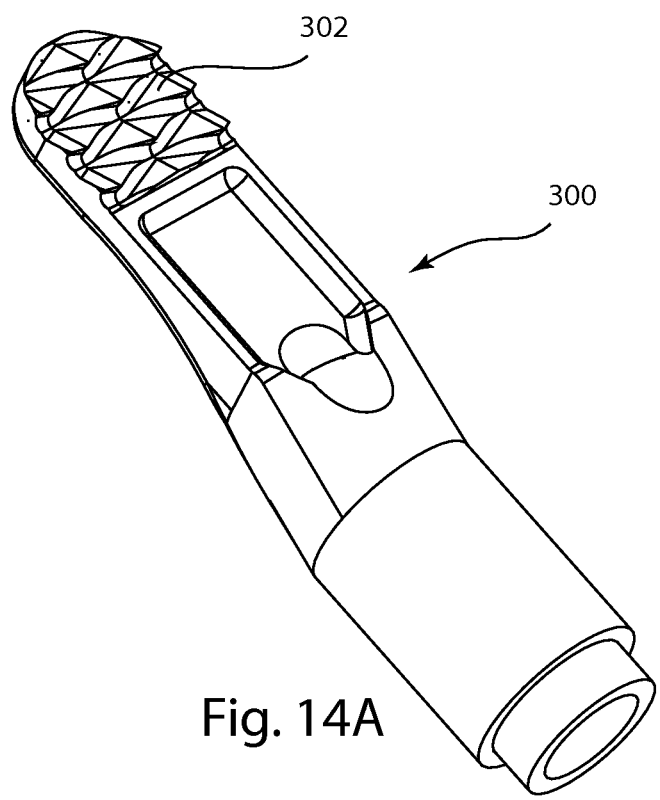
FIG. 14A is an isometric view of an alternate embodiment of a rasp head comprising a reduced tissue removal surface.
Figure 14B:
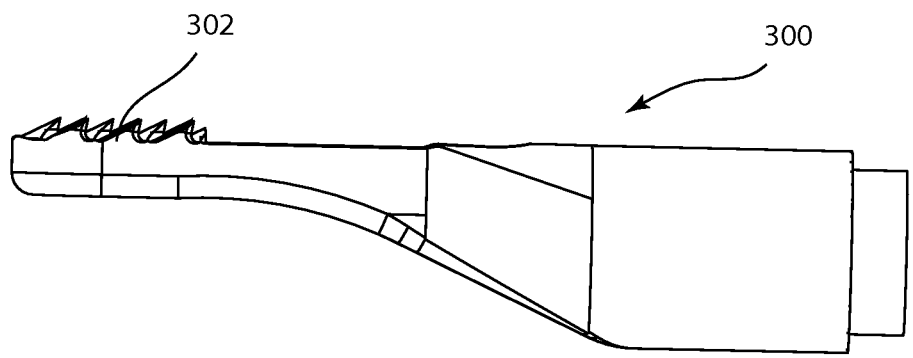
FIG. 14B is a side view of the rasp head of FIG. 14A.

FIGS. 14A and 14B depict a rasp head 300 comprising a relatively smaller tissue removal surface 302. This rasp head may be advantageous for accessing smaller and/or more confined areas such as the wrist joint, and for minimizing contact with tissues adjacent the area targeted for tissue removal. It is appreciated that in alternate embodiments, a smaller tissue removal surface may take the form of a longer but narrower tissue removal surface.

Figure 15A:
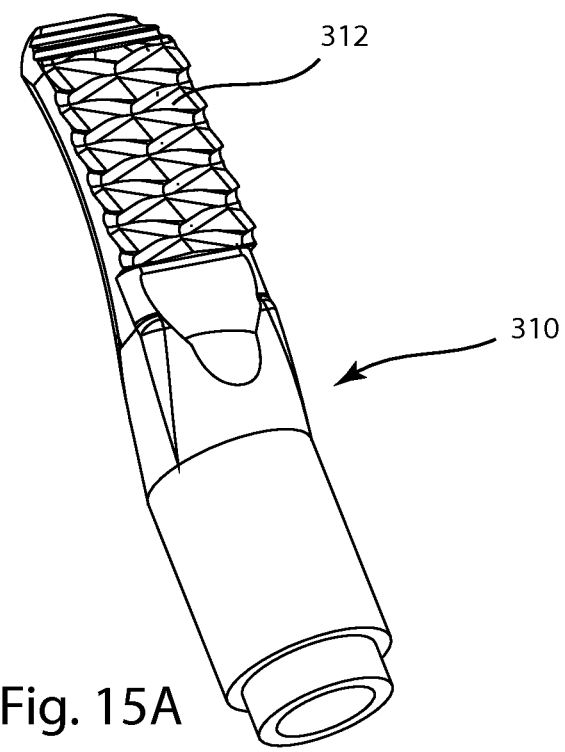
FIG. 15A is an isometric view of an alternate embodiment of a rasp head comprising a crescent-shaped tissue removal surface.
Figure 15B:
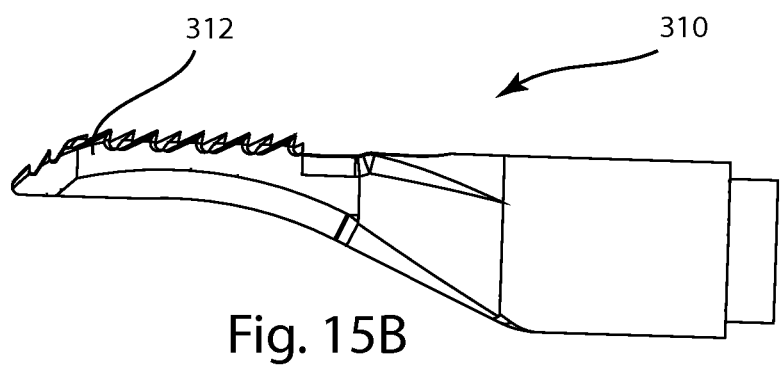
FIG. 15B is a side view of the rasp head of FIG. 15A.

FIGS. 15A and 15B depict a rasp head 310 comprising a curved or crescent-shaped tissue removal surface 312. Tissue removal surface 312 may be convexly curved longitudinally, or both longitudinally and transversely.

Figure 16A:
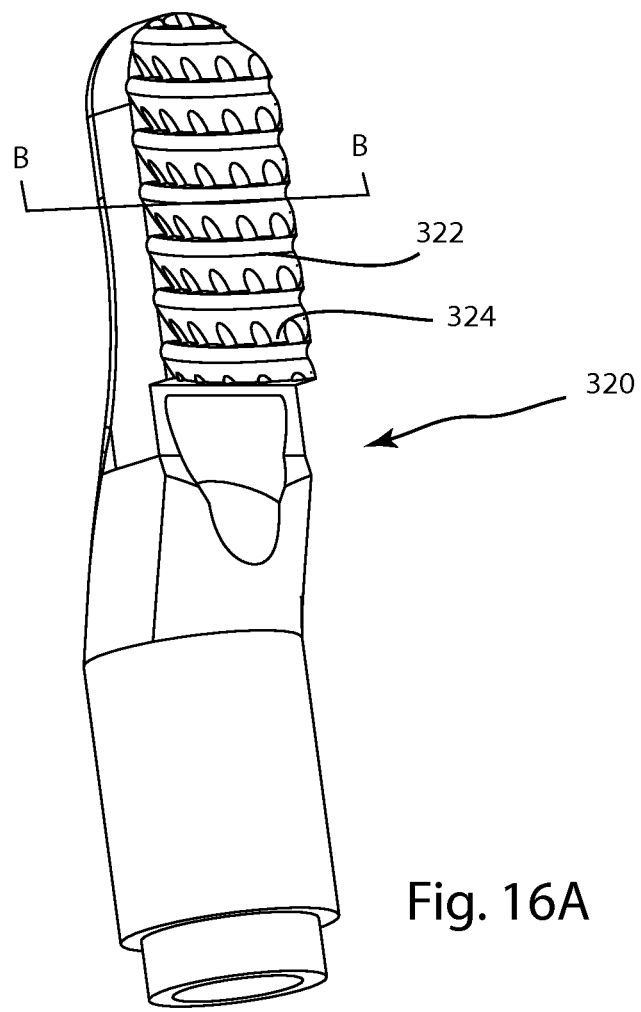
FIG. 16A is an isometric view of an alternate embodiment of a rasp head comprising a concave removal surface.
Figure 16B:
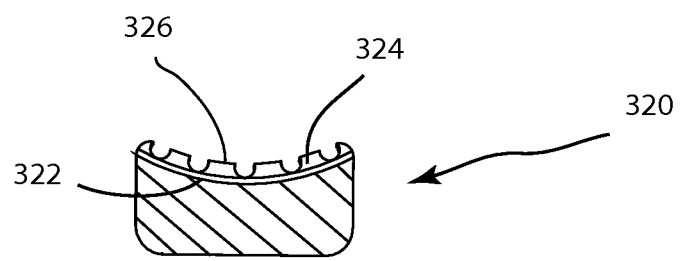
FIG. 16B is a side view of the rasp head of FIG. 16A.

FIGS. 16A and 16B depict a rasp head 320 comprising a concave tissue removal surface 322 from which teeth 324 project. The teeth may comprise straight or curved cutting edges 326; that is the cutting edges 326 may also be concavely curved.

Figure 17A:
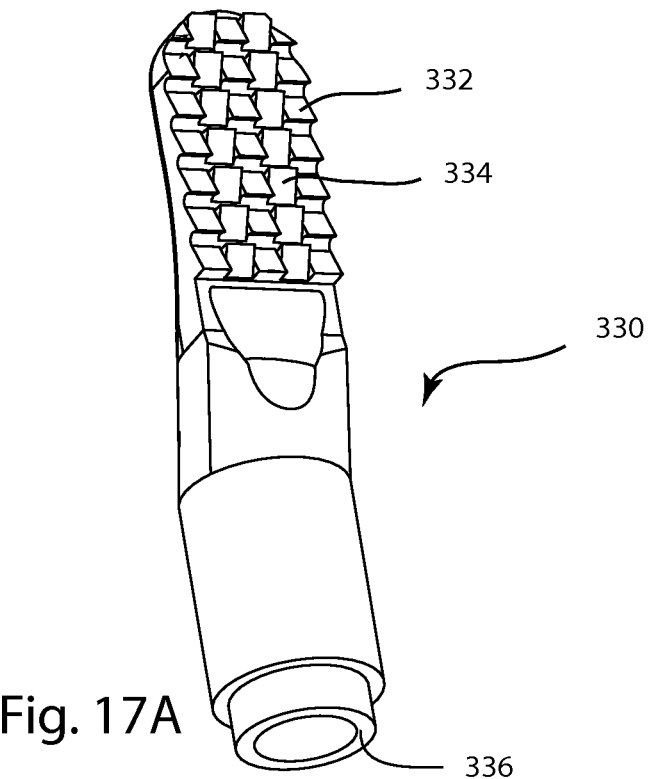
FIG. 17A is an isometric view of an alternate embodiment of a rasp head comprising bi-directional rasping teeth.
Figure 17B:
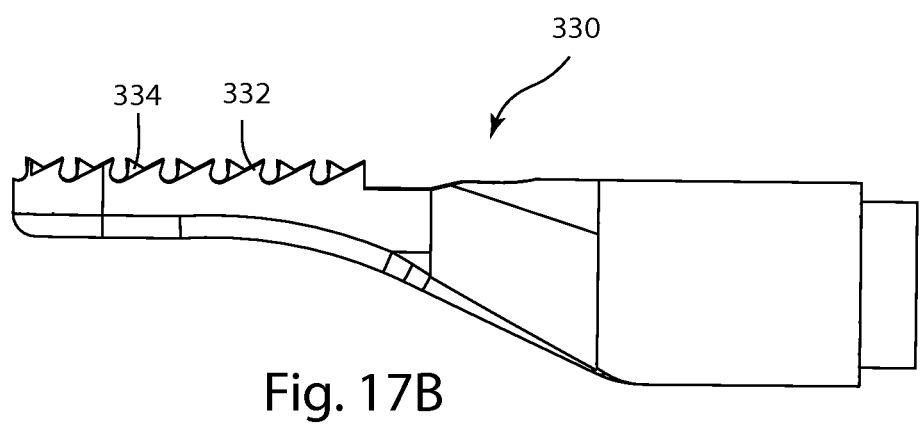
FIG. 17B is a side view of the rasp head of FIG. 17A.

FIGS. 17A and 17B depict a rasp head 340 comprising bi-directional teeth. A plurality of first teeth 332 are oriented proximally, or toward a proximal end 336 of the rasp head, while a plurality of second teeth 334 are oriented distally. When used as part of a reciprocating rasp system such as rasp system 100, tissue cutting may occur in both directions as the rasp head is axially reciprocated.

Figure 18A:
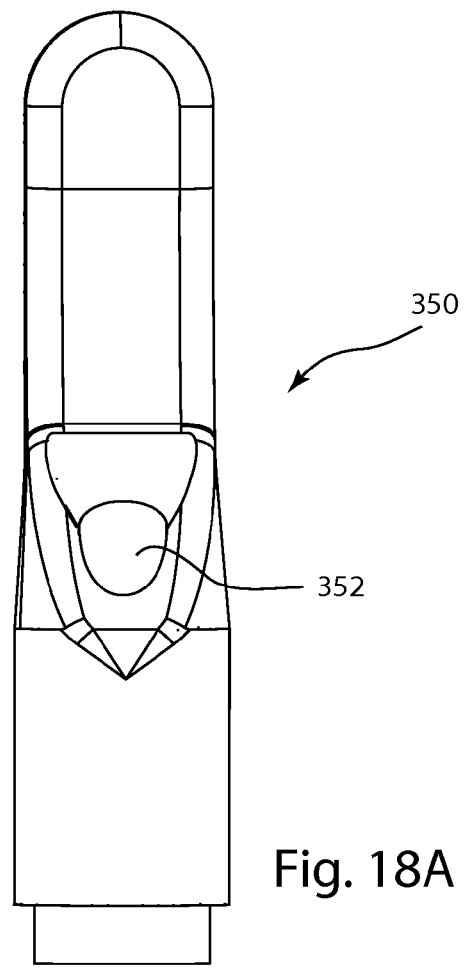
FIG. 18A is an isometric view of an alternate embodiment of a rasp head comprising a suction pathway opening on a back side of the head.
Figure 18B:
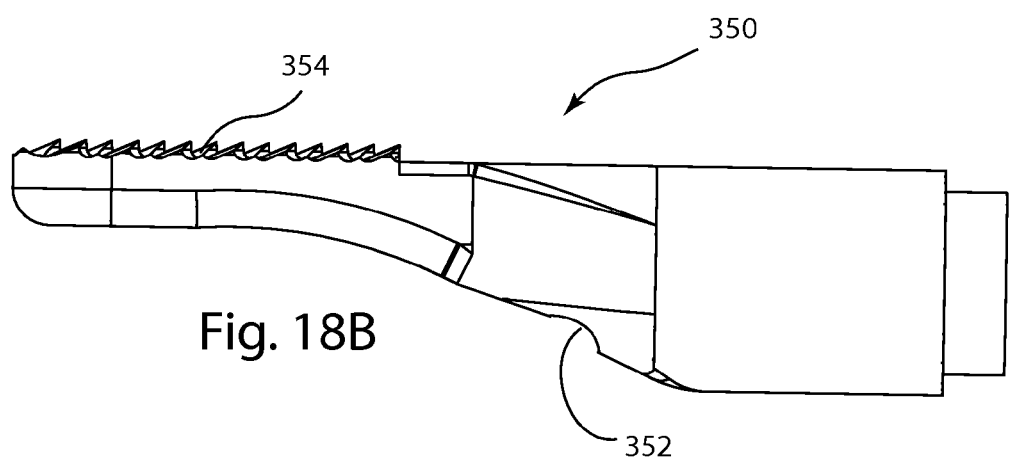
FIG. 18B is a side view of the rasp head of FIG. 18A.
Figures 19A, 19B, 19C:
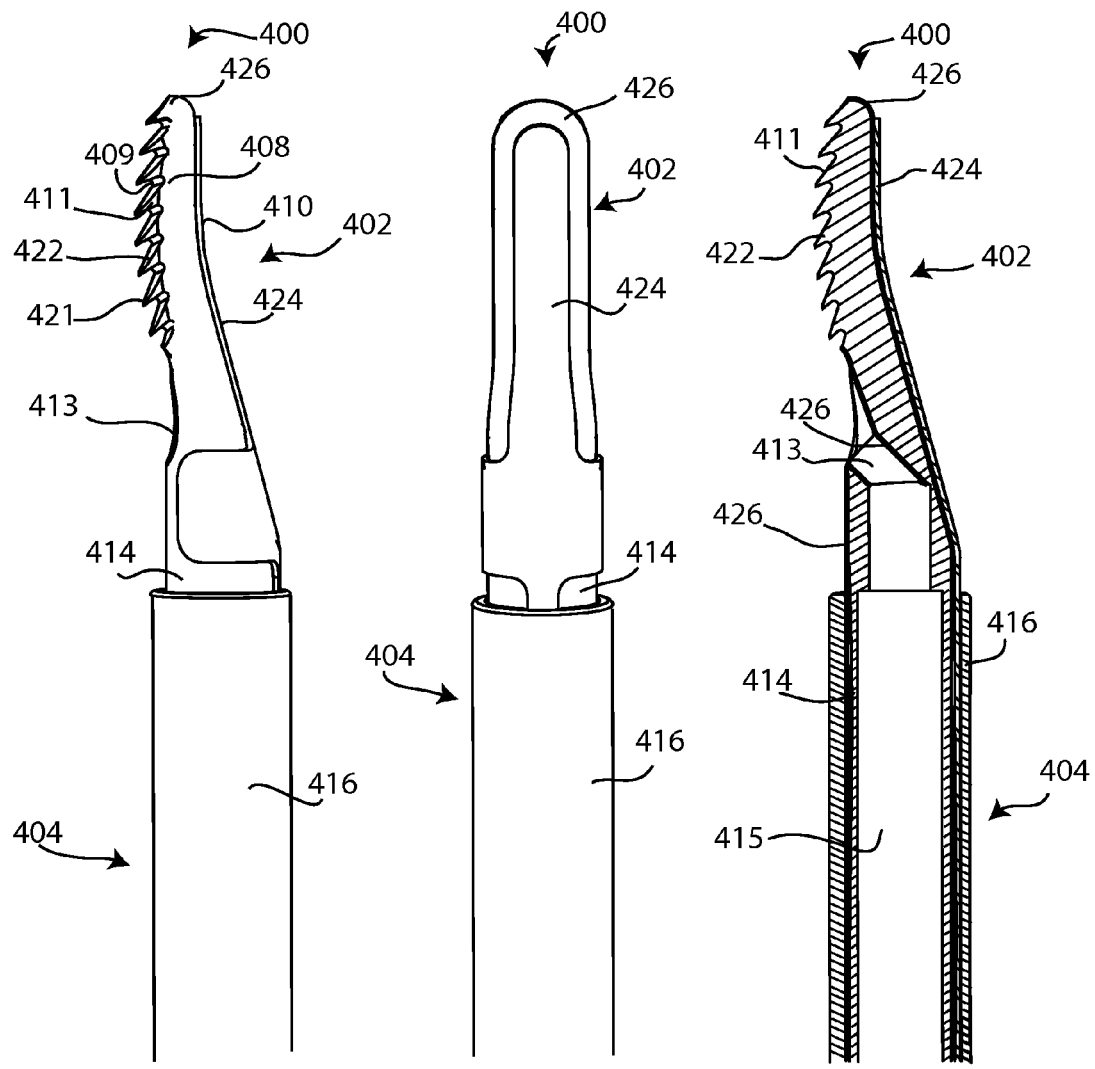
FIG. 19A is a side view of head and shaft portions of an RF/reciprocating rasp device including a rasp tissue removal surface, an ablation electrode integral with the tissue removal member, an insulating layer, and a return electrode.
FIG. 19B is a top view of the device of FIG. 19A.
FIG. 19C is a cross-sectional side view of the device of FIG. 19A.
Figure 20:
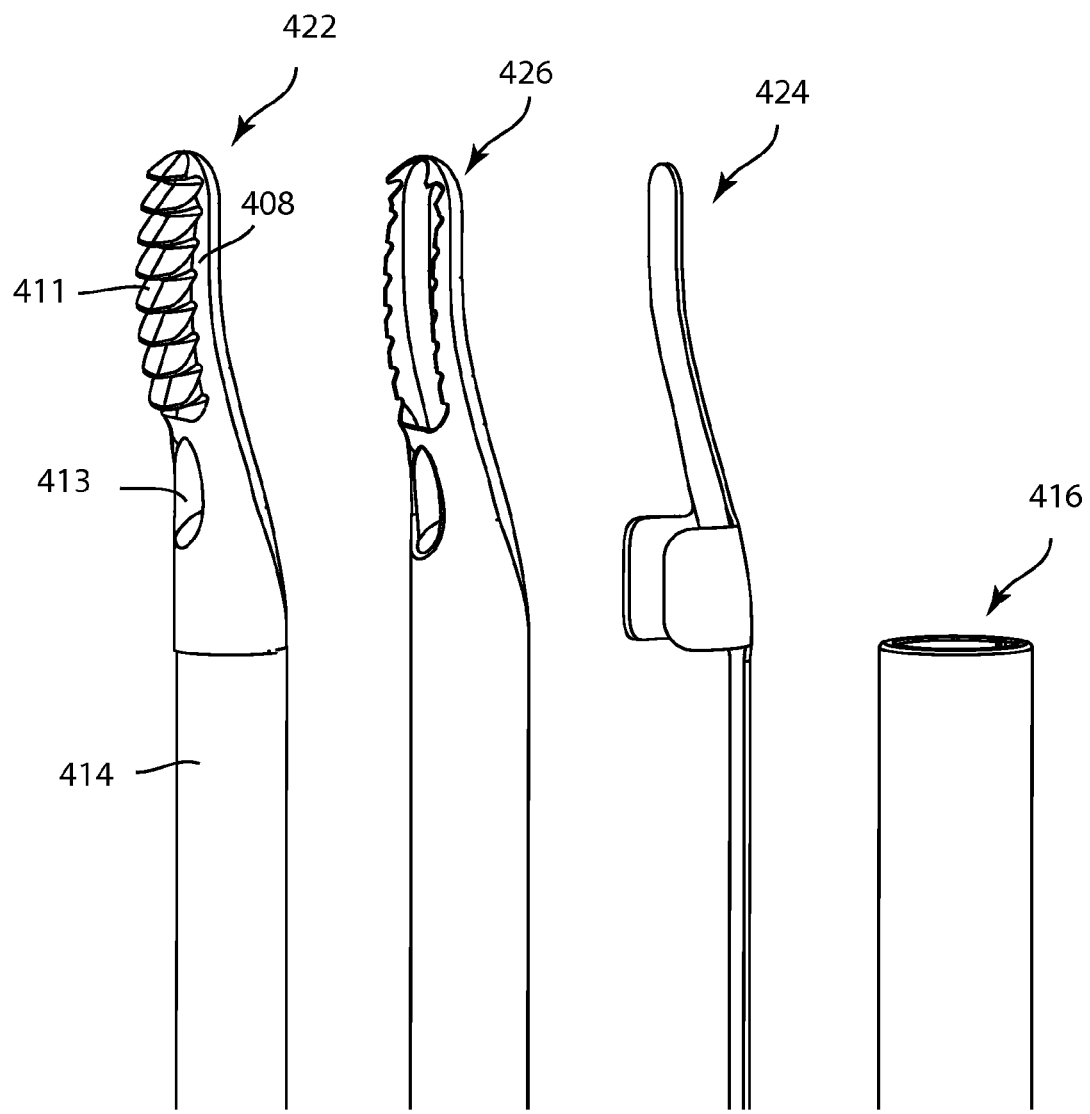
FIG. 20 is an exploded isometric view of the device of FIG. 19A including a tissue removal member which is integral with the ablation electrode, the insulating layer, the return electrode, and an outer sleeve.

FIGS. 18A and 18B depict a rasp head 350 comprising a suction pathway opening 352 located on the back of the rasp head, on the opposite side as a tissue removal surface 354. It is appreciated that any of the rasp head embodiments disclosed herein may include a similarly located suction pathway opening.

In the embodiments disclosed herein, the rasp head and reciprocating inner shaft may comprise stainless steel, titanium, or other metals or metal alloys. The outer sleeve may comprise metal, plastic, or polymer. The outer housing and rotating hub, and cam and cam follower surfaces, may each comprise polymer, plastic, metal, metal alloy, ceramic, polyether ether ketone (PEEK), thermoplastic polyetherimide (PEI) or a combination thereof. The hub may be coated to improve lubricity or contact strength.

Rasp system 100 may be used in a variety of methods for tissue removal and/or resurfacing. In general, rasp system 100 may be used for abrasionplasty, which encompasses both chondroplasty, or removal of cartilaginous material, and osteoplasty, or removal of bone material. Such tissue removal/resurfacing procedures may be carried out on any bone and/or joint. Similarly, rasp system 100 may be used in treatment of osteochondritis dissecans (OCD) on any affected bone to remove bone fragments. In addition to bone material, rasp system 100 may be used for resurfacing or removal of scar tissue, periosteum, fibrocartilage, functioning cartilage, or nucleus pulposus tissues. Rasp system 100 may also be used in resection and/or resurfacing of bone surfaces in preparation for re-attachment of tendons, preparation for joint fusion, or preparation for implantation of joint replacement device components. The rasp head 108 may be modified to produce alternative embodiments wherein: the size of the rasp head is varied in length, width, and/or thickness; the shape and dimensions of the rasping surface are varied; the number and/or rows of teeth are varied; and/or the orientation of the teeth is varied, among other variations. Rasp 100 and alternative embodiments may be used independently or with common surgical cannulas known in the art. Specific uses for the rasp system 100 and alternative embodiments are set forth herein, however it is appreciated that the rasp may be used in other tissue removal procedures within the scope of the invention.

In the joints of the ankle, rasp system 100 may be used to relieve anterior impingement by removing impinging osteophytes on the talus and/or tibia. Use of rasp system 100 may be advantageous over a bun, as a burr may penetrate too deeply into the bone cortex and cause a fracture in the talar neck. The smaller size and gentler action of rasp system 100 may result in a less aggressive approach than that provided with a bun. Rasp system 100 may also be used in the removal of chondrocytes to address chondromalacia of the talar dome and/or the tibial plafond. Medial and/or lateral guttural impingement of the ankle may be relieved by removal of osteophytes with rasp system 100. Depending on the size, shape and/or accessibility of the tissue to be removed, rasp system 100 comprising rasp head 108 which has a generally flat working surface may be used, or alternative embodiments comprising rasp head 310 with a crescent-shaped working surface or rasp head 280 with a convex working surface may be used.

Rasp system 100 may be used in procedures performed on the knee. Rasp system 100 may be used for symptomatic osteophyte removal, especially along the marginal articular edges of the joint. Rasp system 100 may be used for anterior cruciate ligament (ACL) notchplasty. For this procedure, it may be advantageous to use a system comprising rasp head 310 with a crescent-shaped working surface or rasp head 280 with a convex working surface. Also, a system using rasp head 270 with an angle of 3° to 5° may be ideal for notchplasty access. In addition, rasp system 100 or an alternate embodiment may be used in the knee to perform abrasionplasty to address OCD or chondromalacia.

In the hip, rasp system 100 may be used to address impingement by removal of bony prominences and/or osteophytes. Labral repairs may be performed, such as preparation of the acetabular rim for healing of a labral tear, as a non-limiting example. As in the ankle and knee joints, the rasp may used in the hip for removal of osteophytes and/or chondrocytes to address OCD or chondromalacia. In some procedures in the hip, an alternate embodiment of rasp system 100 comprising a curved shaft portion may be advantageous. In this embodiment the optional outer sleeve may not be required.

In the shoulder, rasp system 100 or alternate embodiments may be used to remove bone and/or cartilage material in at least the following procedures: acromial clavicular joint resection (also known as the Mumford procedure or AC resection); subacromial decompression; glenoid rim abrasionplasty; and osteoplasty in preparation for rotator cuff re-attachment.

In the spine, rasp system 100 may be used in vertebral endplate abrasionplasty, and in preparation for vertebral fusion or artificial disc implantation. Around the facet joints, rasp system 100 may be used for removal of bone spurs, and preparation of articular surfaces for facet joint fusion or replacement. Especially along the curved surfaces around the facet joints, a rasping system comprising the crescent, convex or concave shaped rasp head may be advantageous. Also, the rasp may be used to remove osteophytes or bony prominences in or around the spinal canal.

For procedures in joints of the wrist, a smaller working head surface such as that in rasp head 300 may be advantageous for reaching into confined areas without disturbing adjacent soft tissues. Rasp system 100 may be used for chondroplasty, osteoplasty and other joint preparation procedures in the wrist.

In the elbow, rasp system 100 or alternate embodiments may be used to remove osteophytes on the edges of the trochlea, to prevent impingement on the ulnar nerve. Marginal osteophytes or bony prominences may be removed at the marginal edges of the articulating surfaces of the elbow. For treatment of arthritis, bone spurs may be removed to aid in restoring motion. As with the wrist, use of a system comprising rasp head 300 with a reduced tissue removal surface may be advantageous, as may use of a system comprising a convex or crescent shaped head.

In the skull, rasp system 100 may be employed for sculpting of bony prominences on the cheek areas, forehead, nose, chin and jaw.

Removal of soft tissues adjacent to articular joints is often necessary to gain access to the joint space. For example, in a hip or shoulder arthroscopy procedure, the ligaments forming the joint capsule may need to be resected or penetrated to clear a pathway for a surgical instrument to reach the joint.

Disclosed herein are embodiments of a reciprocating rasp system which includes integral RF ablation capability, allowing a practitioner to use a single instrument for RF ablation or coagulation of soft tissues, and removal of hard or bony tissues. The localized RF current flow provided by the instruments disclosed herein may vaporize soft tissues to which it is applied. Use of the combined rasp/RF instrument may provide advantages including: the need for fewer portal incisions, which may reduce patient pain and/or healing time; reduced complexity of the procedure, since fewer individual instruments are required; reduced tissue trauma, as fewer instruments are moved in and out of the affected area, and reduced cost.

FIGS. 19A-24 illustrate embodiments of reciprocating rasp systems with integrated RF ablation capability. Although not all possible combinations are shown, it is appreciated that an RF/rasp system may include any of the reciprocating rasp variations disclosed herein, with any of the rasp head configurations disclosed herein. Referring to FIGS. 19A-19C and 20, one embodiment of an RF/rasp device 400 includes a head portion 402, shaft portion 404, and handle portion 406 (not shown, but may include the same components as handle portion 106 or other handle portions described herein). The head, shaft and handle portions of system 400 may be the same as other head, shaft and handle portions disclosed herein, with the addition of an RF ablation system 420 integrated into the device. Head portion 402 includes rasp head 408, which has a first side 409 and a second side 410 opposite the first side. A tissue removal surface 411 and suction opening 413 for a suction pathway are located on the rasp head 408. A tissue removal member 412 comprises rasp head 408 and inner shaft 414, and may further include portions of the RF ablation system 420. Shaft portion 404 includes inner shaft 414 and outer sleeve 416, and may further include portions of the RF ablation system 420. A suction pathway 415 comprising distal suction opening 413 and a proximal opening on the hub in the handle portion 406 extends through device 400. Tissue removal surface 411 may comprise a plurality of teeth 421 for cutting and removing hard tissue.

The RF ablation system 420 includes an ablation electrode 422, a return electrode 424, and may include an insulation layer 426 positioned between the ablation and return electrodes. RF system 420 may be described as a bi-polar RF system. In this embodiment of FIGS. 19A-20, the ablation electrode 422 is co-located with the rasp head 408 and inner shaft 414. Insulation layer 426 coats a majority of rasp head 408, except where tissue removal surface 411 protrudes from the insulation, so that when the ablation system is powered or energized, RF energy is transmitted from the tissue removal surface 411, effectively making tissue removal surface 411 the active ablation electrode. The portion of the ablation electrode which protrudes from the insulation may be referred to as the active ablation portion of the ablation electrode. The insulation layer 426 may also coat all or a portion of the length of the inner shaft 414, and may coat a portion of the suction opening 413, as shown. The RF ablation system 420 is connected to a power source and a controller for controlling transmission of RF current through the system. The controller may be a switch, knob, pedal, lever, dial, button or other suitable control member, located on the powered rotary handpiece 50, or on a separate control apparatus. The RF probe may be powered via the controller on to transmit RF current simultaneously with reciprocation of the tissue removal member; alternately, it may be turned on and off independently of tissue removal member reciprocation. The exposed, or uninsulated surface area of the return electrode 424 may be referred to as the active return portion of the return electrode, and is at least three times greater than the exposed surface area, or active ablation portion, of the ablation electrode 422. The ridges of the rasp teeth on the tissue removal surface may enhance arcing of RF current transmitted from the active ablation portion of the ablation probe.

In a method of use, a practitioner may insert head portion 402 into a targeted area, position tissue removal surface 411 adjacent soft tissues to be treated, activate the RF system 420 to ablate or coagulate soft tissue with RF current flow from the ablation electrode 422 to clear a pathway to a joint, turn off the RF system, position the tissue removal surface 411 adjacent hard tissues to be removed, then power the reciprocating motion to use the tissue removal surface 411 to treat adjacent hard tissue. Soft tissues to be removed through ablation or coagulation may comprise muscle, skin, fascia, blood vessels, ligamentous or other relatively soft tissues, while hard tissues may comprise bone, scar tissue, periosteum, fibrocartilage, functioning cartilage, nucleus pulposus tissues, or other relatively hard tissues. The RF current flow may also cauterize blood vessels and/or coagulate blood flow. Alternatively, RF ablation and rasp reciprocation may be powered simultaneously to remove hard and soft tissues at the same time. Suction may be provided as needed, simultaneously with or independently between RF ablation and rasp reciprocation functions. The suction may pick up loose tissue particles or resected pieces of tissue, remove bubbles created by tissue ablation or blood vessel cauterization/coagulation, and/or help maintain visualization of the surgical site. All of these functions may be accomplished without removal of the head portion 402 from the surgical site. Of course, the functions may be accomplished in any desired order and may be repeated as necessary.

The RF current flow may be provided at selected settings, or power levels to produce the desired results, for example, a higher power level may be used to destroy soft tissues while a lower power level is sufficient for cauterization/coagulation of blood vessels. The overall wattage range of the RF system may be 0 to 300 watts. More specifically, a setting or power level for tissue ablation may be three to four times higher than a setting for blood vessel cauterization or blood coagulation. Yet more specifically, a setting for cauterization/coagulation may be 50 watts, and a setting for tissue ablation may be 200 watts.

Figure 21A:
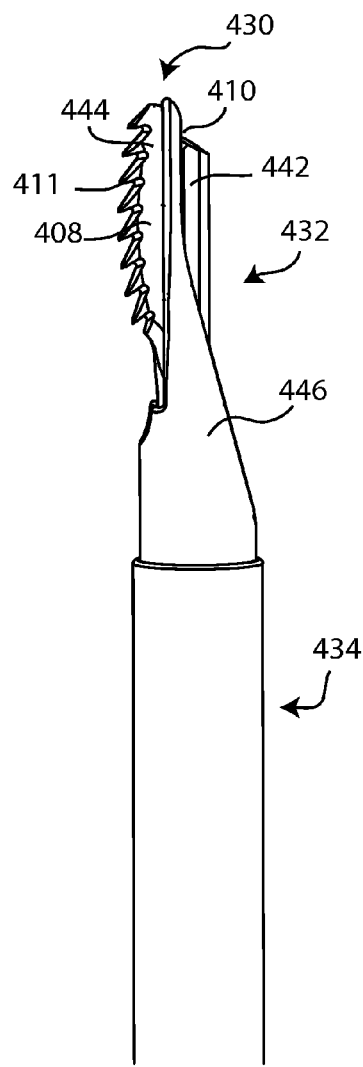
FIG. 21A is a side view of head and shaft portions of an RF/reciprocating rasp device including a tissue removal member comprising a rasp head having a tissue removal surface, an ablation electrode positioned on a back side of the rasp head, an insulating layer, and a return electrode integral with the tissue removal surface, and an outer sleeve.
Figure 21B:
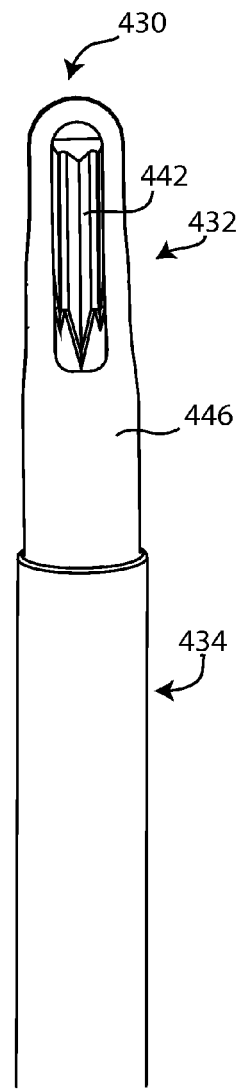
FIG. 21B is a top view of the device of FIG. 21A.
Figure 21C:
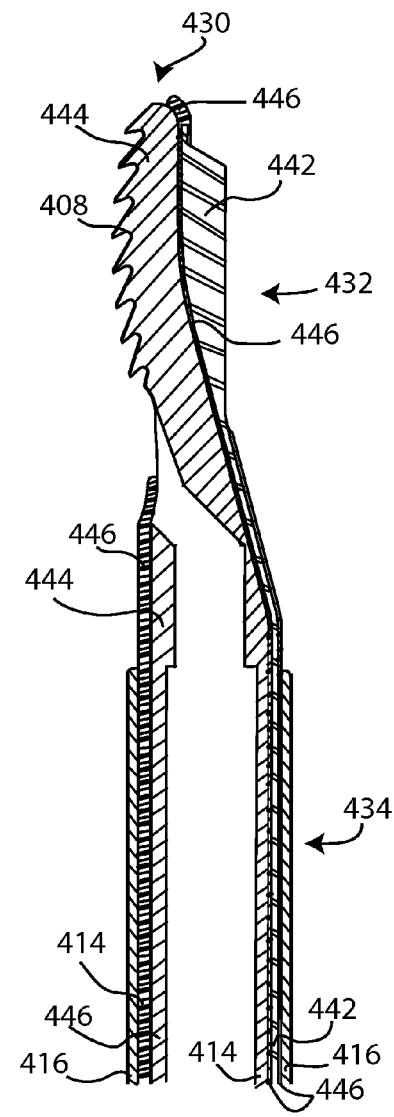
FIG. 21C is a cross-sectional side view of the device of FIG. 21A.
Figure 22:
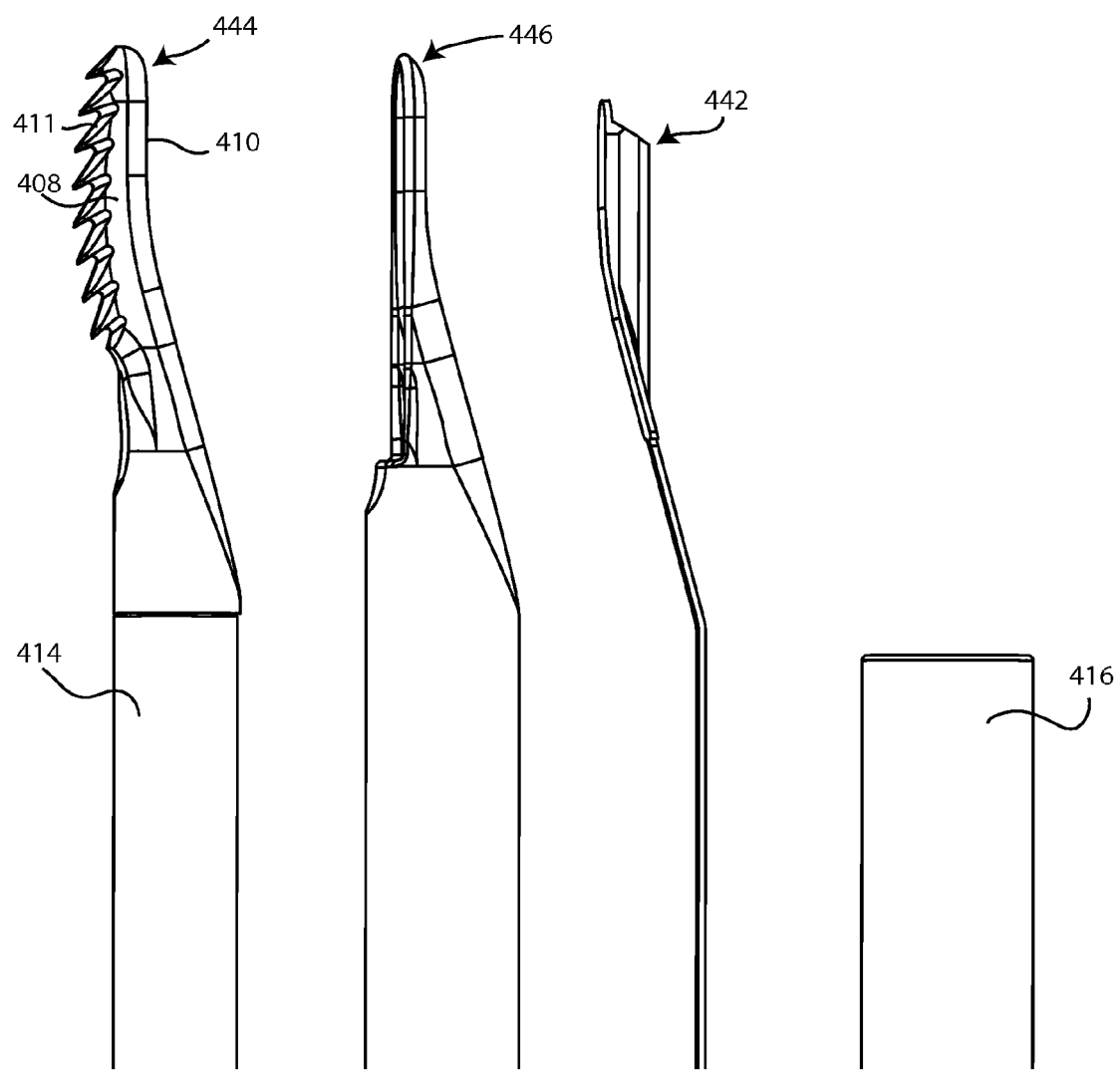
FIG. 22 is an exploded side view of the device of FIG. 21A including the rasp head and inner shaft integral with the return electrode, the insulating layer, the ablation electrode, and the outer sleeve.

Another embodiment of a reciprocating rasp system with an integral RF ablation system is shown in FIGS. 21A-22. The RF/rasp device 430 includes head portion 432, shaft portion 434, and handle portion 436 (not shown, but may include the same components as handle portion 106 or other handle portions described herein). The device further includes RF ablation system 440, which includes an ablation electrode 442, a return electrode 444, and may include an insulation layer 446 positioned between the ablation and return electrodes. Insulation layer 446 may also be between the ablation electrode 442 and the outer sleeve 416, and between the return electrode 444 and the outer sleeve 416, and may extend the length of the shaft portion 434. In this embodiment of FIGS. 21A-22, the ablation electrode 442 is positioned or carried on a second 410, or back side of rasp head 408. Insulation layer 446 coats a majority of rasp head 408, except where return electrode 444 protrudes from the insulation 446, at tissue removal surface 411, effectively making tissue removal surface 411 the active return electrode. The exposed, or uninsulated surface area of the return electrode 444 is at least three times greater than the exposed surface area of the ablation electrode 442. Ridges or other protrusions formed on the ablation electrode 442 may enhance arcing of electrical energy transmitted from the ablation electrode. The device 430 may further include a suction pathway and suction capabilities as described for other embodiments. Methods of use may be the same as those described for previous embodiments.

Figure 23A:
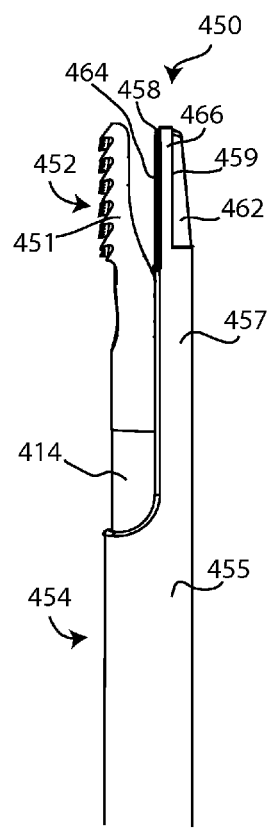
FIG. 23A is a side view of head and shaft portions of an RF/reciprocating rasp device including a tissue removal member comprising a rasp head having a tissue removal surface, an outer sleeve having an extension, an ablation electrode positioned on a first side of the sleeve extension, a return electrode integral positioned on a second side of the sleeve extension, and an insulating layer.
Figure 23B:
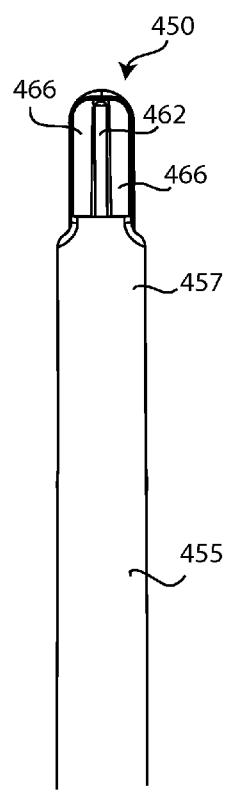
FIG. 23B is a top view of the device of FIG. 23A.
Figure 23C:
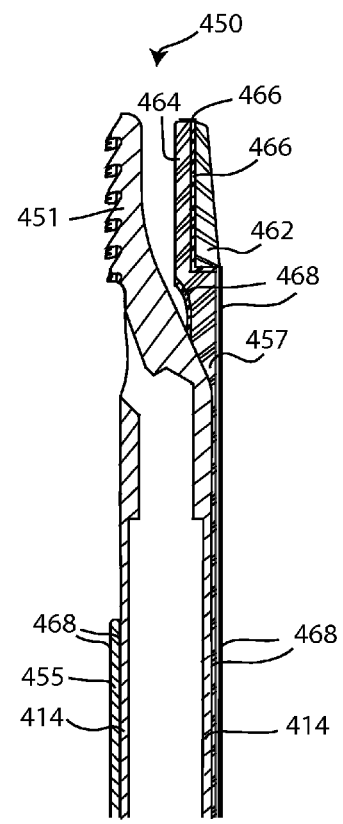
FIG. 23C is a cross-sectional side view of the device of FIG. 23A.
Figure 24:
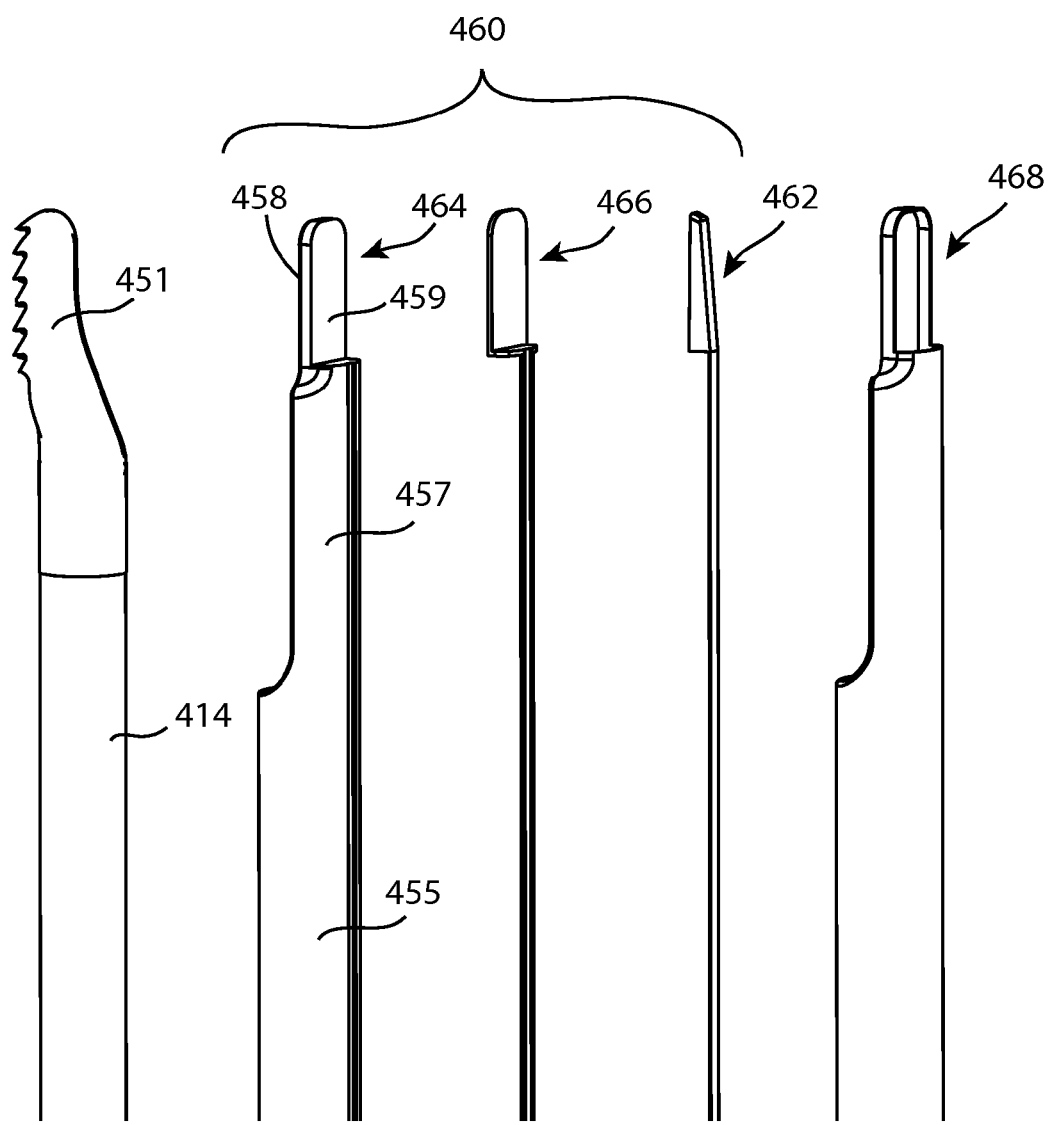
FIG. 24 is an exploded side view of the device of FIG. 23A.

Yet another embodiment of a reciprocating rasp system with an integral RF ablation system is shown in FIGS. 23A-24, in which the ablation and return electrodes are carried on the rasp system stationary outer sleeve. The RF/rasp device 450 includes head portion 452, shaft portion 454, and handle portion 456 (not shown, but may include the same components as handle portion 106 or other handle portions described herein). A reciprocating rasp portion includes rasp head 451 and inner shaft 414. It is appreciated that rasp head 451 may comprise any of the rasp heads disclosed herein and may include features including, but not limited to, teeth or other tissue removal surface, suction opening(s), and a suction pathway. An outer sleeve 455 includes a sleeve extension 457 which projects distally from the tubular portion of the sleeve, and has an inner or first side 458 and an outer or second side 459. The device further includes RF ablation system 460, which includes an ablation electrode 462, a return electrode 464, and an insulation layer 466 positioned between the ablation and return electrodes. In this embodiment of FIGS. 23A-24, the RF system is positioned or carried on the extension 457 of outer sleeve 455. Ablation electrode 462 is carried on the second side 459 of the sleeve extension 457, and may be fin-shaped. Return electrode 464 is integral with sleeve extension 457, and is exposed from the insulation on the first side 458 of the sleeve extension. Insulation layer 466 is sandwiched between the ablation and return electrodes. In this embodiment, sleeve 455 may be coated by a second insulation layer 468 on both the inside and the outside of the sleeve, to isolate it from inner shaft 414. The second insulation layer 468 may also fall outside of the ablation electrode 462, at least along shaft portion 454. Along the shaft portion 454, the ablation electrode 462 is sandwiched between insulation layers 466, 468. The exposed, or uninsulated surface area of the return electrode 464 is at least three times greater than the exposed surface area of the ablation electrode 462. Fins, ridges or other protrusions formed on the ablation electrode 462 may enhance arcing of electrical energy transmitted from the ablation electrode. The device 450 may further include a suction pathway and suction capabilities as described for other embodiments. Methods of use may be the same as those described for previous embodiments.

Suitable materials for the ablation and return electrodes of the RF systems disclosed herein include but are not limited to stainless steel, tungsten, and other conductive materials, metals or metal alloys. Suitable materials for the insulation layers include but are not limited to polytetrafluoroethylene (PTFE), polyolefins, acrylic, polycarbonate, acrylonitrile butadiene styrene (ABS), plastics, and other insulating materials.

Other embodiments of reciprocating rasp system may include imaging, navigation, and/or infusion capabilities. Referring to FIGS. 25A-25C, rasp system 470 includes imaging and/or navigation capabilities. System 470 comprises head portion 472, shaft portion 474, and handle portion 476. Head portion 472 includes a reciprocating rasp head 478, which may comprise any of the rasp heads disclosed herein, including rasp heads with RF ablation capability. Adjacent head portion 472 is auxiliary device 480. Auxiliary device 480 may be received in a housing 482. Auxiliary device 480 may include an imaging instrument, which may be a camera, ultrasound transmitter, light transmitter, or other imaging transmitter or scanner. In another embodiment, auxiliary device 480 may include a computer-aided navigation reference marker, which may be used in conjunction with a fluoroscopic C-arm and anatomic reference markers to provide intraoperative fluoroscopic images. Auxiliary device 480 may be fixed in housing 482, or may be mobile, able to extend out of housing 482 at any angle. Auxiliary device 480 may be rotatable and sufficiently mobile to capture a 360° view of the environment surrounding the rasp head. For example, auxiliary device 480 may be coupled to a flexible shaft 484, allowing the device 480 to extend and retract in and out of housing 482, and bend around head 478. In the embodiment shown, housing 482 is formed on outer sleeve 116; it is appreciated that the housing may be located at any position relative to head 478, whether laterally adjacent, inferior, or superior to the head. In another embodiment, housing 482 may be integrally formed or co-located with head 478. An auxiliary sleeve portion 486 may be formed on outer sleeve 116 and include an auxiliary bore 488. Wiring and controls for auxiliary device 480 may pass through bore 488.

An infusion system may be integrated into any of the rasp systems disclosed herein. FIGS. 26A-26C illustrate one embodiment of such a system. Rasp system 490 includes an RF ablation system 420, auxiliary device 480, and infusion port 492. Infusion port 492 may be positioned adjacent the rasp head 408, providing an opening through which saline or other fluids may be pumped to infuse a targeted site. An infusion bore 494 may open into auxiliary bore 488 as shown or may remain separate. Flexible or rigid tubing may extend through infusion bore 494 to infusion port 492, providing a path for the fluid from a fluid source to the port. By way of non-limiting example, the infusion system may introduce saline, pain relief medication, bone morphogenic protein, bone growth stimulator, anesthetic agents, analgesic agents, anti-inflammatory agents, anti-rejection agents, growth factors, antibiotics, anti-adhesion factors, saline, glycosaminoglycan varieties, collagen varieties, bio-nutrients, gene-delivery vehicles, stem cells, and/or any other therapeutic substance that is desirable to be dispensed to the surgical site. Infusion may be used in conjunction with the suction capabilities of the rasp system, or separately.

Figure 27:
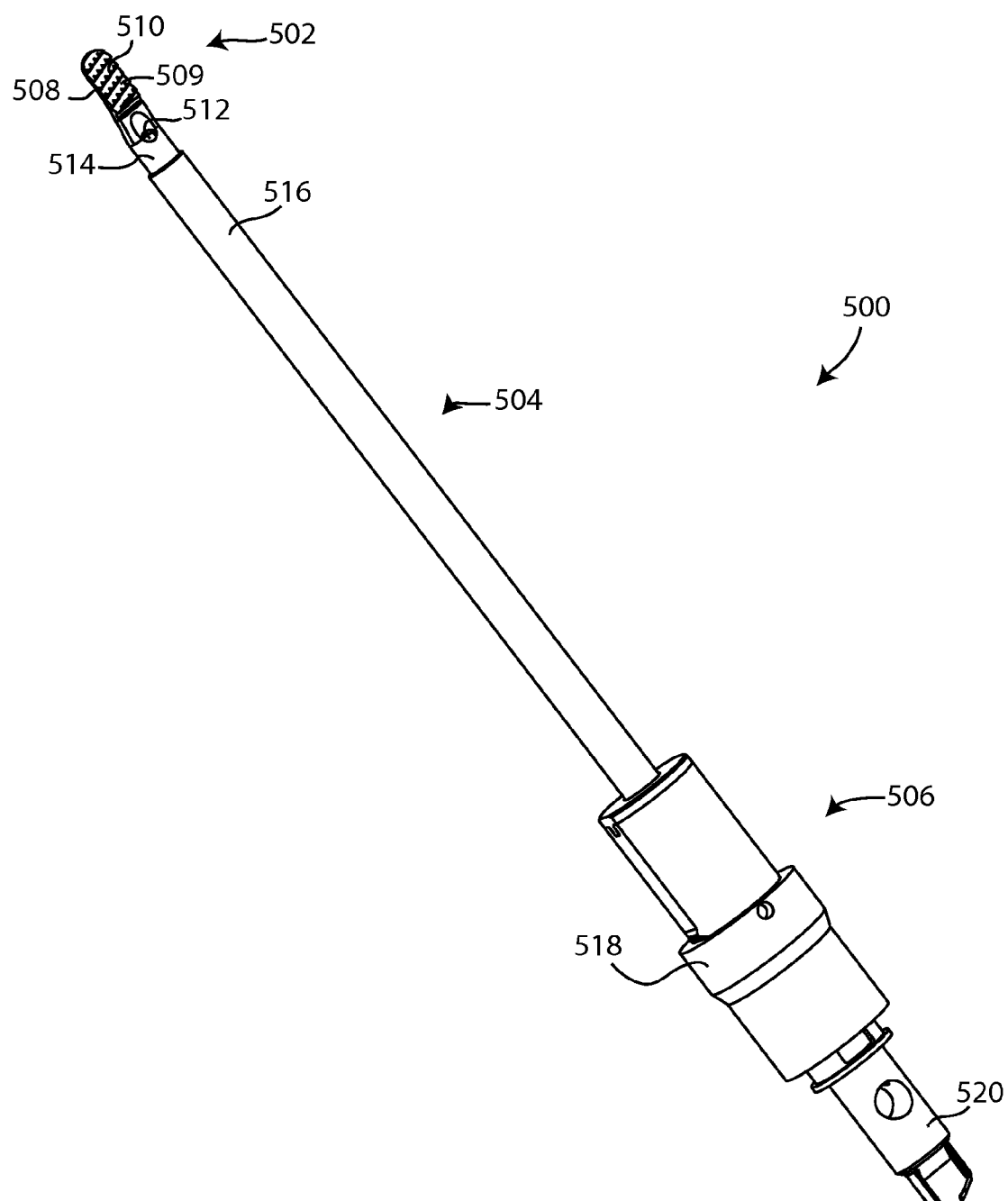
FIG. 27 is an isometric view of an alternate embodiment of a reciprocating rasping rasping system including a head portion, a shaft portion, and a handle portion.

FIGS. 27-33 illustrate an embodiment of a reciprocating rasp system which includes an alternate embodiment of a motion conversion mechanism for converting rotary to reciprocating motion. Referring to FIG. 27, rasp system 500 is shown in an isometric view. Rasp system 500 comprises head portion 502, shaft portion 504, and handle portion 506. Head portion 502 comprises rasp head 508, which includes a tissue removal surface 509 having a plurality of teeth 510 or cutting edges which may cut anatomical tissues when drawn along the tissue surface. A suction opening 512 is located on the head portion 502, and may be disposed between the teeth and the shaft portion. The shaft portion 504 comprises inner shaft 514 which extends proximally from the rasp head 508 and is received in the handle portion 506. Inner shaft 514 is hollow, having a bore 515 (not visible in FIG. 27, seen in FIG. 29) extending from suction opening 512 to a proximal end of the inner shaft, the bore 515 forming a portion of a suction pathway. The inner shaft 514 extends through an optional outer sleeve 516 which is joined to the handle portion 506. Handle portion 506 includes an outer housing 518 which encloses a cam 524 and a fixed cam (within housing 518; not visible in FIG. 27) and partially houses a rotatable hub 520 which is coupled to the cam. When handle portion 506 is engaged in a powered rotary handpiece and power is supplied, hub 520 rotates and consequently cam 524 also rotates, and the cam and fixed cam provide a motion conversion mechanism which converts the rotary motion of the hub to axial reciprocal motion of the inner shaft 514 and attached head 508. Hub 520 may also be referred to as a sluff chamber.

Figure 28A:
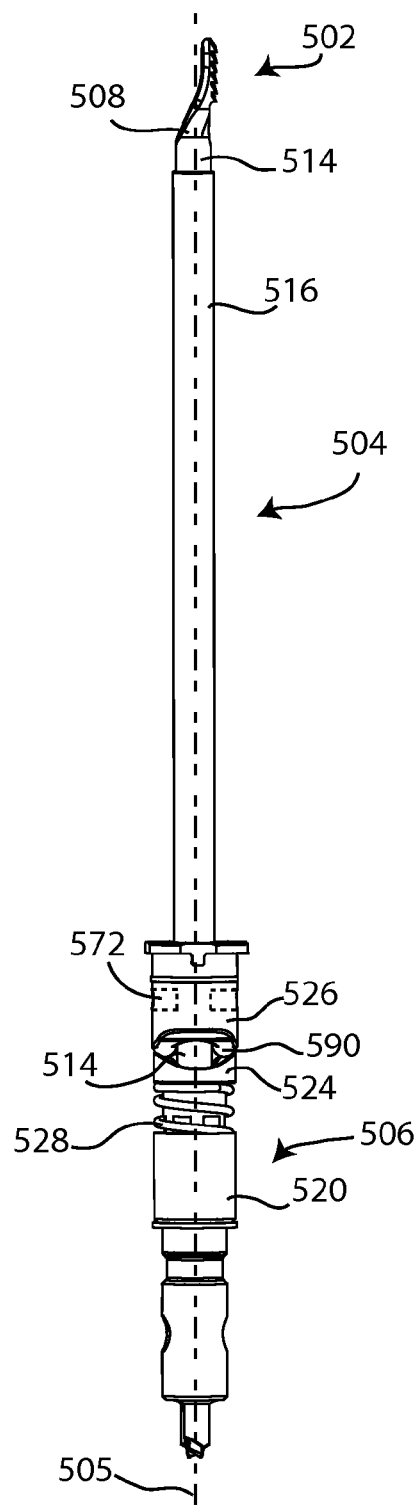
FIG. 28A is a side view of the rasping system of FIG. 27, with an outer housing removed.
Figure 28B:
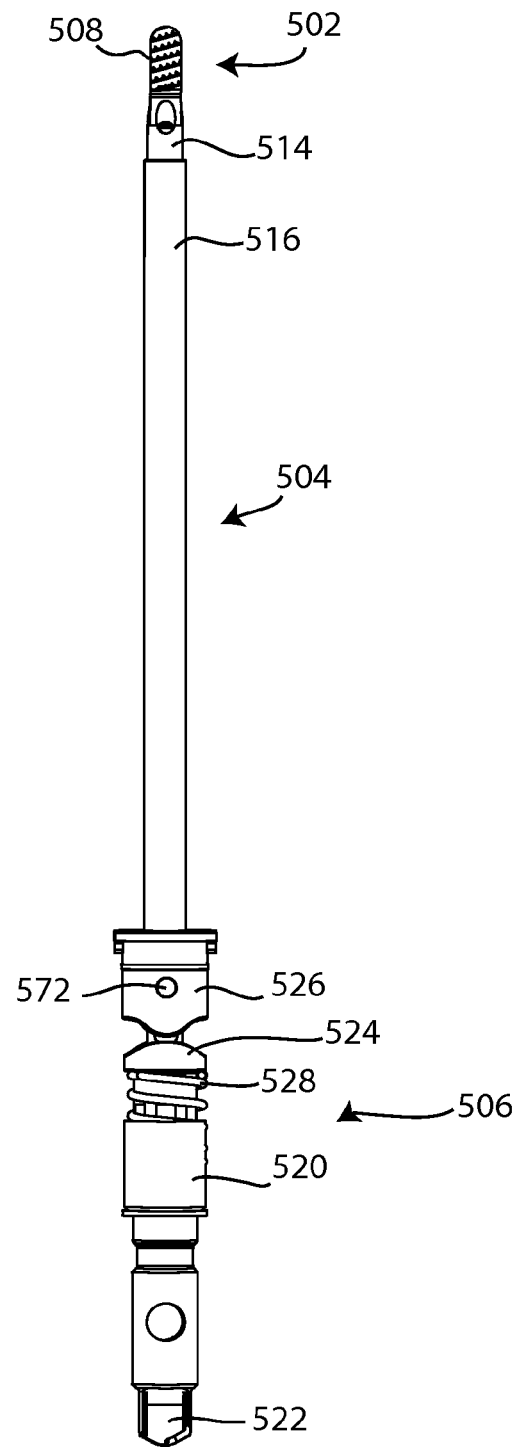
FIG. 28B is a bottom view of the rasping system of FIG. 24A.
Figure 29:
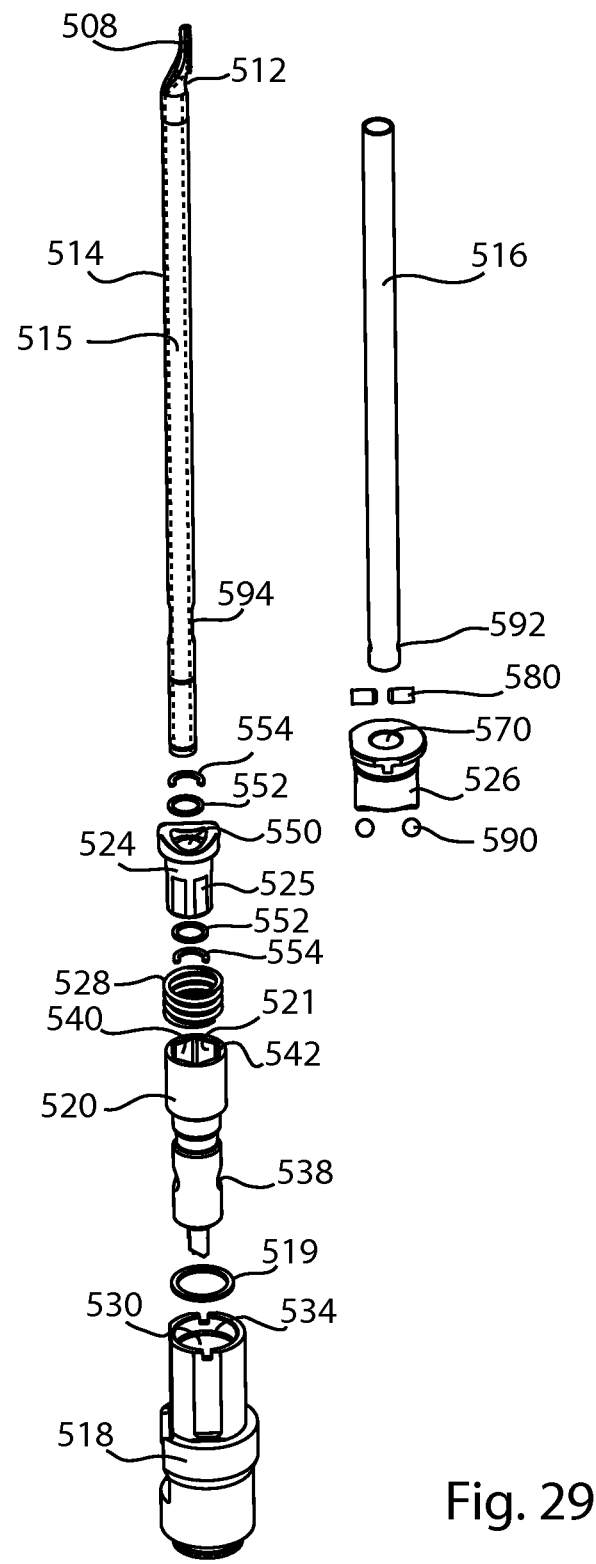
FIG. 29 is an exploded view of the rasping system of FIG. 27.
Figure 30:
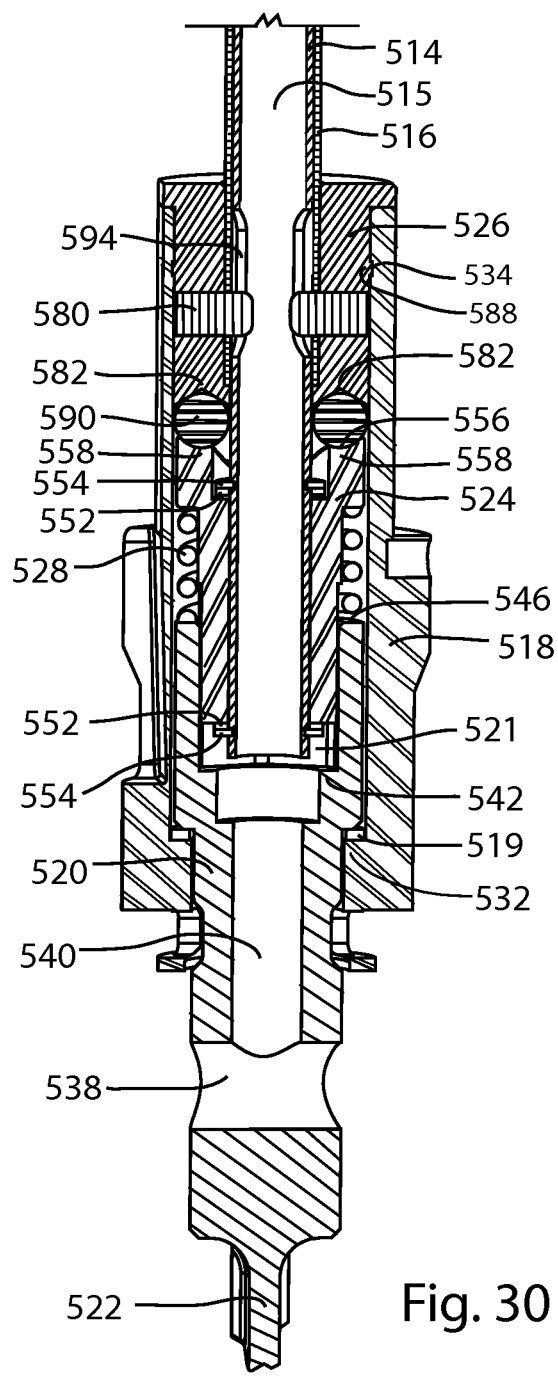
FIG. 30 is a cross-sectional view of the handle and shaft portions of the reciprocating rasping system of FIG. 27 with a tissue removal member in an retracted position.
Figure 31:
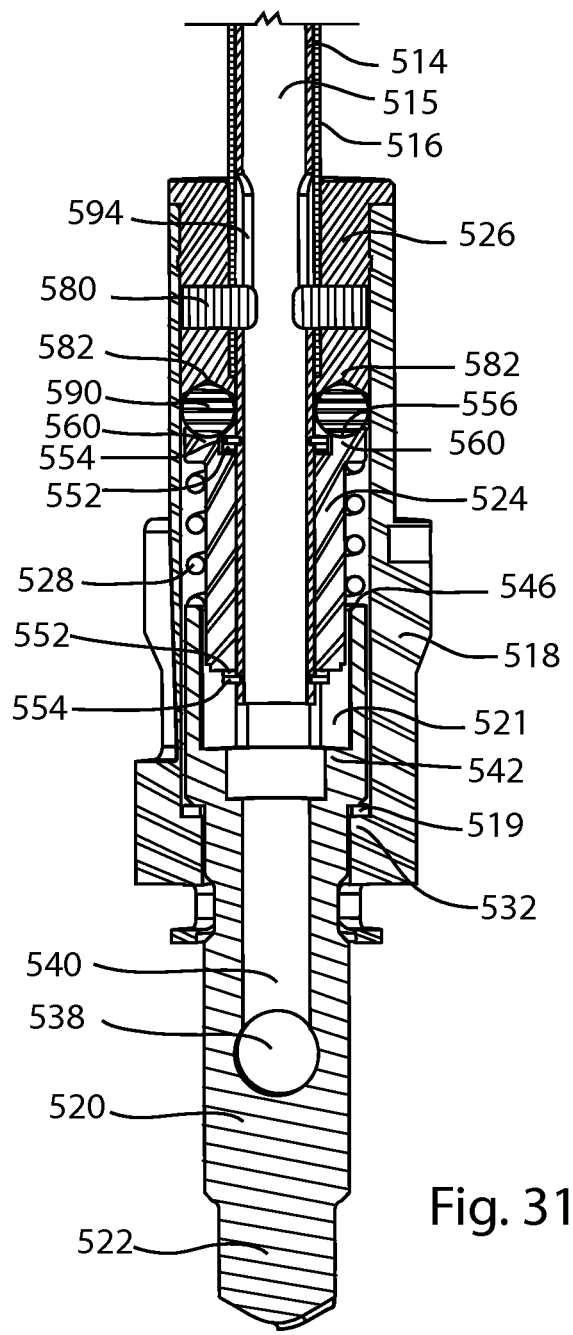
FIG. 31 is a cross-sectional view of the handle and shaft portions of the reciprocating rasping system of FIG. 27 with a tissue removal member in an extended position.

FIGS. 28A and 28B show side and bottom views of rasp system 500, respectively. The outer housing 518 is not shown so that the juxtaposition of the component parts may be seen, relative to longitudinal system axis 505. FIG. 29 is an exploded isometric view of the system. With reference to these drawings, system 500 will be described in a generally proximal to distal sequence. At the proximal end of the assembled system, hub 520 includes a driver connection 522, which may be a tab shaped to be coupled with a driver in a powered handpiece, as described earlier with reference to system 100. When hub 520 is received in housing 518 as in FIG. 27, a coupler washer 519 located between hub 520 and housing 518 promotes free rotation of the hub relative to the housing, thus reducing friction and potentially preventing melting of the two components. Hub 520 further includes a connection feature 521 shaped to receive the cam 524 in a sliding connection, wherein cam 524 is partially captured in hub 520 so that it is rotatably carried with the rotation of hub 520 about longitudinal axis 505, but can also reciprocate along axis 505. The connection feature 521 may be a hex feature, and cam 524 has a corresponding connection feature 525. Inner shaft 514 extends proximally through cam 524, and is slidably engaged with cam 524 so that it does not rotate with cam 524, but is reciprocatively carried with cam 524 between a proximal, or retracted, and a distal, or extended, position. Distal to cam 524, fixed cam 526 may be connected to outer sleeve 516, and may be rigidly connected to housing 518. As cam 524 rotates, cam and cam follower surfaces on cam 524 and fixed cam 526 cooperate to convert the rotary motion of the hub 520 and cam 524 to reciprocating movement of the cam 524 and inner shaft 514. At least one ball bearing 590 may be positioned between the cam and cam follower surfaces, and may reduce friction between the surfaces. A spring 528 is positioned between hub 520 and cam 524, and the spring bias of spring 528 returns the cam 524, inner shaft 514 and rasp head 508 to the distal position. It is appreciated that in other embodiments, the relative sequence of the system components may vary to accomplish the same objectives. For example, in another embodiment the relative positions of the cam 524 and fixed cam 526 may be reversed, or the location of the spring 528 may differ. Referring to FIGS. 30 and 31, longitudinal cross-sectional views show the handle portion 506 of system 500 in the retracted and extended positions, respectively. With reference to FIGS. 29-31, system 500 is described in more detail. Housing 518 has a generally elongated tubular shape, and may include external engagement features such as slots, grooves, tabs or faces shaped for engagement with a specific powered handpiece. Housing 518 may be referred to as an adapter body. A housing bore 530 formed in housing 518 is smooth sided to allow free rotation of hub 520 and cam 524 within the bore, and free reciprocation of cam 524. A housing shoulder 532, formed as a step in bore 530, provides a seat for coupler washer 519, and retains hub 520 partially within the housing. Near the distal end of housing 518, a housing groove 534 may be formed in bore 530 for retention of fixed cam 526.

Hub 520 has a generally elongated, and partially tubular form. A transverse bore 538 is formed toward a proximal end of the hub, and a longitudinal bore 540 is formed from a distal end of the hub, extending longitudinally into a portion of the hub and opening into the transverse bore 538. The longitudinal 540 and transverse 538 bores form a segment of the suction pathway. The inside diameter of the longitudinal bore 540 is stepped, and in other embodiments may be tapered. One step forms a first hub shoulder 542, which may provide a proximal stop for reciprocation of cam 524. Another step forms a second hub shoulder 544, which may provide a proximal stop for reciprocation of inner shaft 514. A distal portion of longitudinal bore 540 is connection feature 521, which may be a hex as previously set forth. A distal end 546 of the hub 520 provides a platform or seat for spring 528.

Figures 32A, 32B, 32C:
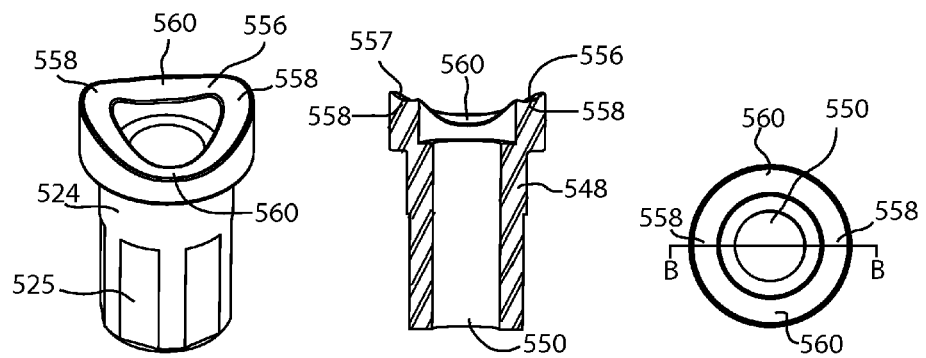
FIG. 32A is an isometric view of a rotatable cam of the system of FIG. 27.
FIG. 32B is a cross-sectional view of the rotatable cam of FIG. 32A taken along line B-B.
FIG. 32C is an end view of the rotatable cam of FIG. 32A.

Cam 524 has a generally elongated tubular body 548, and is sized so that a proximal portion is received in longitudinal bore 540 of hub 520. When assembled, the cam 524 may be entirely enclosed in housing 518. A cam bore 550 extends longitudinally through the length of the cam body 548, and is sized to receive inner shaft 514. When inner shaft 514 is positioned in cam bore 550, a washer 552 and snap ring 554 are placed around inner shaft 514 at each end of cam 524, the snap rings 554 fitting into grooves formed in the inner shaft 514 to retain cam 524 in a fixed longitudinal position relative to inner shaft 514, while simultaneously allowing free rotation of cam 524 relative to shaft 514. Further detail of cam 524 is seen in FIGS. 32A-C. A portion of the outer surface of cam 524 forms connection feature 525, which is shaped to complementarily engage connection feature 521 on hub 520. Although hex shaped connection features are shown in the figures, it is appreciated that in other embodiments the connection features could comprise other complementary shapes. Toward the distal end of cam 524, cam surface 556 is formed on cam 524. Cam surface 556 is generally annular or circular and undulating, forming two protruding lobes, or high points 558 alternating with two low points 560. The high and low points are evenly distributed; the high points at 180° from each other and the low points at 180° from each other, and the low points 90° from each high point. It is appreciated that in other embodiments of the invention, the cam surface 556 could have one high and one low point; or multiple high and low points. The cam surface 556 may be recessed, forming a grooved track 557, which may be hemispherically grooved. The annular cam surface 556 may also be radially sloped such than the inner diameter of the annulus is lower than the outer diameter at any radial cross-section of the cam surface, as seen in FIG. 32B.

Figures 33A, 33B, 33C:
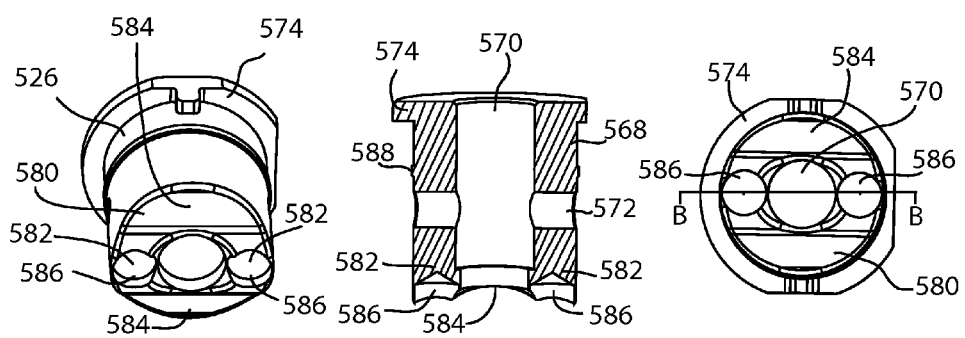
FIG. 33A is an isometric view of a fixed cam of the system of FIG. 27.
FIG. 33B is a cross-sectional view of the fixed cam of FIG. 33A taken along line B-B.
FIG. 33C is an end view of the fixed cam of FIG. 33A.

FIGS. 33A-C show further detail of fixed cam 526. Fixed cam 526 has a generally tubular body 568, and includes a fixed cam bore 570 which extends longitudinally through the length of the fixed cam. The bore 570 is sized to receive outer sleeve 516 in a press fit engagement. At least one slot 572 extends through body 568, and is shaped to receive a pin or screw for fixing the position of outer sleeve 516 relative to the fixed cam 526. Toward the distal end of the fixed cam 526, a rim 574 projects from the cam body 568. At the proximal end of the fixed cam 526 is formed a fixed cam surface 580. Fixed cam surface 580 is generally circular and undulating, forming two protruding lobes, or high points 582 alternating with two low points 584. The high and low points are evenly distributed; the high points at 180° from each other and the low points at 180° from each other, and the low points 90° from each high point. It is appreciated that in other embodiments of the invention, the fixed cam surface 580 could have one high and one low point; or multiple high and low points, and that the high and/or low points may be unevenly distributed. At each of the two high points 582, a recessed dimple 586 is formed. The dimples 586 are shaped to partially receive bearings 590.

With reference to FIGS. 27-31, when assembled in system 500, fixed cam 526 is at least partially enclosed by housing 518, and is displaced from hub 520. A rib 588 may be formed on the fixed cam body 568, shaped to fit into housing groove 534. Pins 580 extend through slots 572, through openings 592 in outer sleeve 516, and into elongated slots 594 in inner shaft 514. The pins and slots form a keyway system which fixes the positions of fixed cam 526 and outer sleeve 516 relative to one another, and forms a sliding connection to inner shaft 514. The elongated slots 594 allow inner shaft 514 to reciprocate relative to outer sleeve 516, constrained by pins 580.

In one method of use, handle portion 506 is fitted into a powered handpiece, with driver connection 522 engaging with a rotating driver in the handpiece. When powered on, hub 520 rotates, and cam 524 rotates with hub 520. As cam 524 rotates, cam surface 556 rotates, bearing against bearings 590 retained in dimples 586 of fixed cam 526. During rotation, when the cam high points 558 are aligned with fixed cam high points 582, inner shaft 514 and rasp head 508 are pulled proximally to a retracted position by cam 524, as seen in FIG. 30. Spring 528 is compressed between cam 524 and hub distal end 546. As rotation continues, cam low points 560 become aligned with fixed cam high points 582, and inner shaft 514 and rasp head 508 are pushed distally to an extended position by the spring bias of spring 528, as seen in FIG. 31. In this embodiment, two such retraction-extension cycles are completed with each full rotation of the hub 520. During the cycles, bearings 590 are rotated within dimples 586 as cam surface 556 spins against the bearings. The hemispherical shapes of the cam surface 556 and fixed cam surface 580, and the complementary spherical shape of bearings 590 may provide continual surface contact between the bearings and the opposing cam surfaces.

Additional embodiments of a reciprocating surgical instrument include tissue removal members having working ends which comprise cutting heads with jaw members, which may be referred to as jaws, which cooperate to provide biting or nipping action for removal of targeted tissue. The reciprocating motion allows the cutting head of these instruments to move between open and closed positions. In the open position, the jaw members may be spaced apart, and may be distally displaced from the instrument. In the closed position, the jaw members may abut one another, and may be pulled toward the instrument. The open jaw members may be urged around the targeted tissue so that when the jaws move to the closed position, they grasp and/or sever the tissue. Suction may be provided to remove the severed tissue. An opening to a suction path may be located between the jaws.

FIGS. 34A-38E illustrate several embodiments of working ends of reciprocating surgical instrument systems. In these embodiments, each working end may comprise a cutting head which includes the distal portions of inner shaft 514 and outer sleeve 516, as set forth in the description of system 500. Although the proximal remainder of the shaft portion 504, and the handle portion 506 are not shown, they are understood to be present in the total instrument. In the figures, slashed lines demarcate the edge of the illustrated portion of the embodiment.

Each of the embodiments of FIGS. 34A-38E is actuatable by reciprocating translational motion of inner shaft 514 longitudinally along rotation axis 505, between retracted and extended positions, as set forth in the description of system 500. In these embodiments, reciprocating motion functions to open and close jaw members positioned at or near the distal ends of inner shaft 514 and outer sleeve 516. Each cutting head may be formed integrally with, or coupled to, inner shaft 514 and outer sleeve 516. It is also appreciated that in alternative embodiments the cutting head portions described below may be head portions of instrument system 100, and correspondingly include distal portions of inner shaft 114 and outer sleeve 116. Suction openings and suction pathways disclosed in FIGS. 34A-38E may connect with suction pathways disclosed in instrument systems 100 or 500.

Figure 34A:
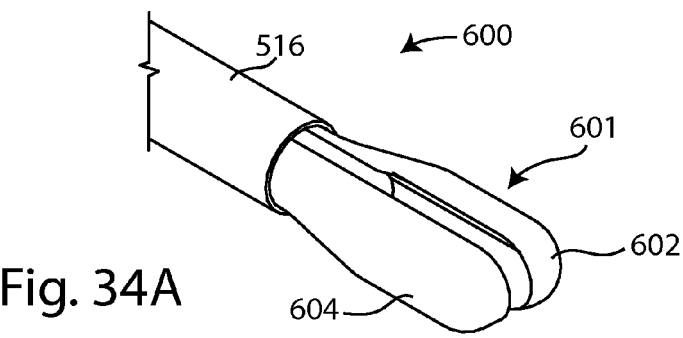
FIG. 34A is an isometric view of a distal portion of a tissue removal member with a cutting head having opposing jaws.
Figure 34B:
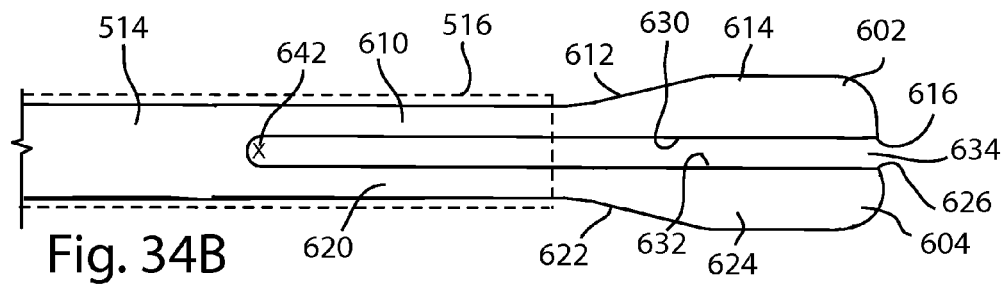
FIG. 34B is a side view of the tissue removal member of FIG. 34A in an open position, with a dashed line representing an outer sleeve.
Figure 34C:
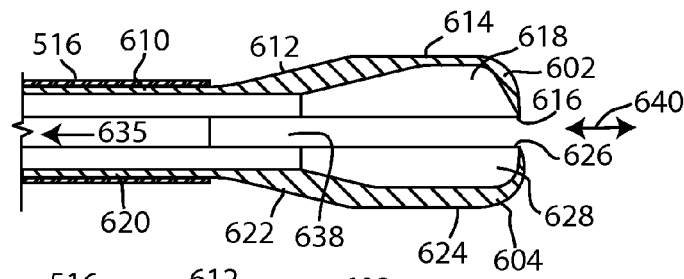
FIG. 34C is a cross-sectional view of the tissue removal member of FIG. 34B.
Figure 34D:
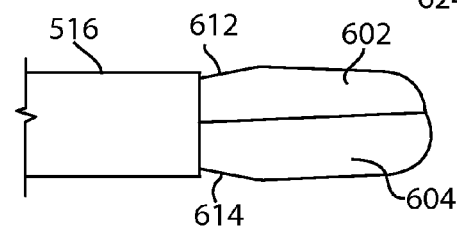
FIG. 34D is a side view of the tissue removal member of FIG. 34A in a closed position.
Figure 34E:
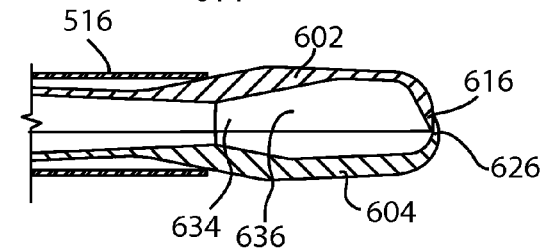
FIG. 34E is a cross-sectional view of the tissue removal member of FIG. 34D.

FIGS. 34-34E depict a tissue removal member 600 comprising a working end with a cutting head 601 having a first jaw member 602 and an opposing second jaw member 604. The jaw members 602, 604 may be a forked distal extension of inner shaft 514. Each jaw member 602, 604 is of a general half-pipe shape, terminating distally in a cutting edge. First jaw member 602 includes a first shaft portion 610, a tapered portion 612, and a mouth portion 614 which terminates in a first terminal edge 616. Correspondingly, second jaw member 604 includes a first shaft portion 620, a tapered portion 622, and a mouth portion 624 which terminates in a second terminal edge 626. The mouth portions of each jaw are hollowed out, forming a first mouth alcove 618 interior to the first mouth portion 614, and a second mouth alcove 628 interior to the second mouth portion 624. A first lateral edge 630 extends the length of the first jaw member and a second lateral edge 632 extends the length of the second jaw member. Any of the terminal edges 616, 618 and lateral edges 630, 632 may be sharpened and may be a cutting edge. A suction opening 634 may be provided between the first and second jaws 602, 604, and leads into a suction pathway 635 extending proximally through the shaft 514.

Cutting head 601 is actuable between an open position in which first jaw member 602 is spaced apart from second jaw member 604, as seen in FIGS. 34A-C; and a closed position in which at least the first terminal edge 616 abuts or overlaps the second terminal edge 626, as seen in FIGS. 34D-E. In the open position, a gap 638 is formed between the lateral edges 630, 632. In the closed position, lateral edges 630, 632 may also abut, or overlap each other. In the closed position, the first and second mouth alcoves 618, 628 may abut or overlap to form an open three dimensional space or cavity 636.

Actuation of cutting head 600 between the open and closed positions is brought about by the reciprocating motion of inner shaft 514 along rotation axis 505 as described previously with reference to FIGS. 30 and 31, and indicated by direction arrow 640. As seen in FIGS. 34D-E, as inner shaft 514 is pulled proximally, jaw tapered portions 612 and 622 slidingly engage with and are constrained by the distal end of outer sleeve 516, urging jaws 602, 604 toward one another to the closed position, pivoting about pivot axis 642 (FIG. 34B). As seen in FIGS. 34 A-C, as inner shaft 514 is biased distally, jaws 602, 604 are urged apart to the open position. In use, cutting head 601 may be moved toward targeted tissue until the targeted tissue is received in gap 638. Upon actuating of the cutting head to the closed position, the targeted tissue will be captured in between the terminal edges 616, 626 and/or portions of lateral edges 630, 632. The tissue may be enclosed in cavity 636. The edges 616, 626 and/or 630, 632 may cooperate to cut or sever the tissue between them in the first or subsequent reciprocation cycles of the instrument. Suction may remove the severed tissue proximally through the suction opening 634 and into the suction pathway 635.

In some embodiments, the lengths and/or angles of the tapered portions 612, 622 may vary together or independently to vary the size of gap 638 when the jaws are in the open position. In some embodiments, only one jaw may include a tapered portion. The length, width and height of the jaws 602, 604 may vary together or independently as desired; for example for the type and amount of tissue to be treated. In some embodiments, teeth or serrations may be present on any of the jaw edges.

FIGS. 35A-D depict a tissue removal member 650 comprising a working end with a cutting head 651 having a first jaw member 652 and an opposing second jaw member 654. Cutting head 651 is shaped as a pair of scissors, with jaw members 652, 654 shaped as the blades. First jaw member 652 includes an engagement segment 658 and a blade segment 660, which may be distal to the engagement segment.

Blade segment 660 includes a blade edge 661. Second jaw member 654 may be a mirror image of first jaw member 652, and includes an engagement segment 662 and a blade segment 664 having a blade edge 665. Each engagement segment lies at an angle relative to its respective blade segment. A pin 666 passes through the engagement segments 658, 662 to couple them together, and defines a pivot axis 667. The pin 666 also passes through the outer sleeve 516 to couple the jaw members 652, 654 to the outer sleeve. The jaw members may be said to be carried by or on the outer sleeve. The engagement segments 658, 662 may be thicker than the blade segments 660, 664 to provide strength, leverage and stability to the blades during the scissoring action of the cutting head. Jaw members 652, 654 may pivot relative to one another about the pivot axis 667 between an open position in which the blade segments 660, 664 are spaced apart from one another as seen in FIGS. 35B and 35D, and a closed position in which the blade segments abut or overlap one another as seen in FIGS. 35A and 35C. The proximal end of inner shaft 514 includes a first projection 670 and a second projection 672, the projections protruding inwardly from the outer wall of the shaft and opposing one another. A length of each engagement segment 658, 662 is captured between the two projections 670, 672.

Actuation of cutting head 651 between the open and closed positions is brought about the reciprocating motion of inner shaft 514 along rotation axis 505 as described previously and indicated by direction arrow 640. As seen in FIGS. 35B and 35D, as inner shaft 514 is pulled proximally, the proximal ends of the engagement segments 658, 662 are urged toward one another by contact with the opposing projections 670, 672, causing the blade segments 660, 664 to lever apart. When inner shaft 514 is biased distally as in FIGS. 35A and 35C, the projections 670, 672 move distally to allow the proximal ends of the engagement segments 658, 662 to scissor apart from one another; blade segments 660, 664 are moved toward one another to abut and/or overlap one another. Tissue positioned between the blade edges 661, 665 in the open position may be cut or severed as the blade segments are moved to the closed position. The cutting head 651 may operate as a pair of scissors or shears, and may make a clean unidirectional cut into a body of tissue.

A suction opening 674 may be formed at the distal ends of the outer sleeve 516 and inner shaft 514, the opening provided between the projections 670, 672. When suction force is applied, cut tissues, liquids and other debris may be removed proximally through the suction opening and into a suction pathway 676.

In some embodiments, the lengths, widths and/or thicknesses of the first and second jaw members 652, 654 may vary, as may the angle between each blade's engagement segment and blade segment. In some embodiments, teeth or serrations may be present on any of the blade edges. In an embodiment, the position of one jaw member may be stationary and not pivotable, while the other jaw member pivots about the pivot axis to provide the cutting action. In an embodiment, the jaw members may be carried by the inner shaft, while the constraining projections are formed on the outer sleeve.

Figure 36A:
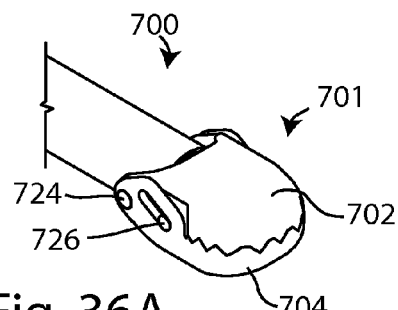
FIG. 36A is an isometric view of a distal portion of a tissue removal member with a cutting head having opposing jaws, the jaws in a closed position.
Figure 36B:
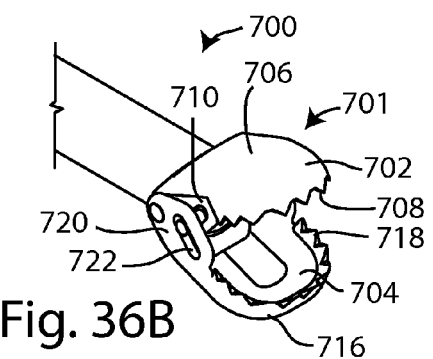
FIG. 36B is an isometric view of the tissue removal member of FIG. 35A with the jaws in an open position.

FIGS. 36A-E illustrate a tissue removal member 700 having a working end with a clamshell-like cutting head 701 with a first jaw member 702, which may be an upper jaw, and a second jaw member 704, which may be a lower jaw. The cutting head 701 is actuable between an open position in which the jaw edges are spaced apart from one another, and a closed position in which the jaw edges abut, in order to capture and sever tissue between the jaws. First jaw 702 has a shell-like shape, with a convex outer wall 706 bounded distally by a rounded cutting edge 708. A hinge section 710 is present on either lateral side of the convex outer wall 706, and includes a hole 711 and a slot 712. Second jaw 704 is also shell-like, with a convex outer wall 716 bounded distally by a rounded cutting edge 718. A hinge section 720 is present on either lateral side of the convex outer wall 716, and includes a hole 721 and a slot 722. The second jaw member 704 may be slightly wider than the first jaw member 702, allowing the hinge sections 710 of the first jaw member 702 to nest inside the hinge sections 720 of the second jaw member 704, as seen in FIGS. 36A and 36B.

The tissue removal member 700 further includes the distal end of outer sleeve 516, on which two pegs 724 are formed, projecting perpendicularly outward from the sleeve, providing an attachment feature for the first and second jaw members. The two pegs 724 are coaxially aligned and define a pivot axis 725. The first and second jaw members are pivotably mounted on the outer sleeve pegs 724, with the pegs extending through holes 711 and 721 of the first and second jaw members, respectively. The distal end of the inner shaft 514 includes two opposing holes through which a pin 726 extends. The pin 726 further extends through the slots 712 in the hinge sections 710 of the first jaw member 702, and through the slots 722 in the hinge sections 720 of the second jaw member 704. A suction opening 728 is formed by the distal end of inner shaft 514, and is positioned between the first and second jaw members.

Figure 36C:
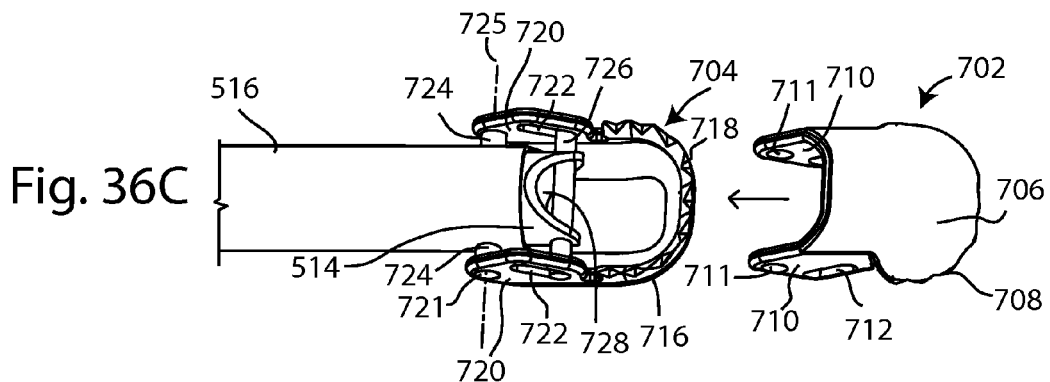
FIG. 36C is an isometric partially exploded view of the tissue removal member of FIG. 36A with a first jaw member moved aside to show inner detail.
Figure 36D:
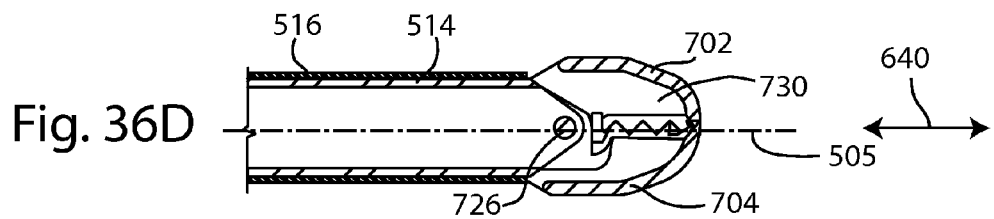
FIG. 36D is a side cross-sectional view of the tissue removal member of FIG. 36A.
Figure 36E:
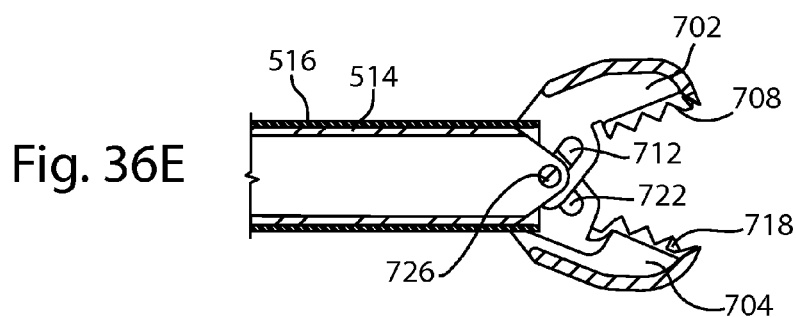
FIG. 36E is a side cross-sectional view of the tissue removal member of FIG. 36B.

Cutting head 701 is actuated by reciprocation of inner shaft 514 along axis 505 within outer sleeve 516 between the retracted and extended positions as described previously. As seen in FIGS. 36B and 36E, when inner shaft 514 is retracted, pin 726 is pulled proximally, and traverses slots 712, 722 proximally to move jaw members 702, 704 to the open position. When inner shaft 514 is biased distally relative to outer sleeve 516 as seen in FIGS. 36A, 36C and 36D, pin 726 traverses slots 712, 722 distally to move the jaw members to the closed position. In the closed position, an enclosed cavity 730 may be formed between the first and second jaw members. During actuation both jaw members 702, 204 pivot about pivot axis 725, which may be perpendicular to rotation axis 505. Tissue positioned between the cutting edges 708, 718 in the open position may be captured in the cavity 730 and/or severed as the jaw members 702, 704 are moved to the closed position. In the closed position, the cutting edges 708, 718 may meet edge on edge, or one may overlap the other to sever the tissue. Severed tissue may be suctioned away through the suction opening 728.

In some embodiments, the lengths, widths and/or heights of the first and second jaw members 702, 704 may vary. In some embodiments, teeth or serrations may be present on any of the cutting edges, or the edges may be smooth. In an embodiment, the position of one jaw member may be stationary and not pivotable, while the other jaw member pivots about the pivot axis to provide the cutting action. In an embodiment, the second jaw member may nest inside the first jaw member.

FIGS. 37A-E illustrate a tissue removal member 750 having a working ends with a duckbill-shaped cutting head 751 with a first jaw member 752, which may be an upper jaw, and a second jaw member 754, which may be a lower jaw. The cutting head 751 is actuable between an open position in which the jaw edges are spaced apart from one another, and a closed position in which the jaw edges abut, in order to capture and sever tissue between the jaws in a biting action. First jaw member 752 is coupled to inner shaft 514, and is pivotable about a pivot axis relative to second jaw member 754, which is fixed to outer sleeve 516 and remains stationary.

First jaw member 752 is duckbill-shaped, and includes a convex wall 756 partially bounded by a curved cutting edge 758, which may be beveled, honed or sharpened. A hinge section 760 on each side of the jaw member includes first and second holes 762, 764. The interior of the jaw member 752 is concave. Second jaw member 754 includes an attachment section 768, a hinge section 770 on either side of the second jaw member, and a jaw section 772. The jaw section 772 terminates in a rounded cutting edge 774, which also may be beveled, honed or sharpened. Attachment section 768 may surround outer sleeve 516 and rigidly attach the second jaw member 754 to the outer sleeve. The hinge sections 770 each include a hole 776, and a ramp 778. The second jaw member 754 may be integrally formed as a portion of outer sleeve 516. The distal end of inner shaft 514 includes a pair of opposed slots 780. A first pin 782 extends through the second jaw member holes 776 and the first jaw member holes 764, coupling the first jaw member to the second jaw member, and defining a pivot axis about which first jaw member 752 may pivot. A second pin 784 extends through the first jaw member holes 762 and the inner shaft slots 780. The open distal end of inner shaft 514 forms a suction opening 786.

Figure 37A:
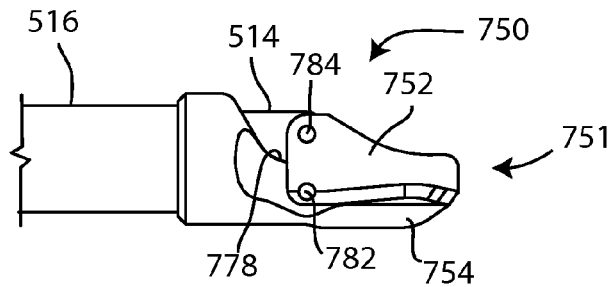
FIG. 37A is a side view of a distal portion of a tissue removal member with a cutting head having opposing jaws, the jaws in a closed position.
Figure 37B:
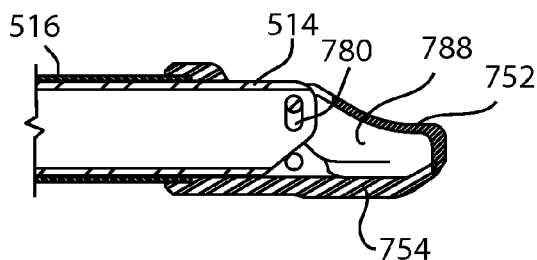
FIG. 37B is a cross-sectional side view of the tissue removal member of FIG. 37A.
Figure 37C:
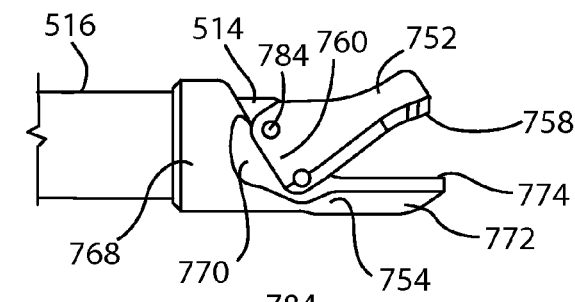
FIG. 37C is a side view of the tissue removal member of FIG. 37A with the jaws in an open position.
Figure 37D:
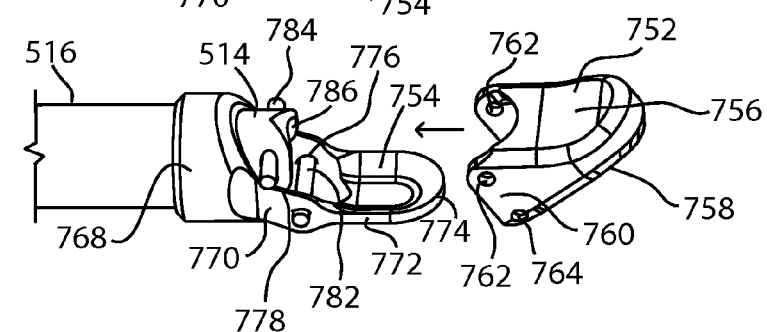
FIG. 37D is an isometric partially exploded view of the tissue removal member of FIG. 37C with a first jaw member moved aside to show inner detail.
Figure 37E:
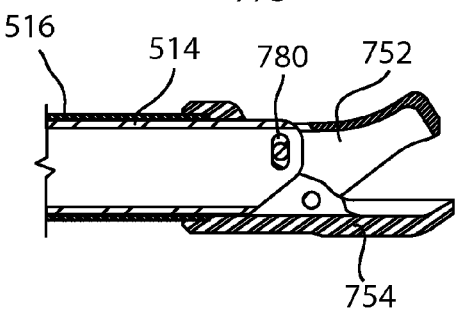
FIG. 37E is a side cross-sectional view of the tissue removal member of FIG. 37C.

Cutting head 751 is actuated by reciprocation of inner shaft 514 within outer sleeve 516 between the retracted and extended positions as described previously with regard to other embodiments. As seen in FIGS. 37C-E, when inner shaft 514 is retracted, second pin 784 is pulled proximally, and pulls first jaw member 752 proximally. First jaw member 752 pivots about first pin 782, and the jaws are moved to the open position. When inner shaft 514 is biased distally relative to outer sleeve 516 as seen in FIGS. 37A and 37B, pin 784 traverses slots 780 and pushes first jaw member 752 distally to move the jaw members into the closed position. In the closed position, a cavity 788 is formed between the first and second jaw members 752, 754. The range of motion of first jaw member 752 may be constrained by the extent of slot 780, and also contact with ramp 778 and second jaw member 754. Tissue positioned between the cutting edges 758, 774 in the open position may be captured in the cavity 754 and/or severed as the jaw members 752, 754 are moved to the closed position. In the closed position, the cutting edges 758, 774 may meet edge on edge, or one may overlap the other to sever the tissue. Severed tissue may be suctioned away through the suction opening 786.

In some embodiments, the lengths, widths and/or heights of the first and second jaw members 752, 754 may vary. In some embodiments, teeth, scalloping, or serrations may be present on any of the cutting edges, or the edges may be smooth. In an embodiment, the jaw members may be reversed such that the first jaw member 752 is stationary and not pivotable, while the second jaw member 754 about the pivot axis to provide the cutting action. In an embodiment, the second jaw member may nest inside the first jaw member. In some embodiments, the jaw members may be squared off, pointed, tapered, or another shape.

FIGS. 38A-E illustrate a tissue removal member 800 having a working ends with a spherically shaped cutting head 801 with a first jaw member 802, which may be an upper jaw, and a second jaw member 804, which may be a lower jaw. The cutting head 801 is actuable between an open position in which the jaw edges are spaced apart from one another, and a closed position in which the jaw edges abut, in order to capture and sever tissue between the jaws. Both the first and second jaw members 802, 804 are pivotally coupled to outer sleeve 516.

First jaw member 802 includes a mouth section 806 and an attachment section 808. The mouth section 806 is generally hemispherical, and terminates in a cutting edge 810. Cutting edge 810 may be a flat surface. The attachment section 808 extends proximally from the mouth section, and is forked into a pair of spaced apart tabs 812. A hole 814 perforates each tab 812. Second jaw member 804 includes a mouth section 816 and an attachment section 818. The mouth section 816 is generally hemispherical, and terminates in a cutting edge 820. Cutting edge 820 may be beveled or angled. The attachment section 818 extends proximally from the mouth section, and is forked into a pair of spaced apart tabs 822. A hole 824 perforates each tab 822. Second jaw member tabs 822 may be spaced apart wider than first jaw member tabs 812, so that the attachment section 808 of first jaw member 802 nests slightly inside the attachment section 818 of second jaw member 804 when assembled.

The distal end of outer sleeve 516 includes a pair of opposed pegs 830 which project inwardly. The pegs 830 may be formed integrally with outer sleeve 516 or may be inserted in holes in outer sleeve 516. Inner shaft 514 terminates distally in a pair of opposed cutouts 831. Each cutout 831 comprises two niche sections 832 and two waist sections 834. When properly assembled, the attachment sections 808, 818 of the jaw members are partially received in the cutouts 832 of the inner shaft 514. The holes 814, 824 are pivotably mounted or carried on the pegs 830 of the outer sleeve 516. The open distal end of the inner shaft forms a suction opening 836.

Figure 38A:
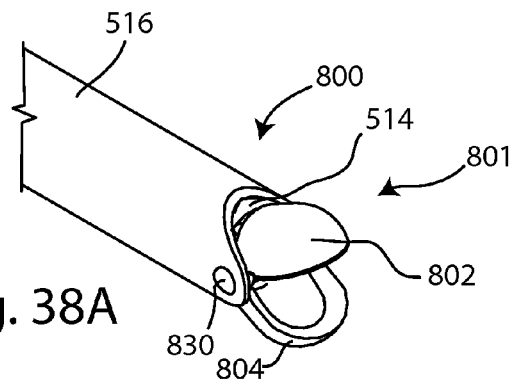
FIG. 38A is an isometric view of a distal portion of a tissue removal member with a cutting head having opposing jaws, the jaws in an open position.
Figure 38B:
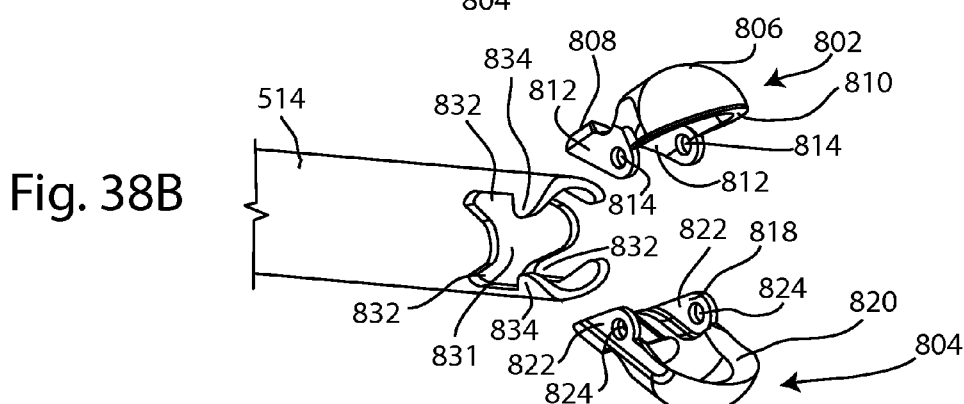
FIG. 38B is an isometric exploded view of an inner shaft and first and second jaw members of the tissue removal member of FIG. 38A.
Figure 38C:
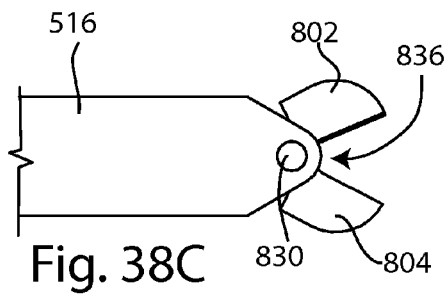
FIG. 38C is a side view of the tissue removal member of FIG. 37A.
Figure 38D:
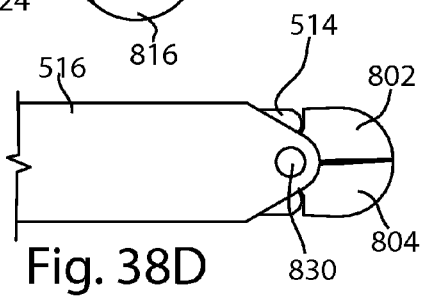
FIG. 38D is a side view of the tissue removal member of FIG. 37A with the jaws in a closed position.
Figure 38E:
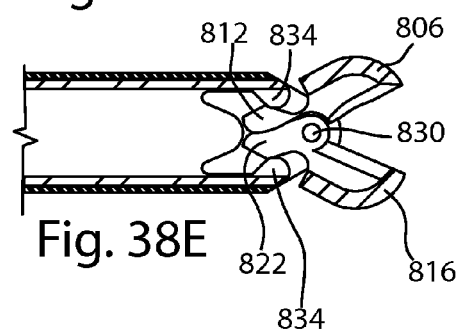
FIG. 38E is a cross-sectional side view of the tissue removal member of FIG. 38C.
Figure 38F:
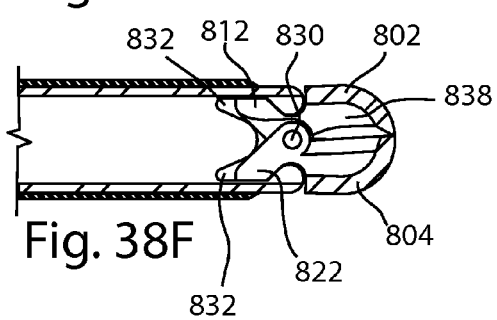
FIG. 38F is a cross-sectional side view of the tissue removal member of FIG. 38D.

Cutting head 801 is actuated by reciprocation of inner shaft 514 within outer sleeve 516 between the retracted and extended positions as described previously. As seen in FIGS. 38A, 38C and 38E, when inner shaft 514 is retracted, tabs 812 and 822 are urged toward one another by contact with opposing waist sections 834, and mouth sections 806, 816 spread apart from one another, pivoting around pegs 830. When inner shaft 514 is moved distally as in FIGS. 38D and 38F, tabs 812, 822 are received in niches 832 and mouth sections 806, 816 are urged together until cutting edges 810, 820 meet and/or overlap. In this closed position, a cavity 838 is formed between the first jaw member 802 and the second jaw member 804. Tissue may be captured and/or severed between the first and second jaw member in a biting motion, and may be removed proximally through the suction opening 836.

In some embodiments, the lengths, widths and/or heights of the first and second jaw members 802, 804 may vary. In some embodiments, teeth, scalloping, or serrations may be present on any of the cutting edges, or the edges may be smooth. In an embodiment, the second jaw member may nest inside the first jaw member. In some embodiments, the jaw members may be elongated, squared off, pointed, tapered, or another shape. In an embodiment, the position of one jaw member may be stationary and not pivotable, while the other jaw member pivots about the pivot axis to provide the cutting action.

It is appreciated that the instrument working end and shaft portions of any of the tissue removal members disclosed in FIGS. 34A through 38F and the accompanying specification may be sized to allow access to small and/or tight portions of anatomy. These instruments may permit precise trimming or nibbling and internalized removal of tissues, in contrast with instruments which may tear away large portions of tissue and do not provide internal suction capable of removing the large portions of tissue. Uses for these instruments may include, but are not limited to: chondroplasty, meniscectomy, plastic surgery, and ACL repair/replacement. The cutting head component parts may include metal, metal alloys or ceramics, and may incorporate non-metal materials such as hard plastics or polymers, for example to provide reduced friction at pivot points. Coatings or surface treatments may also be included to provide reduced friction.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, any rasping or biting head may be combined with any handle portion or driving hub configuration. Similarly, suction, RF ablation, infusion, and/or imaging capability may be included with any rasping or biting system disclosed herein. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A tissue removal device for being driven by a powered rotary handpiece, the tissue removal device comprising:
    a longitudinal axis;
    a motion conversion mechanism having a rotating member;
    a tissue removal member having a shaft and a cutting head, the shaft coupled in sliding contact with the rotating member, the cutting head including a first jaw member coupled to a second jaw member, the cutting head actuable between an open position in which a first edge on the first jaw member is spaced apart from a second edge on the second jaw member and a closed position in which the first edge abuts the second edge in order to sever tissue between the first and second edges;
    wherein when the rotating member is rotated about a rotation axis, the motion conversion mechanism is configured to urge a translational motion of the shaft along the rotation axis, wherein the translational motion consists of a reciprocating translation between a first retracted position and a second extended position; and,
    wherein the motion conversion mechanism comprises a first cam member having a first cam surface, a second cam member having a second cam surface, wherein the second cam surface is configured to rotate relative to the first cam surface about the longitudinal axis.

2. The tissue removal device of claim 1, wherein at least one of the first and second jaw members is configured to pivots about a pivot axis to move the cutting head between the open and closed positions.

3. The tissue removal device of claim 2, wherein both of the first and second jaw members are configured to pivot about the pivot axis to move the cutting head between the open and closed positions.

4. The tissue removal device of claim 2, wherein the pivot axis is perpendicular to the longitudinal axis.

5. The tissue removal device of claim 1, wherein the tissue removal member further comprises a hollow sleeve through which the shaft extends.

6. The tissue removal device of claim 5, wherein at least one of the first and second jaw members is carried on the hollow sleeve.

7. The tissue removal device of claim 5, wherein the shaft comprises a suction opening adjacent the cutting head and a suction pathway extending proximally from the suction opening.

8. The tissue removal device of claim 7, wherein the suction opening is positioned between the first and second jaw members.

9. The tissue removal device of claim 5, wherein the shaft is coupled in direct sliding contact with the rotating member.

10. The tissue removal device of claim 1, wherein the shaft is configured to be translated between the retracted and extended positions and thereby control an actuation of the cutting head between the open and closed positions.

11. The tissue removal device of claim 10, wherein the cutting head is in the open position when the shaft is in the extended position and in the closed position when the shaft is in the retracted position.

12. The tissue removal device of claim 10, wherein the cutting head is in the open position when the shaft is in the retracted position and in the closed position when the shaft is in the extended position.

13. The tissue removal device of claim 1, wherein at least one of the first and second edges comprises a plurality of teeth to provide a serrated cutting surface.

14. The tissue removal device of claim 1, wherein a cavity is formed between the first and second jaw members when the cutting head is in the closed position.

15. The tissue removal device of claim 1, wherein a spherical bearing is positioned between the first and second cam surfaces.

16. A system for tissue removal, the system comprising:
    a rotatable hub adapted to be rotated about a rotation axis by a powered rotary handpiece;
    the tissue removal member having a shaft and a working end, the shaft coupled in sliding contact with the rotating member, the working end having a first jaw member and a second jaw member positioned opposite the first jaw member; and a motion conversion mechanism, the motion conversion mechanism comprising the rotatable hub, a first cam member, a second cam member, and a spherical bearing positioned between the first and second cam members, the second cam member joined to the rotatable hub;

wherein, during rotation of the rotatable hub about the rotation axis, the second cam is configured to rotate relative to the first cam, and the motion conversion mechanism is configured to urge a reciprocal motion of the shaft along the longitudinal axis, wherein the motion of the shaft is configured to urge at least one of the first and second jaw members to pivot relative to the other jaw member in order to capture tissue between the first jaw member and the second jaw member.

17. The system of claim 16, wherein the first cam member is configured to be stationary and the second cam member is configured to rotates relative to the first cam member about the longitudinal axis.

18. The system of claim 17, wherein the first cam member comprises an annular first cam surface and the second cam member comprises an annular second cam surface shaped complementarily to the first cam surface.

19. The system of claim 18, wherein the spherical bearing is configured to directly contact the first and second cam surfaces.

20. The system of claim 16, further comprising a suction pathway extending through the tissue removal member and the first and second cam members.

21. The system of claim 20, wherein the suction pathway is coaxial with the rotation axis.

22. The system of claim 16, wherein the shaft extends through the first and second cam members.

23. The system of claim 22, wherein the shaft is slidably coupled to the first cam member, allowing the shaft to linearly reciprocate relative to the first cam member during rotation of the rotatable hub about the axis.

24. The system of claim 22, wherein the shaft is rotatably coupled to the second cam member, allowing the second cam member to rotate about the shaft during rotation of the rotatable hub about the axis.

25. A tissue removal device for being driven by a powered rotary handpiece, the tissue removal deice comprising:

a longitudinal axis;

a motion conversion mechanism having a rotating member;

a tissue removal member having a shaft and a cutting head, the shaft coupled in sliding contact with the rotating member, the cutting head including a first jaw member coupled to a second jaw member, the cutting head actuable between an open position in which a first edge on the first jaw member is spaced apart from a second edge on the second jaw member and a closed position in which the first edge abuts the second edge in order to sever tissue between the first and second edges;

wherein when the rotating member is rotated about the longitudinal axis, the motion conversion mechanism is configured to urge a translational motion of the shaft along the longitudinal axis, wherein the translational motion consists of a reciprocating translation between a first retracted position and a second extended position; and, wherein each of the of the first and second jaw members is configured to pivot about a pivot axis to move the cutting head between the open and closed positions.

26. The tissue removal device of claim 25, wherein the pivot axis is perpendicular to the longitudinal axis.

27. The tissue removal device of claim 26, wherein the tissue removal member further comprises a hollow sleeve through which the shaft extends.

28. The tissue removal device of claim 27, wherein at least one of the first and second jaw members is carried on the hollow sleeve.

29. The tissue removal device of claim 25, wherein the shaft is configured to be translated between the retracted and extended positions and thereby control an actuation of the cutting head between the open and closed positions.

30. The tissue removal device of claim 29, wherein the cutting head is in the open position when the shaft is in the extended position and in the closed position when the shaft is in the retracted position.

31. The tissue removal device of claim 29, wherein the cutting head is in the open position when the shaft is in the retracted position and in the closed position when the shaft is in the extended position.

32. The tissue removal device of claim 25, wherein at least one of the first and second edges comprises a plurality of teeth to provide a serrated cutting surface.

33. The tissue removal device of claim 25, wherein a cavity is formed between the first and second jaw members when the cutting head is in the closed position.

* * * * *

UNITED STATES PATENT AND TRADEMARK OFFICE
CERTIFICATE OF CORRECTION

| | | |
|---|---|---|
| PATENT NO. | : 9,005,203 B2 | Page 1 of 1 |
| APPLICATION NO. | : 13/231138 | |
| DATED | : April 14, 2015 | |
| INVENTOR(S) | : Keith J. Nelson et al. | |

It is certified that error appears in the above-identified patent and that said Letters Patent is hereby corrected as shown below:

In the Claims

In column 27, claim 25, line 42, after "the tissue removal" replace "deice" with --device--.

Signed and Sealed this
Fifth Day of January, 2016

Michelle K. Lee
*Director of the United States Patent and Trademark Office*